US007799505B2

(12) United States Patent
Kodama et al.

(10) Patent No.: US 7,799,505 B2
(45) Date of Patent: Sep. 21, 2010

(54) PHOTOSENSITIVE COMPOSITION, COMPOUND FOR USE IN THE PHOTOSENSITIVE COMPOSITION AND PATTERN FORMING METHOD USING THE PHOTOSENSITIVE COMPOSITION

(75) Inventors: Kunihiko Kodama, Shizuoka (JP); Tomotaka Tsuchimura, Shizuoka (JP); Hiroshi Saegusa, Shizuoka (JP); Hideaki Tsubaki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/876,945

(22) Filed: Oct. 23, 2007

(65) Prior Publication Data

US 2008/0138742 A1 Jun. 12, 2008

(30) Foreign Application Priority Data

Oct. 23, 2006 (JP) ............................ 2006-287220

(51) Int. Cl.
*G03F 7/004* (2006.01)
*G03F 7/30* (2006.01)

(52) U.S. Cl. .................... 430/270.1; 430/326; 430/905; 430/910; 430/921; 430/922; 522/31; 549/43; 568/34

(58) Field of Classification Search .............. 430/270.1, 430/326, 905, 910, 921, 922; 549/150, 43; 522/31; 568/34
See application file for complete search history.

(56) References Cited

U.S. PATENT DOCUMENTS

| | | | | |
|---|---|---|---|---|
| 6,358,665 | B1 | 3/2002 | Pawlowski et al. | |
| 6,420,085 | B1 | 7/2002 | Nishi et al. | |
| 6,991,888 | B2 * | 1/2006 | Padmanaban et al. | 430/270.1 |
| 2005/0271974 | A1 * | 12/2005 | Rahman et al. | 430/270.1 |
| 2006/0147836 | A1 * | 7/2006 | Hatakeyama et al. | 430/270.1 |
| 2006/0234160 | A1 * | 10/2006 | Hasegawa et al. | 430/270.1 |
| 2007/0072115 | A1 * | 3/2007 | Hatakeyama et al. | 430/270.1 |
| 2007/0111138 | A1 * | 5/2007 | Rahman et al. | 430/270.1 |
| 2007/0141512 | A1 * | 6/2007 | Wada et al. | 430/270.1 |
| 2007/0184382 | A1 * | 8/2007 | Yamaguchi et al. | 430/270.1 |

FOREIGN PATENT DOCUMENTS

| | | | |
|---|---|---|---|
| JP | 2000-47387 | A | 2/2000 |
| WO | 00/08525 | A1 | 2/2000 |

* cited by examiner

*Primary Examiner*—John S Chu
(74) *Attorney, Agent, or Firm*—Sughrue Mion, PLLC

(57) ABSTRACT

The invention is related to an arylsulfonium salt compound having a polycyclic hydrocarbon structure in a cation moiety.

16 Claims, 1 Drawing Sheet

PHOTOSENSITIVE COMPOSITION, COMPOUND FOR USE IN THE PHOTOSENSITIVE COMPOSITION AND PATTERN FORMING METHOD USING THE PHOTOSENSITIVE COMPOSITION

FIELD OF THE INVENTION

The present invention relates to a photosensitive composition for use in the process of producing a semiconductor such as IC, in the production of a circuit board for liquid crystal, thermal head and the like, and in other photofabrication processes, a compound for use in the photosensitive composition, and a pattern forming method using the photosensitive composition. More specifically, the present invention relates to a photosensitive composition suitable for the process using an exposure light source of far ultraviolet ray or the like at 250 nm or less, preferably 220 nm or less, or an irradiation source by an electron beam or the like, a compound for use in the photosensitive composition, and a pattern forming method using the photosensitive composition.

BACKGROUND OF THE INVENTION

The chemical amplification-type photosensitive composition is a pattern forming material capable of producing an acid in the exposed area upon irradiation with radiation such as far ultraviolet light and through a reaction using this acid as the catalyst, changing the solubility in a developer between the area irradiated with actinic radiation and the non-irradiated area, thereby forming a pattern on a substrate.

In the case of using a KrF excimer laser as the exposure light source, a resin having small absorption in the region of 248 nm and having a basic skeleton of poly(hydroxystyrene) is predominantly used as the main component, and this is an excellent system capable of forming a good pattern with high sensitivity and high resolution as compared with the conventional naphthoquinonediazide/novolak resin system.

In the case of using a light source of emitting light at a shorter wavelength, for example, in using an ArF excimer laser (193 nm) as the light source, the compound having an aromatic group substantially has large absorption in the region of 193 nm and therefore, a satisfactory pattern cannot be formed even by the above-described chemical amplification system.

In order to solve this problem, a resist containing a resin having an alicyclic hydrocarbon structure has been developed for use with an ArF excimer laser. Also, as for the photoacid generator capable of producing an acid in the exposed area upon irradiation with radiation such as far ultraviolet light, various compounds have been developed and, for example, a sulfonium salt compound having a specific substituent is disclosed (see, WO 00/08525 (corresponding to U.S. Pat. No. 6,358,665 B1), and JP-A-2000-47387 (the term "JP-A" as used herein means an "unexamined published Japanese patent application")).

However, in view of integrated performance as the resist, an appropriate combination is actually very difficult to find out for the resin, photoacid generator, additive, solvent and the like used. Moreover, at the time of forming a fine pattern with a line width of 100 nm or less, even when the resolving performance is excellent, this is still insufficient in terms of pattern collapse that the line pattern formed collapses and works out to a defect at the production of a device or in terms of difference in the performance between dense pattern and isolated patter, particularly, the film loss of isolated pattern.

SUMMARY OF THE INVENTION

Accordingly, an object of the present invention is to provide a photosensitive composition ensuring that the pattern collapse is improved and a pattern with good profile can be formed even at the formation of a fine pattern of 100 nm or less, a composition for use in the photosensitive composition, and a pattern forming method using the photosensitive composition.

The present invention is as follows, (1) A photosensitive composition comprising (A) an arylsulfonium salt compound having a polycyclic hydrocarbon structure in the cation moiety.

(2) A positive photosensitive composition comprising (A) an arylsulfonium salt compound having a polycyclic hydrocarbon structure in the cation moiety and (B) a resin capable of decomposing under the action of an acid to increase the solubility in an alkali developer.

(3) An arylsulfonium salt compound having a polycyclic hydrocarbon structure in the cation moiety.

(4) A compound represented by the following formula (I):

(I)

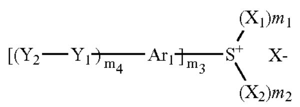

wherein $X_1$ and $X_2$ each independently represents an alkyl group, a cycloalkyl group, an aryl group or an aralkyl group, and $X_1$ and $X_2$ may combine to form a ring structure, $Ar_1$ represents an aryl group, $Y_1$ represents a single bond or a divalent linking group, $Y_2$ represents a polycyclic hydrocarbon group, $m_1$ represents a number of 0 to 2, $m_2$ represents a number of 0 to 2, $m_3$ represents a number of 1 to 3, provided that $m_1+m_2+m_3=3$, $m_4$ represents a number of 1 to 3, and $X^-$ represents a counter anion (5) A pattern forming method comprising steps of forming a photosensitive film from the photosensitive composition described in (1) or (2), and exposing and developing the photosensitive film.

(6) The positive photosensitive composition as described in (2), wherein the resin as the component (B) is a resin containing a hydroxystyrene repeating unit.

(7) The positive photosensitive composition as described in (2), wherein the resin as the component (B) is a resin having a monocyclic or polycyclic alicyclic hydrocarbon structure.

(8) The positive photosensitive composition as described in (2), wherein the resin as the component (B) is a resin having a silicon atom.

(9) The positive photosensitive composition as described in (2), wherein the resin as the component (B) is a resin containing a repeating unit having a lactone structure.

According to the present invention, there can be provided a photosensitive composition ensuring that the pattern collapse is improved and a pattern with good profile can be formed even at the formation of a fine pattern of 100 nm or less, a composition for use in the photosensitive composition, and a pattern forming method using the photosensitive composition.

DETAILED DESCRIPTION OF THE INVENTION

Figure 1:
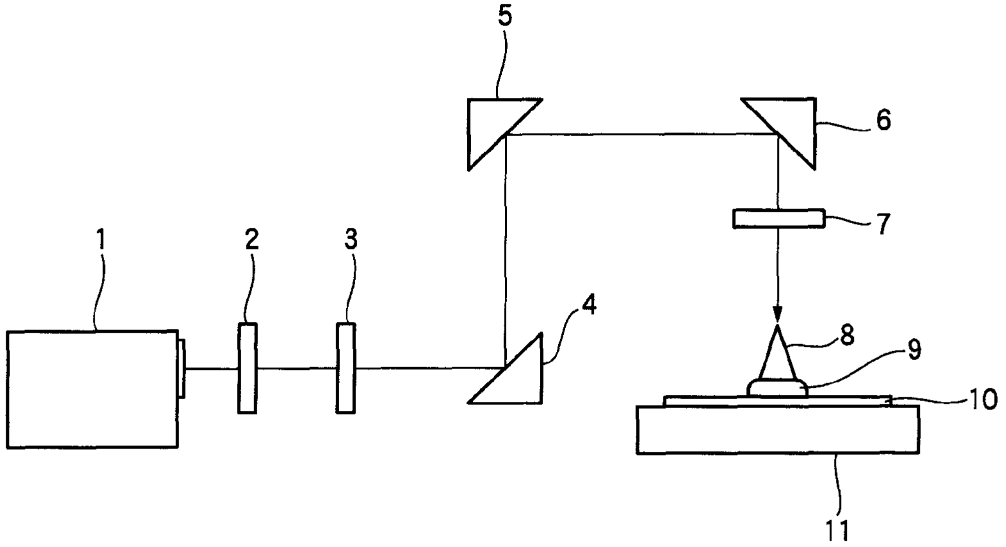
FIG. 1 is a schematic view of the two-beam interference exposure testing apparatus.

The best mode for carrying out the present invention is described below. Incidentally, in the present invention, when a group (atomic group) is denoted without specifying whether substituted or unsubstituted, the group includes both a group having no substituent and a group having a substituent. For example, an "alkyl group" includes not only an alkyl group having no substituent (unsubstituted alkyl group) but also an alkyl group having a substituent (substituted alkyl group).

(A) Arylsulfonium Salt Compound Having a Polycyclic Hydrocarbon Structure in the Cation Moiety The photosensitive composition of the present invention contains an arylsulfonium salt compound having a polycyclic hydrocarbon structure in the cation moiety (hereinafter sometimes called a "compound as the component (A)").

The arylsulfonium salt compound having a polycyclic hydrocarbon structure in the cation moiety is a compound capable of generating an acid upon irradiation with actinic rays or radiation.

As for the arylsulfonium salt compound having a polycyclic hydrocarbon structure in the cation moiety, any compound may be used as long as it is an arylsulfonium salt with an aryl group being bonded to sulfur cation and has a polycyclic hydrocarbon structure in the cation moiety. In the arylsulfonium salt, all substituents bonded the sulfur atom may be an aryl group, or a part of the substituents bonded to the sulfur atom may be an aryl group, with the remaining being an alkyl group, a cycloalkyl group or an aralkyl group. The polycyclic hydrocarbon structure may be formed in any of the aryl group, aralkyl group, cycloalkyl group and aralkyl group but is preferably formed in the aryl group.

Examples of the arylsulfonium compound include a triarylsulfonium compound, a diarylalkylsulfonium compound, an aryldialkylsulfonium compound, a diarylcycloalkylsulfonium compound, an aryldicycloalkylsulfonium compound, a diarylaralkylsulfonium compound and an aryldiaralkylsulfonium compound.

The aryl group in the arylsulfonium compound is preferably an aryl group having a carbon number of 6 to 20, and examples thereof include a hydrocarbon aryl group such as phenyl group, naphthyl group and anthranyl group, and a heteroaryl group having a heteroatom, such as pyrrole group and indole group.

The alkyl group is preferably an alkyl group having a carbon number of 1 to 20, and examples thereof include a methyl group and an ethyl group.

The cycloalkyl group is preferably a cycloalkyl group having a carbon number of 3 to 20, and examples thereof include a cyclopropyl group, a cyclohexyl group, a norbornane group and an adamantyl group.

The aralkyl group is preferably an aralkyl group having a carbon number of 7 to 20, and examples thereof include a benzyl group and a phenethyl group.

The arylsulfonium salt compound having a polycyclic hydrocarbon structure in the cation moiety is preferably a compound represented by the following formula (I)

(I)

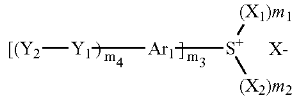

wherein $X_1$ and $X_2$ each independently represents an alkyl group, a cycloalkyl group, an aryl group or an aralkyl group, and $X_1$ and $X_2$ may combine to form a ring structure, $Ar_1$ represents an aryl group, $Y_1$ represents a single bond or a divalent linking group, $Y_2$ represents a polycyclic hydrocarbon group, $m_1$ represents a number of 0 to 2, $m_2$ represents a number of 0 to 2, $m_3$ represents a number of 1 to 3, provided that $m_1+m_2+m_3=3$, $m_4$ represents a number of 1 to 3, and $X^-$ represents a counter anion.

In formula (I), the aryl group in $X_1$, $X_2$ and $Ar_1$ is preferably an aryl group having a carbon number of 6 to 20, and examples thereof include a hydrocarbon aryl group such as phenyl group, naphthyl group and anthranyl group, and a heteroaryl group such as pyrrole group and indole group. The aryl group is more preferably a phenyl group, a naphthyl group or an indole group.

The alkyl group in $X_1$ and $X_2$ is preferably an alkyl group having a carbon number of 1 to 20, and examples thereof include a methyl group and an ethyl group.

The cycloalkyl group in $X_1$ and $X_2$ is preferably a cycloalkyl group having a carbon number of 3 to 20, and examples thereof include a cyclopropyl group, a cyclohexyl group, a norbornane group and an adamantyl group.

The aralkyl group in $X_1$ and $X_2$ is preferably an aralkyl group having a carbon number of 7 to 20, and examples thereof include a benzyl group and a phenethyl group.

$X_1$ and $X_2$ are preferably such that $X_1$ and $X_2$ both are a phenyl group or $X_1$ and $X_2$ combine together to form an alkylene group (preferably having a carbon number of 4 to 6).

Examples of the divalent linking group of $Y_1$ include an alkylene group, an arylene group, —O—, —S—, —C(=O)—, —C(=O)—O—, $—SO_2—$, $—SO_3—$, —C(=O)NRd-, $—SO_2NRd$-, and a divalent linking group comprising a plurality of these in combination. In the formula, Rd represents a hydrogen atom or an alkyl group.

The polycyclic hydrocarbon group of $Y_2$ is preferably a bicyclic or greater polycyclic hydrocarbon group, and more preferred examples thereof include an adamantyl group, a norbornane group, a bicyclo[2.2.2]octane group, a tetracyclododecanyl group, a tricyclodecanyl group and a diamantyl group. The polycyclic hydrocarbon group is preferably an adamantyl group.

The counter anion of $X^-$ includes an organic anion having a carbon atom, such as sulfonate anion, carboxylate anion, bis-sulfonylimide anion and tris-sulfonylmethide anion, and an inorganic anion such as $BF_4^-$, $PF_6^-$, $AsF_6^-$ and $ClO_4^-$, and is preferably an organic anion.

The preferred organic anion includes the organic anions represented by the following formulae (AN1) to (AN4)

AN1

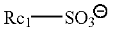

-continued

AN2

$Rc_1—CO_2^{\ominus}$

AN3

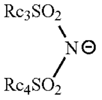

AN4

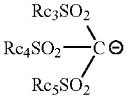

In formulae (AN1) and (AN2), $Rc_1$ represents an organic group.

The organic group in $Rc_1$ includes an organic group having a carbon number of 1 to 30 and is preferably an alkyl group, an aryl group or a group where a plurality of these groups are connected through a single bond or a linking group such as —O—, —$CO_2$—, —S—, —$SO_3$— and —$SO_2N(Rd_1)$-. $Rd_1$ represents a hydrogen atom or an alkyl group and may form a ring structure with the alkyl or aryl group to which $Rd_1$ is bonded.

The organic group of $Rc_1$ is more preferably an alkyl group substituted by a fluorine atom or a fluoroalkyl group at the 1-position, or a phenyl group substituted by a fluorine atom or a fluoroalkyl group. By virtue of having a fluorine atom or a fluoroalkyl group, the acidity of the acid generated upon irradiation with light increases and the sensitivity is enhanced. When $Rc_1$ has 5 or more carbon atoms, at least one carbon atom is preferably such that all hydrogen atoms are not replaced by fluorine atoms and the number of hydrogen atoms is more preferably larger than the number of fluorine atoms. The absence of a perfluoroalkyl group having a carbon number of 5 or more enables reduction in the toxicity to ecology.

The still more preferred embodiment of $Rc_1$ is a group represented by the following formula.

$Rc_7$-Ax-$Rc_6$-

In the formula, $Rc_6$ represents a perfluoroalkylene group having a carbon number of 4 or less, preferably from 2 to 4; more preferably 2 or 3, or a phenylene group substituted by from 3 or 4 fluorine atoms and/or from 1 to 3 fluoroalkyl groups.

Ax represents a single bond or a divalent linking group (preferably —O—, —$CO_2$—, —S—, —$SO_3$— or —$SO_2N(Rd_1)$-). $Rd_1$ represents a hydrogen atom or an alkyl group and may combine with $Rc_7$ to form a ring structure.

$Rc_7$ represents a hydrogen atom, a fluorine atom, a linear or branched alkyl group which may be substituted, a monocyclic or polycyclic cycloalkyl group, or an aryl group which may be substituted. The alkyl group, cycloalkyl group and aryl group, which each may be substituted, preferably contain no fluorine atom as the substituent.

In formulae (AN3) and (AN4), $Rc_3$, $Rc_4$ and $Rc_5$ each independently represents an organic group.

The preferred organic groups for $Rc_3$, $Rc_4$ and $Rc_5$ are the same as the preferred organic groups in $Rc_1$.

$Rc_3$ and $Rc_4$ may combine to form a ring. The group formed after $Rc_3$ and $Rc_4$ are combined includes an alkylene group and an arylene group and is preferably a perfluoroalkylene group having a carbon number of 2 to 4. When $Rc_3$ and $Rc_4$ combine to form a ring, the acidity of the acid generated upon irradiation with light increases and this is preferred because the sensitivity is enhanced.

The arylsulfonium salt compound having a polycyclic hydrocarbon structure in the cation moiety is more preferably a compound represented by the following formula (I-a) or (I-b):

(I-a)

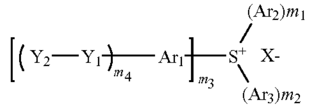

(I-b)

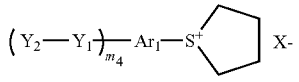

In formulae (I-a) and (I-b) $Ar_1$, $Y_1$, $Y_2$, $m_1$, $m_2$, $m_3$, $m_4$ and $X^-$ have the same meanings as $Ar_1$, $Y_1$, $Y_2$, $m_1$, $m_2$, $m_3$, $m_4$ and $X^-$ in formula (I).

$Ar_2$ and $Ar_3$ each represents an aryl group.

Preferred examples of the substituent which $Ar_1$, $Ar_2$, $Ar_3$ and $Y_2$ in formulae (I-a) and (I-b) each may have include an alkyl group, an alkoxy group, a hydroxyl group, a cyano group, a halogen atom and an alkoxycarbonyl group.

Specific preferred examples of the sulfonium cation in the compound as the component (A) are set forth below, but the present invention is not limited thereto.

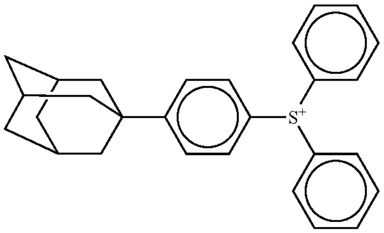

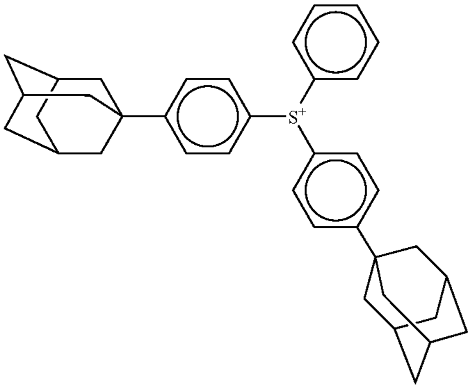

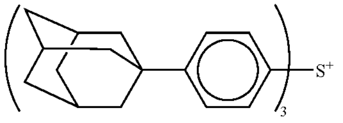

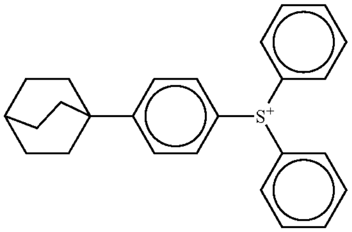

-continued
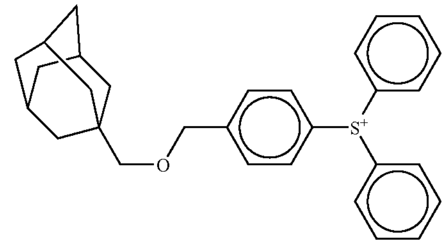
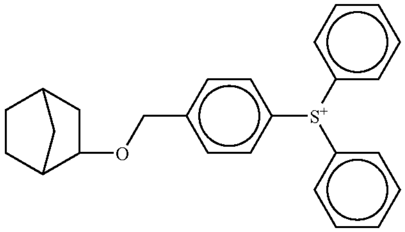
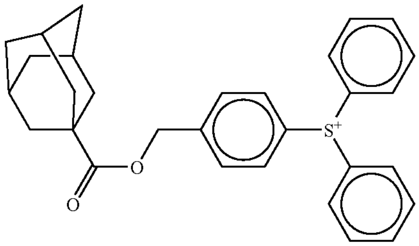
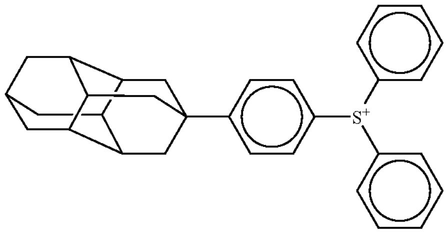
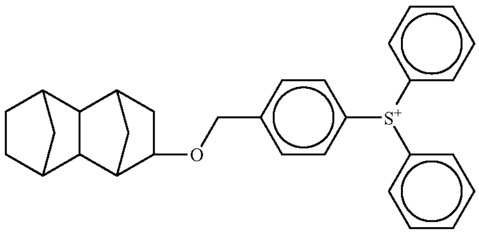
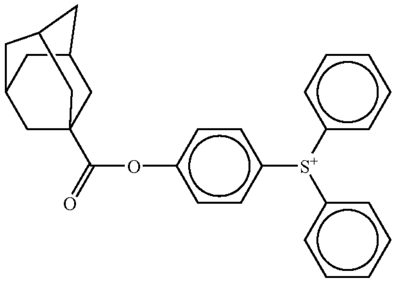
-continued
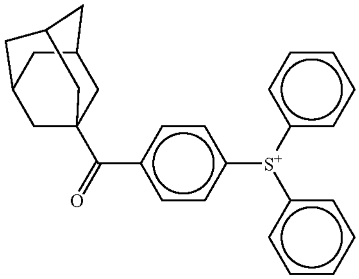
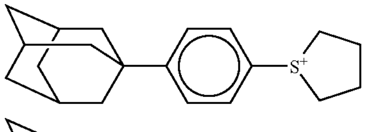
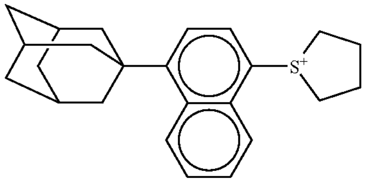
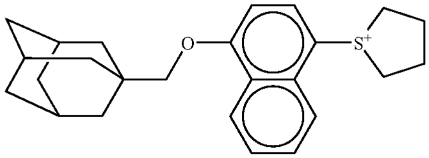
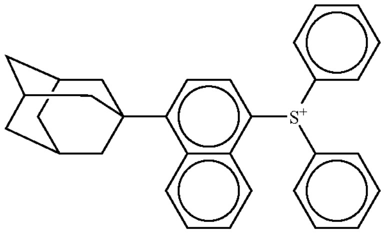
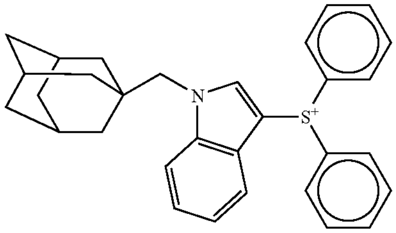
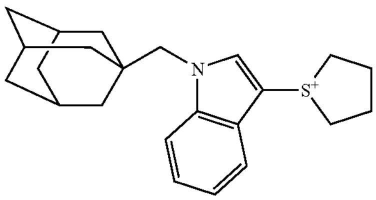
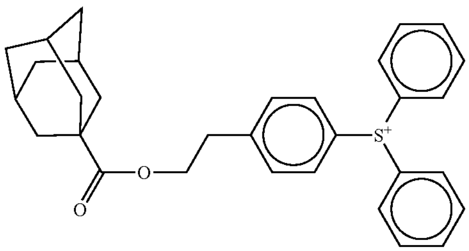

-continued

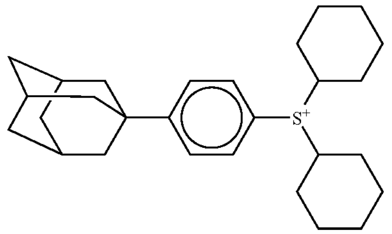

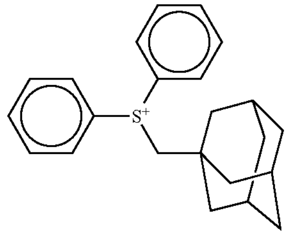

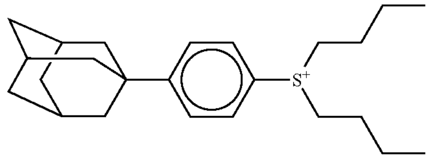

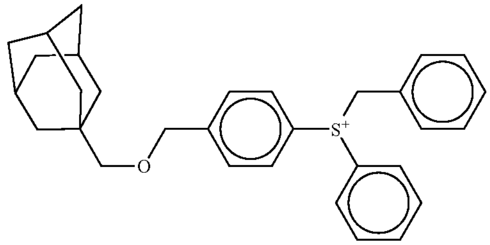

Specific preferred examples of the counter anion in the compound as the component (A) are set forth below, but the present invention is not limited thereto $CF_3SO_3^-$ $C_2F_5SO_3^-$ $C_3F_7SO_3^-$ $C_4F_9SO_3^-$ $C_6F_{13}SO_3^-$ $C_8F_{17}SO_3^-$

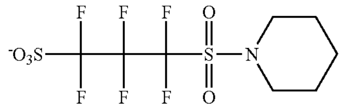

$C_2F_5$—O—$C_2F_4SO_3^-$ 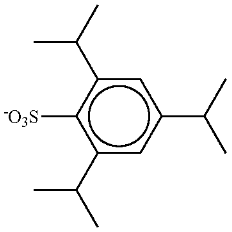

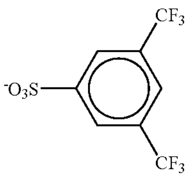 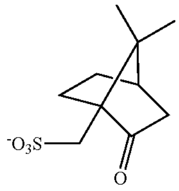

-continued

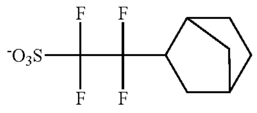 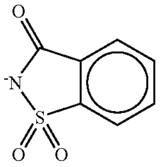

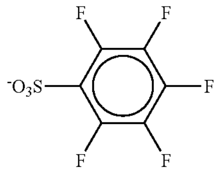 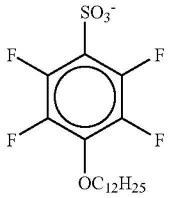

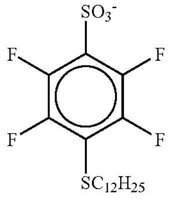 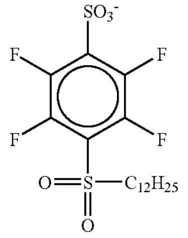

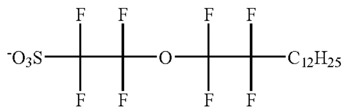

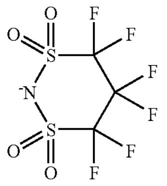 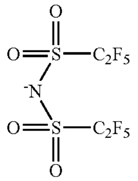 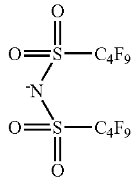

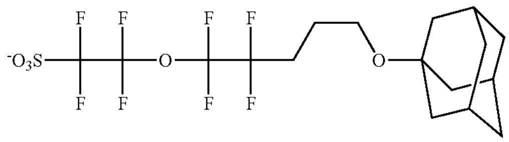

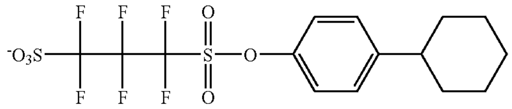

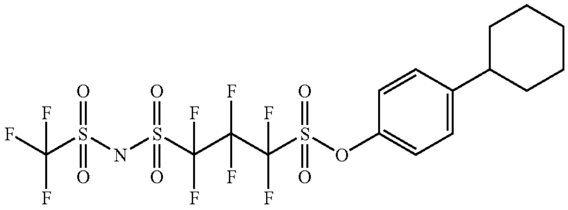

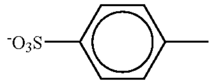 $PF_6^-$ $BF_4^-$ $AsF_6^-$

The compound as the component (A) is preferably an arbitrary combination of the above-described preferred sulfonium cation and the preferred counter anion.

Particularly preferred compounds as the component (A) are set forth below, but the present invention is not limited thereto -continued
I-1
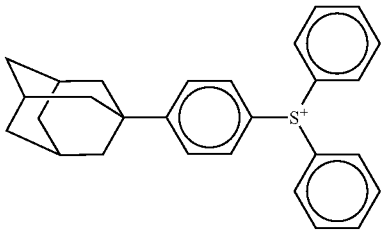
$C_4F_9SO_3^-$
I-2
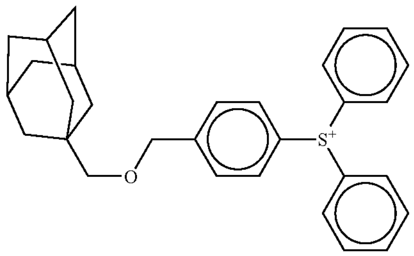
$C_4F_9SO_3^-$
I-3
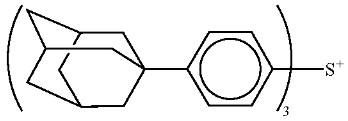
$C_4F_9SO_3^-$
I-4
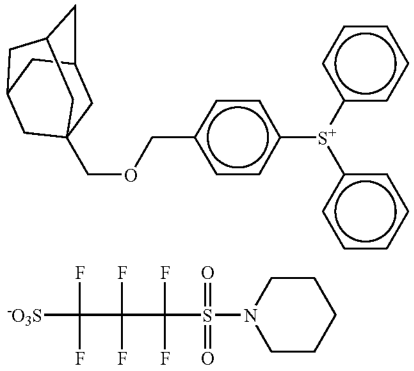
I-5
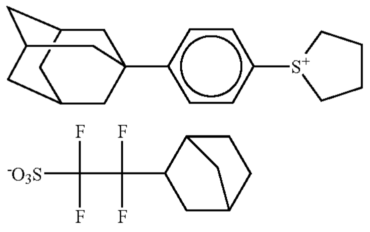
I-6
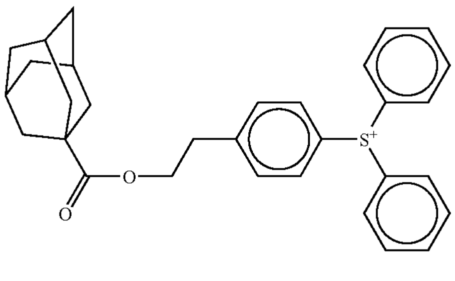
$C_3F_7SO_3^-$
I-7
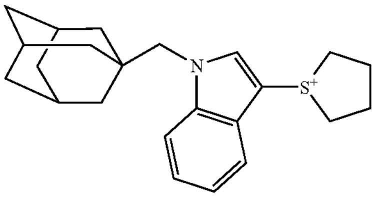
$C_3F_7SO_3^-$
I-8
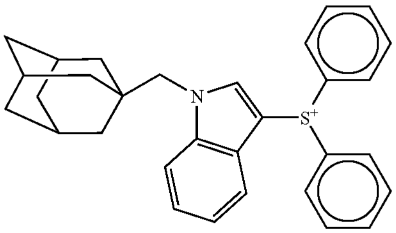
$C_3F_7SO_3^-$
I-9
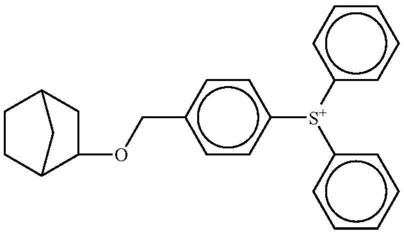
$C_3F_7SO_3^-$
I-10
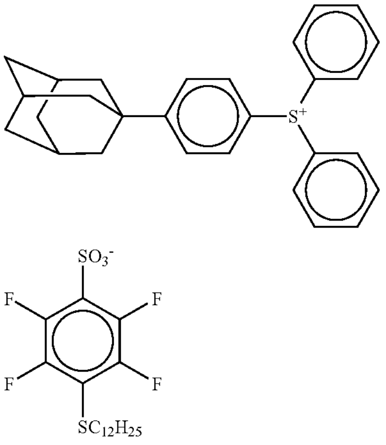
I-11
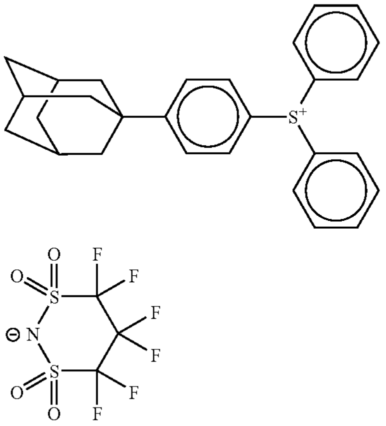

-continued

I-12

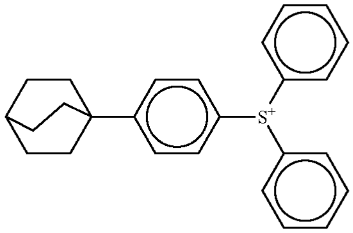

$C_3F_7SO_3^-$

I-13

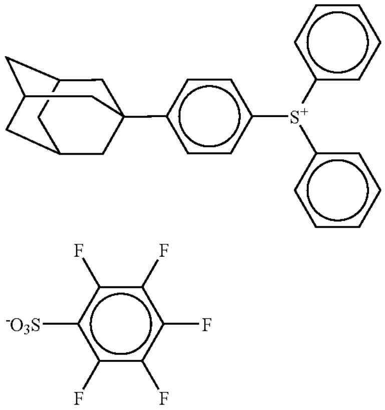

I-14

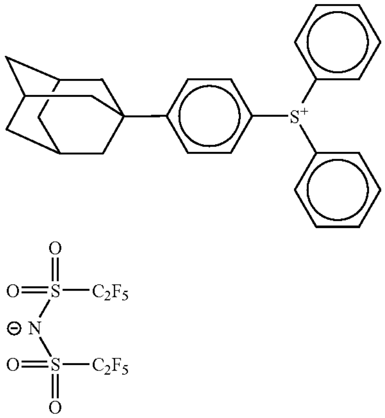

I-15

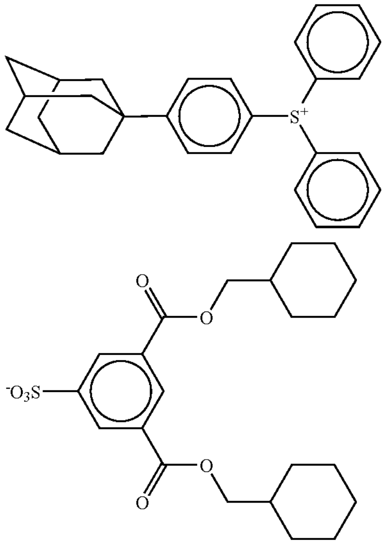

-continued

I-16

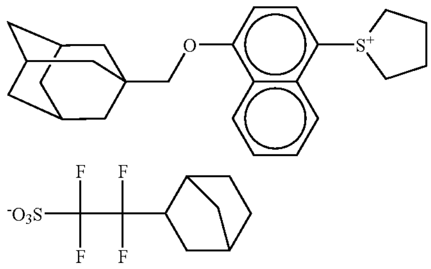

I-17

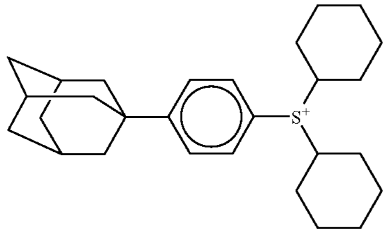

$C_3F_7SO_3^-$

I-18

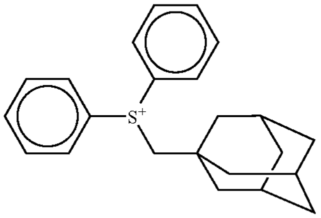

$C_3F_7SO_3^-$

I-19

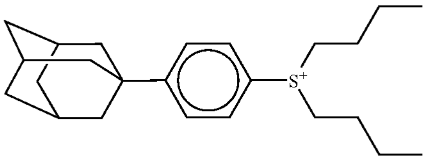

$C_3F_7SO_3^-$

I-20

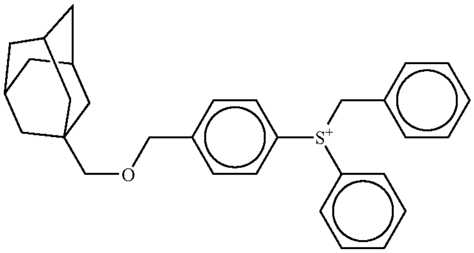

$C_3F_7SO_3^-$

The compound as the component (A) is a novel compound.

The compound as the component (A) can be synthesized, for example, by reacting a polycyclic hydrocarbon group-containing aryl group and a sulfoxide compound to form the cation moiety and performing salt exchange with a desired counter anion.

The content of the compound as the component (A) in the composition is preferably from 0.1 to 20 mass %, more preferably from 0.5 to 10 mass %, still more preferably from 1 to 7 mass %, yet still more preferably from 3 to 7 wt %, based on the entire solid content of the photosensitive composition.

In the photosensitive composition of the present invention, a compound capable of generating an acid upon irradiation with actinic rays or radiation, other than the arylsulfonium salt compound having a polycyclic hydrocarbon structure in the cation moiety, may be used in combination.

As regards such an acid generator, a photoinitiator for photocationic polymerization, a photoinitiator for photoradical polymerization, a photo-decoloring agent for coloring matters, a photo-discoloring agent, a known compound capable of generating an acid upon irradiation with actinic rays or radiation, which is used for microresist and the like, or a mixture thereof may be appropriately selected and used.

Examples thereof include diazonium salt, phosphonium salt, sulfonium salt, iodonium salt, imidosulfonate, oxime sulfonate, diazodisulfone, disulfone and o-nitrobenzyl sulfonate.

Also, a compound where the above-described group or compound capable of generating an acid upon irradiation with actinic rays or radiation is introduced into the polymer main or side chain, such as compounds described in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029, may be used.

Furthermore, compounds capable of generating an acid by the effect of light described, for example, in U.S. Pat. No. 3,779,778 and European Patent 126,712 may also be used.

Among the compounds capable of generating an acid upon irradiation with actinic rays or radiation, which can be used in combination, the compounds represented by the following formulae (ZI), (ZII) and (ZIII) are preferred.

ZI

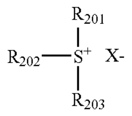

ZII

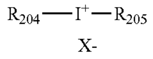

ZIII

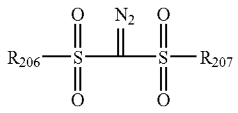

In formula (ZI), $R_{201}$, $R_{202}$ and $R_{203}$ each independently represents an organic group.

$X^-$ represents a counter anion and is the same as the counter anion of $X^-$ in formula (I).

The carbon number of the organic group as $R_{201}$, $R_{202}$ and $R_{203}$ in formula (ZI) is generally from 1 to 30, preferably from 1 to 20.

Two members out of $R_{201}$ to $R_{203}$ may combine to form a ring structure, and the ring may contain an oxygen atom, a sulfur atom, an ester bond, an amide bond or a carbonyl group. Examples of the group formed by combining two members out of $R_{201}$ to $R_{203}$ include an alkylene group (e.g., butylene, pentylene).

Examples of the organic group as $R_{201}$, $R_{202}$ and $R_{203}$ include the corresponding groups in the compounds (ZI-1), (ZI-2) and (ZI-3) which are described later.

The compound may be a compound having a plurality of structures represented by formula (ZI). For example, the compound may be a compound having a structure that at least one of $R_{201}$ to $R_{203}$ in the compound represented by formula (ZI) is bonded to at least one of $R_{201}$ to $R_{203}$ in another compound represented by formula (ZI).

The component (ZI) is more preferably a compound (ZI-1), (ZI-2) or (ZI-3) described below.

The compound (ZI-1) is an arylsulfonium compound where at least one of $R_{201}$ to $R_{203}$ in formula (ZI) is an aryl group, that is, a compound having an arylsulfonium as the cation.

In the arylsulfonium compound, $R_{201}$ to $R_{203}$ all may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, an aryldialkylsulfonium compound, a diarylcycloalkylsulfonium compound and an aryldicycloalkylsulfonium compound.

The aryl group in the arylsulfonium compound is preferably an aryl group such as phenyl group and naphthyl group, or a heteroaryl group such as indole residue and pyrrole residue, more preferably a phenyl group or an indole residue. In the case where the arylsulfonium compound has two or more aryl groups, these two or more aryl groups may be the same of different.

The alkyl group which is present, if desired, in the arylsulfonium compound is preferably a linear, branched or cyclic alkyl group having a carbon number of 1 to 15, and examples thereof include a methyl group, an ethyl group, a propyl group, an n-butyl group, a sec-butyl group and a tert-butyl group.

The cycloalkyl group which is present, if desired, in the arylsulfonium compound is preferably a cycloalkyl group having a carbon number of 3 to 15, and examples thereof include a cyclopropyl group, a cyclobutyl group and a cyclohexyl group.

The aryl group, alkyl group and cycloalkyl group of $R_{201}$ to $R_{203}$ each may have, as the substituent, an alkyl group (for example, an alkyl group having a carbon number of 1 to 15), a cycloalkyl group (for example, a cycloalkyl group having a carbon number of 3 to 15), an aryl group (for example, an aryl group having a carbon number of 6 to 14), an alkoxy group (for example, an alkoxy group having a carbon number of 1 to 15), a halogen atom, a hydroxyl group or a phenylthio group. The substituent is preferably a linear branched alkyl group having a carbon number of 1 to 12, a cycloalkyl group having a carbon number of 3 to 12, or a linear, branched or cyclic alkoxy group having a carbon number of 1 to 12, more preferably an alkyl group having a carbon number of 1 to 4 or an alkoxy group having a carbon number of 1 to 4. The substituent may be substituted to any one of three members $R_{201}$ to $R_{203}$ or may be substituted to all of these three members. In the case where $R_{201}$ to $R_{203}$ are an aryl group, the substituent is preferably substituted at the p-position of the aryl group.

The compound (ZI-2) is described below.

The compound (ZI-2) is a compound where $R_{201}$ to $R_{203}$ in formula (ZI) each independently represents an aromatic ring-free organic group. The aromatic ring as used herein includes an aromatic ring containing a heteroatom.

The aromatic ring-free organic group as $R_{201}$ to $R_{203}$ generally has a carbon number of 1 to 30, preferably from 1 to 20.

$R_{201}$ to $R_{203}$ each is independently preferably an alkyl group, a cycloalkyl group, an allyl group or a vinyl group, more preferably a linear, branched or cyclic 2-oxoalkyl group or an alkoxycarbonylmethyl group, still more preferably a linear or branched 2-oxoalkyl group.

The alkyl group as $R_{201}$ to $R_{203}$ is preferably a linear or branched alkyl group having a carbon number of 1 to 10 (e.g., methyl, ethyl, propyl, butyl, pentyl). The alkyl group as $R_{201}$ to $R_{203}$ is more preferably a linear or branched 2-oxoalkyl group or an alkoxymethyl group.

The cycloalkyl group as $R_{201}$ to $R_{203}$ is preferably a cycloalkyl group having a carbon number of 3 to 10 (e.g., cyclopentyl, cyclohexyl, norbornyl). The cycloalkyl group as $R_{201}$ to $R_{203}$ is more preferably a cyclic 2-oxoalkyl group.

The linear, branched or cyclic 2-oxoalkyl group as $R_{201}$ to $R_{203}$ is preferably a group having >C═O at the 2-position of the above-described alkyl group or cycloalkyl group.

The alkoxy group in the alkoxycarbonylmethyl group as $R_{201}$ to $R_{203}$ is preferably an alkyl group having a carbon number of 1 to 5 (e.g., methoxy, ethoxy, propoxy, butoxy, pentoxy).

$R_{201}$ to $R_{203}$ each may be further substituted by a halogen atom, an alkoxy group (for example, an alkoxy group having a carbon number of 1 to 5), a hydroxyl group, a cyano group or a nitro group.

The compound (ZI-3) is a compound represented by the following formula (ZI-3), and this is a compound having a phenacylsulfonium salt structure.

(ZI-3)

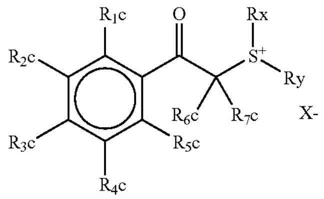

In formula (ZI-3), $R_{1c}$ to $R_{5c}$ each independently represents a hydrogen atom, an alkyl group, a cycloalkyl group, an alkoxy group or a halogen atom.

$R_{6c}$ and $R_{7c}$ each independently represents a hydrogen atom, an alkyl group or a cycloalkyl group.

$R_x$ and $R_y$ each independently represents an alkyl group, a cycloalkyl group, an allyl group or a vinyl group.

Any two or more members out of $R_{1c}$ to $R_{7c}$ or a pair of $R_x$ and $R_y$ may combine with each other to form a ring structure, and the ring structure may contain an oxygen atom, a sulfur atom, an ester bond or an amide bond. Examples of the group formed by combining any two or more members out of $R_{1c}$ to $R_{7c}$ or a pair of $R_x$ and $R_y$ include a butylene group and a pentylene group.

$X^-$ represents a counter anion, and examples thereof are the same as those of the counter anion of $X^-$ in formula (I).

The alkyl group as $R_{1c}$ to $R_{7c}$ is, for example, a linear or branched alkyl group having a carbon number of 1 to 20, preferably a linear or branched alkyl group having a carbon number of 1 to 12 (e.g., methyl, ethyl, linear or branched propyl, linear or branched butyl, linear or branched pentyl).

The cycloalkyl group as $R_{1c}$ to $R_{7c}$ is preferably a cycloalkyl group having a carbon number of 3 to 8 (e.g., cyclopentyl, cyclohexyl).

The alkoxy group as $R_{1c}$ to $R_{5c}$ may be linear, branched or cyclic and is, for example, an alkoxy group having a carbon number of 1 to 10, preferably a linear or branched alkoxy group having a carbon number of 1 to 5 (e.g., methoxy, ethoxy, linear or branched propoxy, linear or branched butoxy, or linear or branched pentoxy), or a cyclic alkoxy group having a carbon number of 3 to 8 (e.g., cyclopentyloxy, cyclohexyloxy).

A compound where any one of $R_{1c}$ to $R_{5c}$ is a linear or branched alkyl group, a cycloalkyl group or a linear, branched or cyclic alkoxy group is preferred, and a compound where the sum of carbon numbers of $R_{1c}$ to $R_{5c}$ is from 2 to 15 is more preferred. By virtue of this construction, the solubility in a solvent is more enhanced and generation of particles during storage is suppressed.

Examples of the alkyl group as $R_x$ and $R_y$ are the same as those of the alkyl group as $R_{1c}$ to $R_{7c}$. The alkyl group as $R_x$ and $R_y$ is preferably a linear or branched 2-oxoalkyl group or an alkoxymethyl group.

Examples of the cycloalkyl group as $R_x$ and $R_y$ are the same as those of the cycloalkyl group as $R_{1c}$ to $R_{7c}$. The cycloalkyl group as $R_x$ and $R_y$ is preferably a cyclic 2-oxoalkyl group.

Examples of the linear or branched 2-oxoalkyl group and cyclic 2-oxcalkyl group include a group having >C═O at the 2-position of the alkyl group or cycloalkyl group as $R_{1c}$ to $R_{7c}$.

Examples of the alkoxy group in the alkoxy-carbonylmethyl group are the same as those of the alkoxy group as $R_{1c}$ to $R_{5c}$.

$R_x$, and $R_y$ each is preferably an alkyl group having a carbon number of 4 or more, more preferably 6 or more, still more preferably 8 or more.

In formulae (ZII) and (ZIII), $R_{204}$ to $R_{207}$ each independently represents an aryl group, an alkyl group or a cycloalkyl group.

The aryl group of $R_{204}$ to $R_{207}$ is preferably a phenyl group or a naphthyl group, more preferably a phenyl group.

The alkyl group of $R_{204}$ to $R_{207}$ is preferably a linear or branched alkyl group having a carbon number of 1 to 10 (e.g., methyl, ethyl, propyl, butyl, pentyl)

The cycloalkyl group of $R_{204}$ to $R_{207}$ is preferably a cycloalkyl group having a carbon number of 3 to 10 (e.g., cyclopentyl, cyclohexyl, norbornyl).

$R_{204}$ to $R_{207}$ each may have a substituent, and examples of the substituent which $R_{204}$ to $R_{207}$ each may have include an alkyl group (for example, an alkyl group having a carbon number of 1 to 15), a cycloalkyl group (for example, a cycloalkyl group having a carbon number of 3 to 15), an aryl group (for example, an aryl group having a carbon number of 6 to 15), an alkoxy group (for example, an alkoxy group having a carbon number of 1 to 15), a halogen atom, a hydroxyl group and a phenylthio group.

$X^-$ represents a counter anion, and examples thereof are the same as those of the counter anion of $X^-$ in formula (I).

Among the compounds capable of generating an acid upon irradiation with actinic rays or radiation, which can be used in combination, the compounds represented by the following formulae (ZIV), (ZV) and (ZVI) also preferred.

ZIV

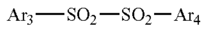

ZV

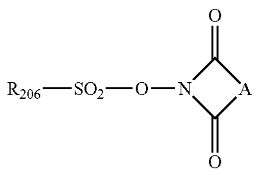

ZVI

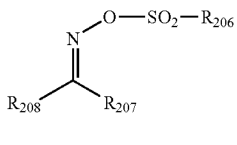

In formulae (ZIV) to (ZVI), $Ar_3$ and $Ar_4$ each independently represents an aryl group.

$R_{206}$ represents an alkyl group, a cycloalkyl group or an aryl group.

$R_{207}$ and $R_{208}$ each independently represents an alkyl group, a cycloalkyl group, an aryl group, or an electron-withdrawing group. $R_{207}$ is preferably an aryl group. $R_{208}$ is preferably an electron-withdrawing group, more preferably a cyano group or a fluoroalkyl group.

A represents an alkylene group, an alkenylene group or an arylene group.

Among the compounds capable of generating an acid upon irradiation with actinic rays or radiation, the compounds represented by formulae (ZI) to (ZIII) are preferred, the compound represented by formula (ZI) is more preferred, and the compounds represented by formulae (ZI-1) to (ZI-3) are still more preferred.

Furthermore, a compound capable of generating an acid represented by any one of the following formulae (AC1) to (AC3) upon irradiation with actinic rays or radiation is preferred.

AC1

$Rc_1$—$SO_3H$

AC2

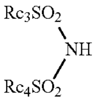

AC3

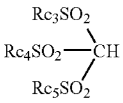

In formulae (AC1) to (AC3), $Rc_1$ and $Rc_3$ to $Rc_5$ have the same meanings as $Rc_1$ and $Rc_3$ to $Rc_5$ in formulae (AN1) to (AN4)

A preferred embodiment of the acid generator is a compound where in the structure of formula (ZI), $X^-$ is a counter anion selected from (AN1), (AN3) and (AN4).

Out of the compounds capable of generating an acid upon irradiation with actinic rays or radiation, which can be used in combination, particularly preferred examples are set forth below.

(z1)

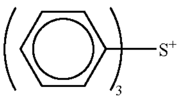 $CF_3SO_3^-$ (z2)

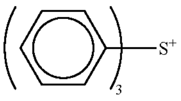 $C_4F_9SO_3^-$ (z3)

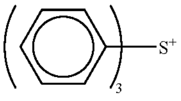 $C_8F_{17}SO_3^-$ (z4)

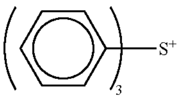 $C_2F_5SO_3^-$ (z5)

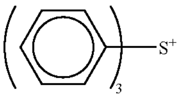 $C_3F_7SO_3^-$

-continued (z6)

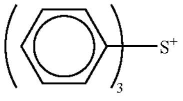 $C_6F_{13}SO_3^-$ (z7)

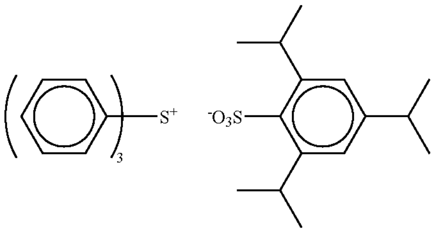

(z8)

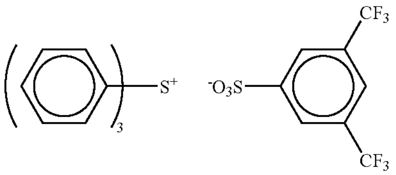

(z9)

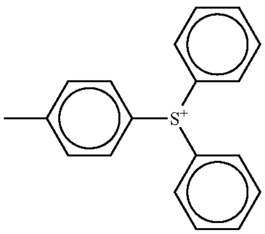 $C_8F_{17}SO_3^-$ (z10)

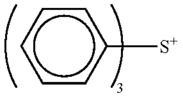 $C_{11}F_{23}COO^-$ (z11)

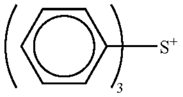 $C_2F_5$—O—$C_2F_4SO_3^-$ (z12)

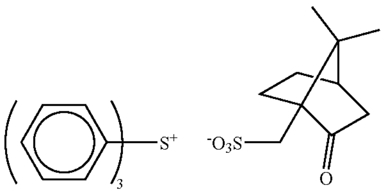

(z13)

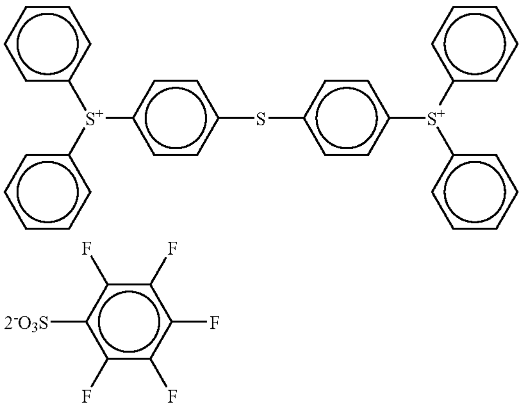

-continued
(z14)
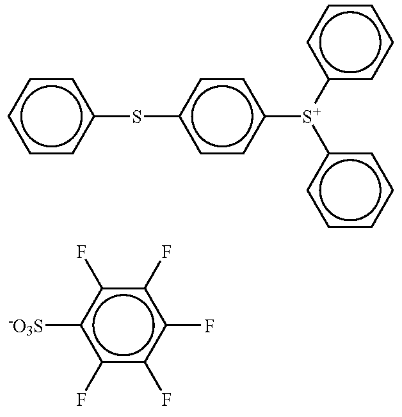
(z15)
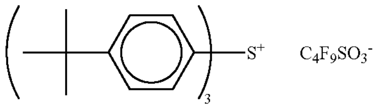
(z16)
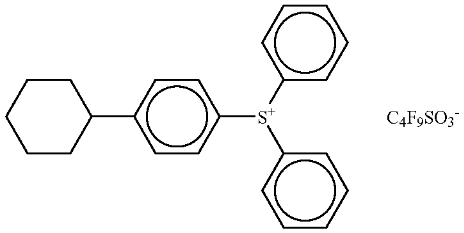
(z17)
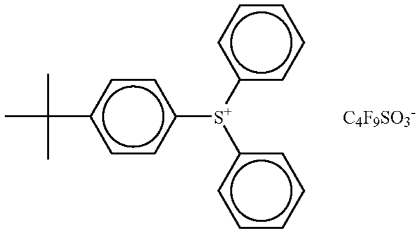
(z18)
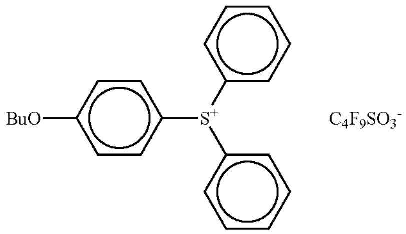
(z19)
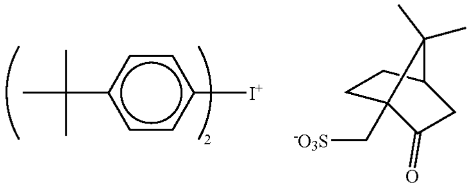
(z20)
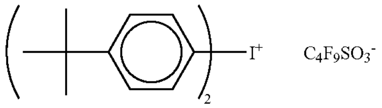
-continued
(z21)
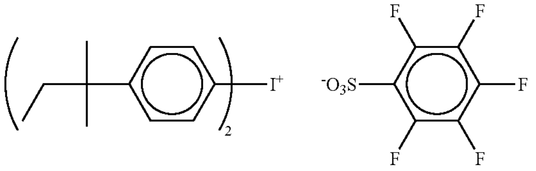
(z22)
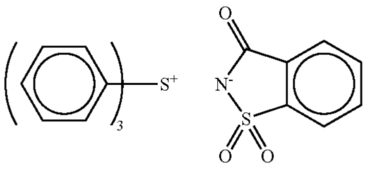
(z23)
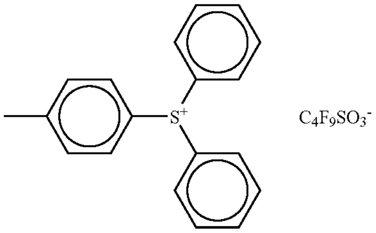
(z24)
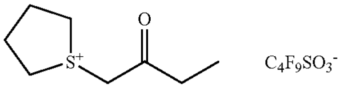
(z25)
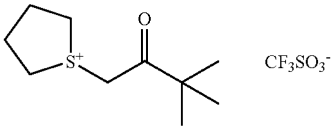
(z26)
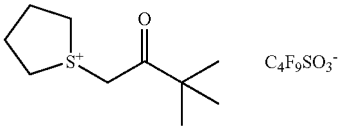
(z27)
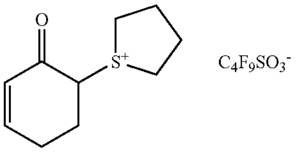
(z28)
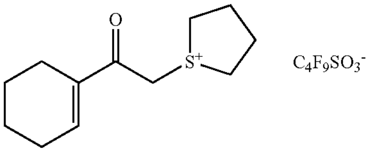
(z29)
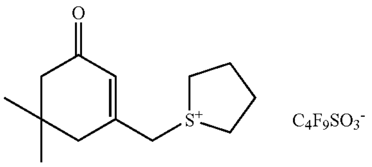

-continued
(z30)
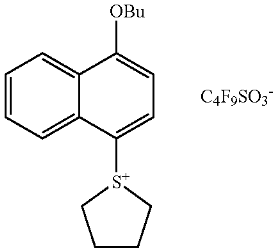
(z31)
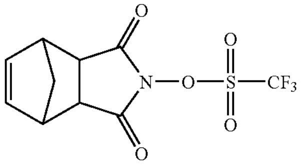
(z32)
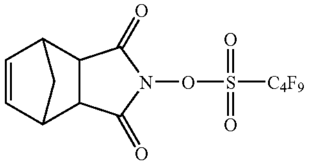
(z33)
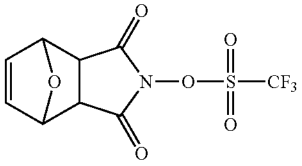
(z34)
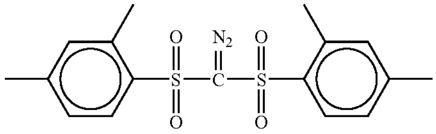
(z35)
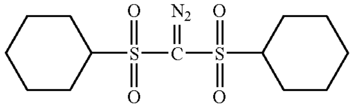
(z36)
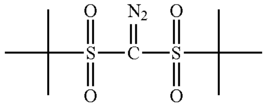
(z37)
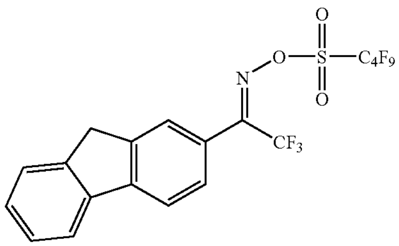
-continued
(z38)
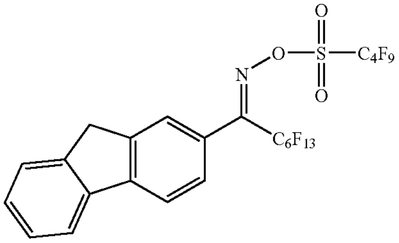
(z39)
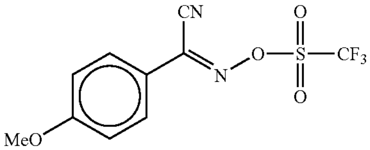
(z40)
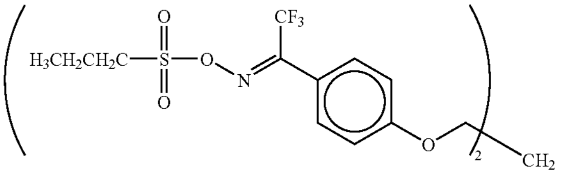
(z41)
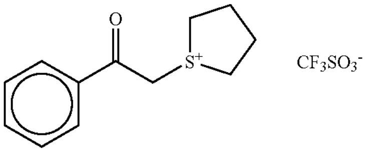
(z42)
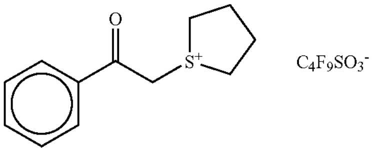
(z43)
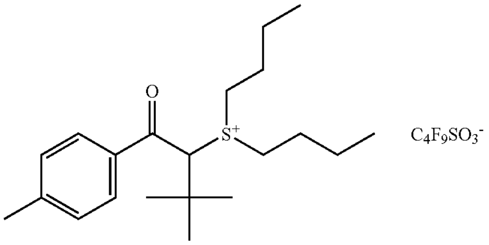
(z44)
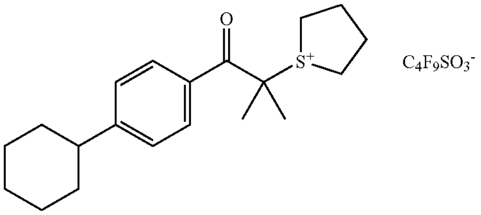
(z45)
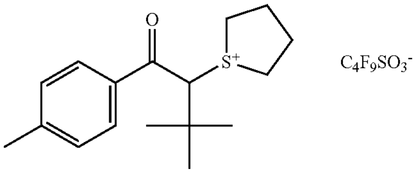

-continued
(z46)
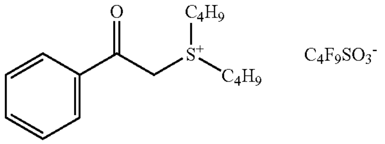
(z47)
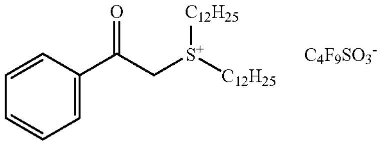
(z48)
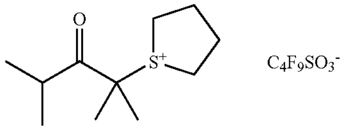
(z49)
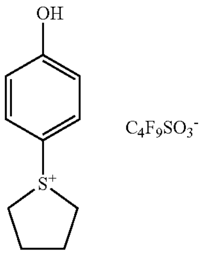
(z50)
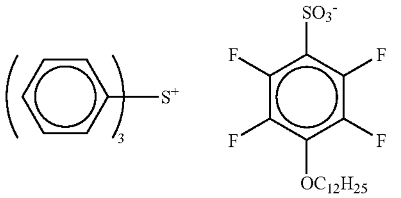
(z51)
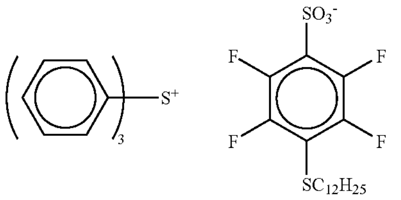
(z52)
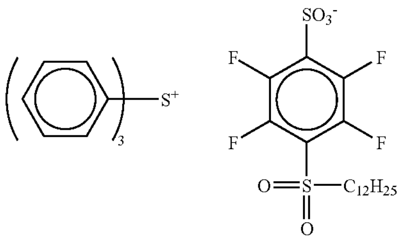
(z53)
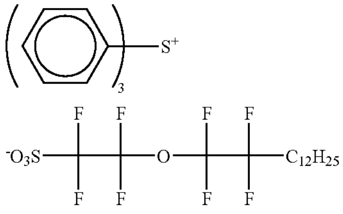
-continued
(z54)
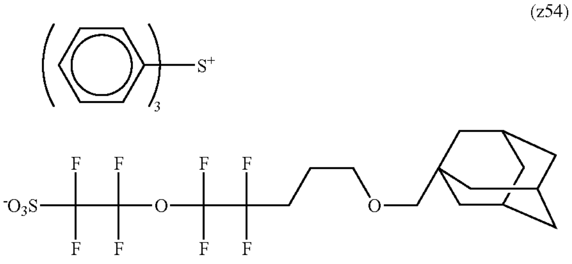
(z55)
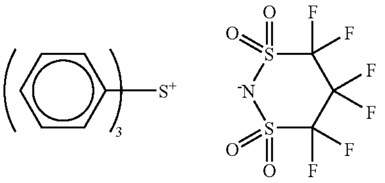
(z56)
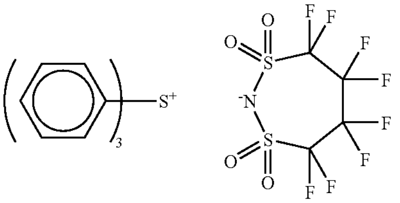
(z57)
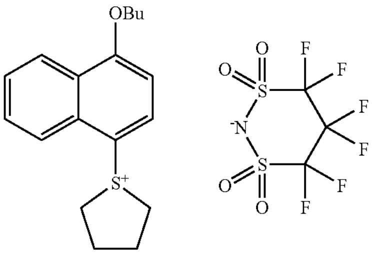
(z58)
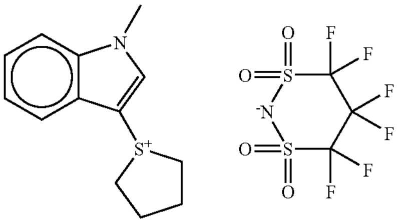
(z59)
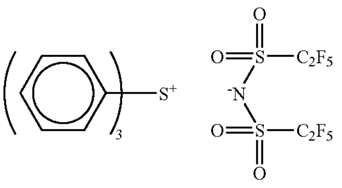
(z60)
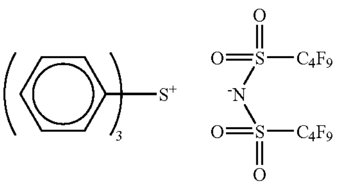

-continued (z61)

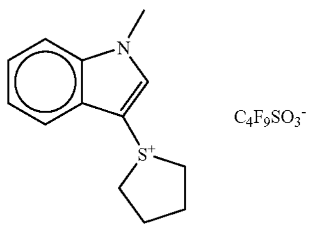

(z62)

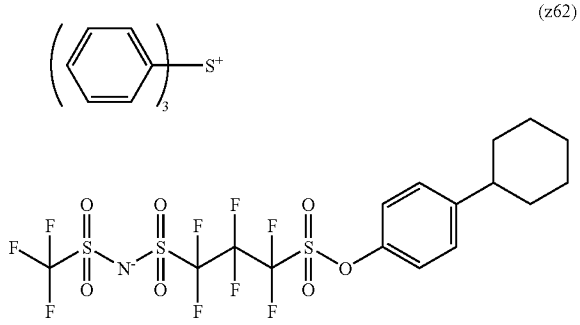

(z63)

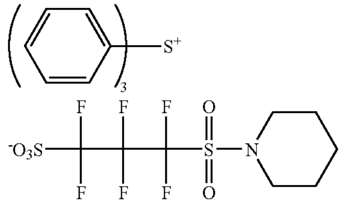

(z64)

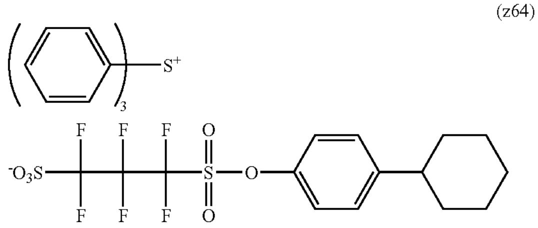

(z65)

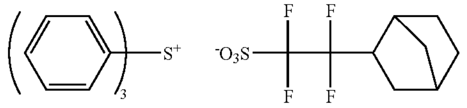

(z66)

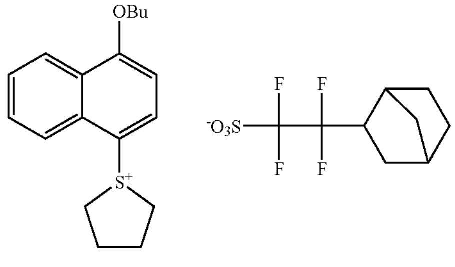

(z67)

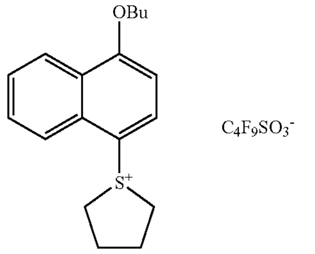

As for the acid generator which can be used in combination, one species may be used alone, or a combination of two or more species may be used. In the case of using a combination of two or more species, compounds capable of generating two or more organic acids differing in the total number of atoms except for hydrogen atom by 2 or more are preferably combined.

The total content of the compound as the component (A) and the acid generator which can be used in combination, in the composition, is preferably from 0.1 to 20 mass %, more preferably from 0.5 to 10 mass %, still more preferably from 1 to 7 mass %, yet still more preferably from 3 to 7 mass %, based on the entire solid content of the resist composition.

The photosensitive composition containing a compound as the component (A) may take a form of positive photosensitive composition or negative photosensitive composition.

The composition containing a compound as the component (A) and (B) a resin capable of decomposing under the action of an acid to increase the solubility in an alkali developer is a positive photosensitive composition and when a photosensitive film is formed, irradiated with actinic rays or radiation and developed with an alkali developer, the exposed area is dissolved and removed, whereby a pattern is formed.

The photosensitive composition containing a compound as the component (A), a resin soluble in an alkali developer, and an acid crosslinking agent capable of crosslinking the resin soluble in an alkali developer under the action of an acid is a negative photosensitive composition and when a photosensitive film is formed, irradiated with actinic rays or radiation and developed with an alkali developer, the unexposed area is dissolved and removed, whereby a pattern is formed.

(B) Resin Capable of Decomposing Under the Action of an Acid to Increase the Solubility in an Alkali Developer The resin capable of decomposing under the action of an acid to increase the solubility in an alkali developer (hereinafter sometimes called a "resin as the component (B)"), which is used in the positive photosensitive composition of the present invention, is a resin having a group capable of decomposing under the action of an acid (hereinafter sometimes referred to as an "acid-decomposable group"), in ether one or both of the main chain and the side chain of the resin. Of these, a resin having an acid-decomposable group in the side chain is preferred.

The group capable of decomposing under the action of an acid is preferably a group resulting from replacement of the hydrogen atom of a —COOH or —OH group by a group which desorbs by the effect of an acid.

Examples of the group which desorbs by the effect of an acid include $—C(R_{36})(R_{37})(R_{38})$, $—C(R_{36})(R_{37})(OR_{39})$, $—C(=O)—O—C(R_{36})(R_{37})(R_{38})$, $—C(R_{01})(R_{02})(OR_{39})$ and $—C(R_{01})(R_{02})—C(=O)—O—C(R_{36})(R_{37})(R_{38})$.

In the formulae, $R_{36}$ to $R_{39}$ each independently represents an alkyl group, a cycloalkyl group, an aryl group, an aralkyl group or an alkenyl group. $R_{36}$ and $R_{37}$ may combine with each other to form a ring.

$R_{01}$ and $R_{02}$ each independently represents a hydrogen atom, an alkyl group, a cycloalkyl group, an aryl group, an aralkyl group or an alkenyl group.

In the present invention, the acid-decomposable group is an acetal group or a tertiary ester group.

In the case where such a group capable of decomposing under the action of an acid is bonded as a side chain, the matrix resin is an alkali-soluble resin having a —OH or —COOH group in the side chain. Examples thereof include an alkali-soluble resin described below.

The alkali dissolution rate of the alkali-soluble resin is preferably 170 Å/sec or more, more preferably 330 Å/sec or more, as measured (at 23° C.) in 0.261N tetramethylammonium hydroxide (TMAH).

From this standpoint, the alkali-soluble resin is preferably an alkali-soluble resin having a hydroxystyrene structural unit, such as an o-, m- or p-poly(hydroxystyrene), a copolymer thereof, a hydrogenated poly(hydroxystyrene), a halogen- or alkyl-substituted poly(hydroxystyrene), a partially O-alkylated or O-acylated poly(hydroxystyrene), a styrene-hydroxystyrene copolymer, an α-methylstyrene-hydroxystyrene copolymer and a hydrogenated novolak resin; or an alkali-soluble resin containing a repeating unit having a carboxyl group such as (meth)acrylic acid and norbornene carboxylic acid.

Preferred examples of the repeating unit having an acid-decomposable group for use in the present invention include a tert-butoxycarbonyloxystyrene, a 1-alkoxyethoxy-styrene and a tertiary alkyl (meth)acrylate. Among these, a 2-alkyl-2-adamantyl (meth)acrylate and a dialkyl(1-adamantyl)methyl (meth)acrylate are more preferred.

The resin as the component (B) for use in the present invention can be obtained by reacting an acid-decomposable group precursor with an alkali-soluble resin or copolymerizing an acid-decomposable group-bonded alkali-soluble resin monomer with various monomers, and this is disclosed in European Patent 254853, JP-A-2-25850, JP-A-3-223860 and JP-A-4-251259.

In the case of irradiating the positive photosensitive composition of the present invention with KrF excimer laser light, electron beam, X ray or high-energy beam at a wavelength of 50 nm or less (preferably, for example, EUV), the resin as the component (B) preferably has a hydroxystyrene repeating unit and is more preferably a copolymer containing a hydroxystyrene repeating unit/a hydroxystyrene repeating unit protected by an acid-decomposable group, or a copolymer containing a hydroxystyrene repeating unit/a (meth) acrylic acid ester repeating unit protected by an acid-decomposable group.

Specific examples of the resin as the component (B) for use in the present invention are set forth below, but the present invention is not limited thereto.

(R-1)

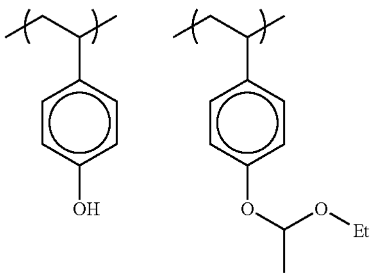

(R-2)

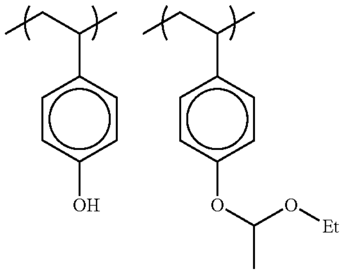

-continued

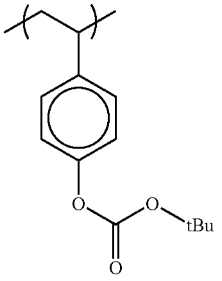

(R-3)

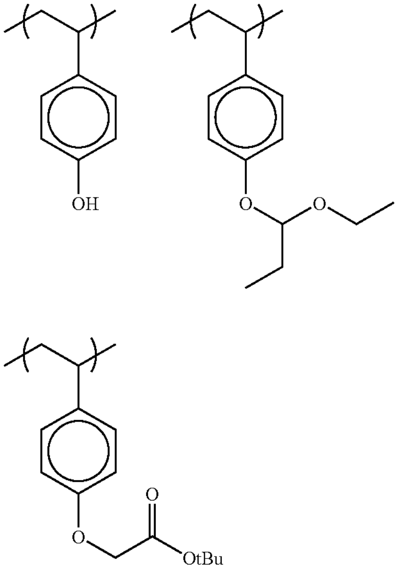

(R-4)

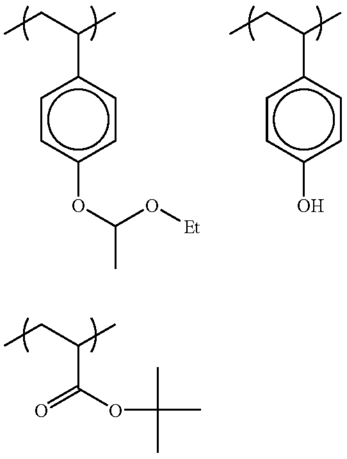

(R-5)

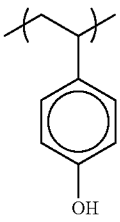

-continued
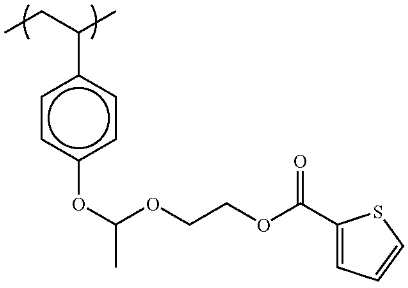
(R-6)
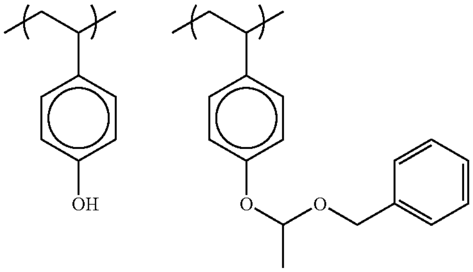
(R-7)
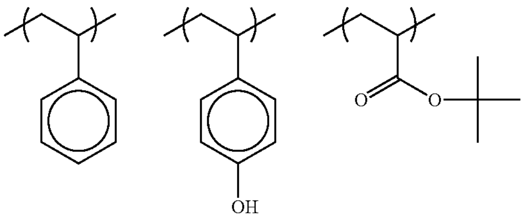
(R-8)
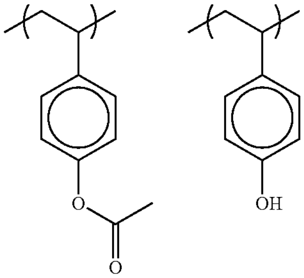
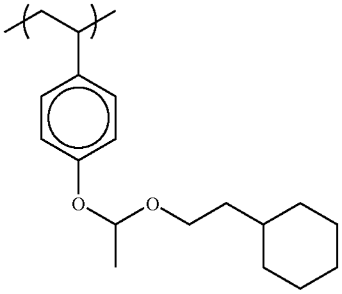
-continued
(R-9)
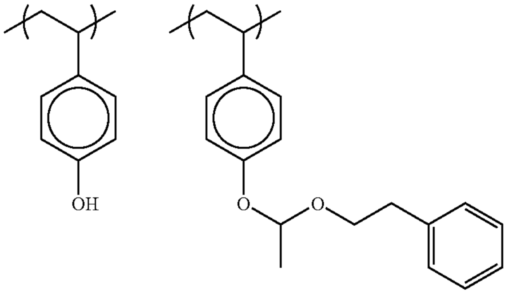
(R-10)
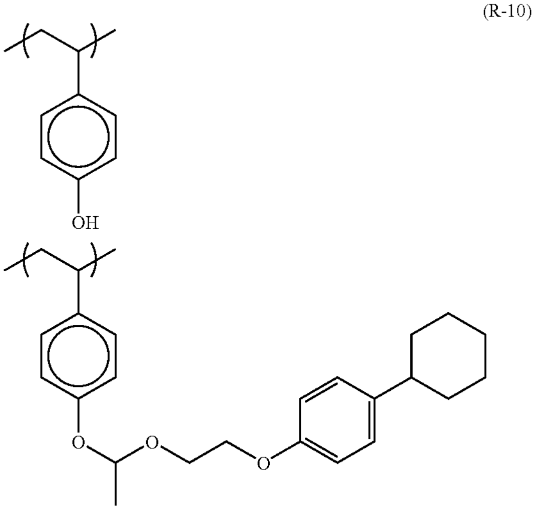
(R-11)
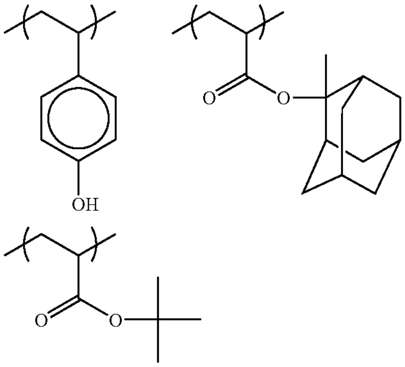
(R-12)
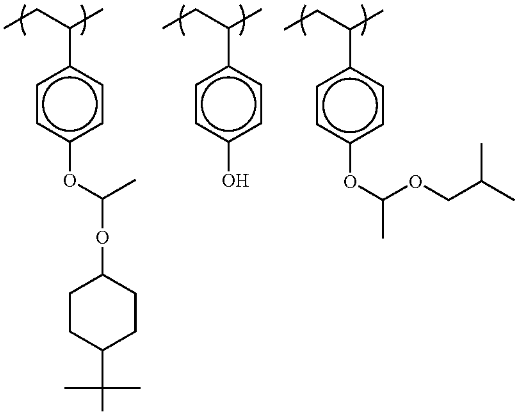

-continued

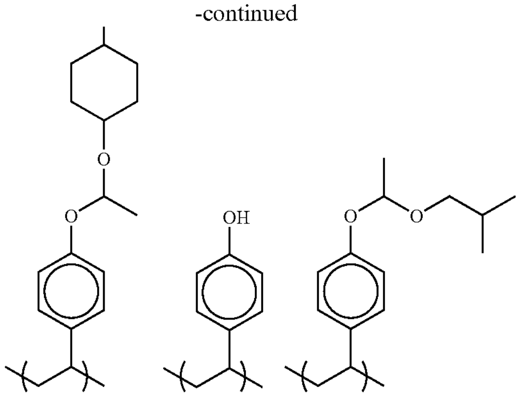

(R-13)

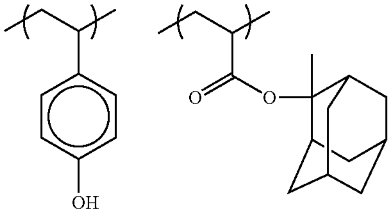

(R-14)

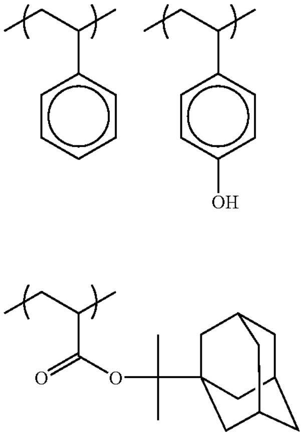

(R-15)

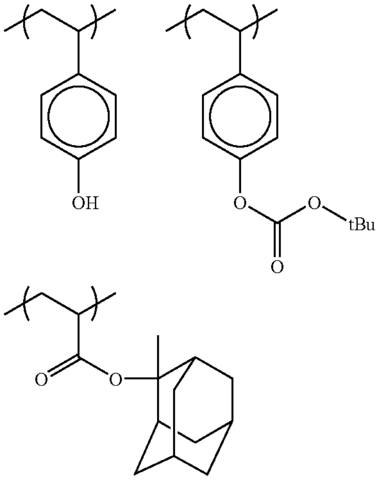

-continued (R-16)

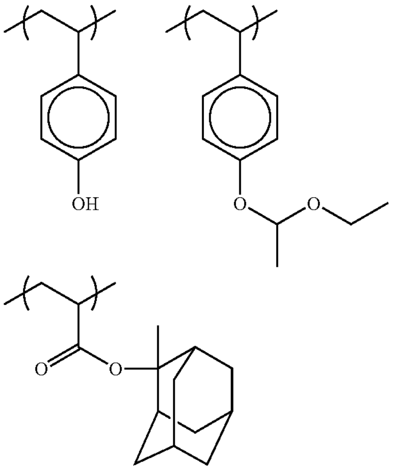

(R-17)

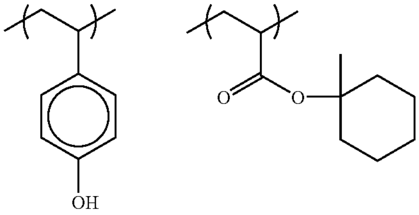

(R-18)

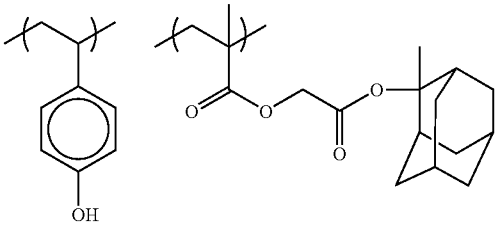

In specific examples above, tBu indicates a tert-butyl group.

The content of the group capable of decomposing under the action of an acid is expressed by B/(B+S) using the number (B) of acid-decomposable groups in the resin and the number (S) of alkali-soluble groups not protected by a group which desorbs by the effect of an acid. The content is preferably from 0.01 to 0.7, more preferably from 0.05 to 0.50, still more preferably from 0.05 to 0.40.

In the case of irradiating the positive photosensitive composition of the present invention with ArF excimer laser light, the resin as the component (B) is preferably a resin having a monocyclic or polycyclic alicyclic hydrocarbon structure and decomposing under the action of an acid to increase the solubility in an alkali developer.

The resin having a monocyclic or polycyclic alicyclic hydrocarbon structure and decomposing under the action of an acid to increase the solubility in an alkali developer (hereinafter sometimes referred to as an "alicyclic hydrocarbon-based acid-decomposable resin") is preferably a resin containing at least one repeating unit selected from the group consisting of a repeating unit having an alicyclic hydrocarbon-containing partial structure represented by any one of the following formulae (pI) to (pV) and a repeating unit represented by the following formula (II-AB):

(pI)

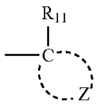

(pII)

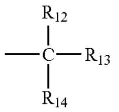

(pIII)

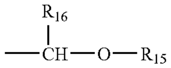

(pIV)

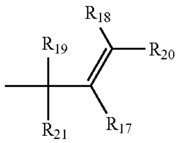

(pV)

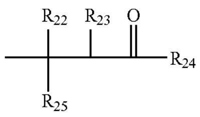

In formulae (pI) to (pV), $R_{11}$ represents a methyl group, an ethyl group, an n-propyl group, an isopropyl group, an n-butyl group, an isobutyl group or a sec-butyl group.

Z represents an atomic group necessary for forming a cycloalkyl group together with the carbon atom.

$R_{12}$ to $R_{16}$ each independently represents a linear or branched alkyl group having a carbon number of 1 to 4 or a cycloalkyl group, provided that at least one of $R_{12}$ to $R_{14}$ or either one of $R_{15}$ and $R_{16}$ represents a cycloalkyl group.

$R_{17}$ to $R_{21}$ each independently represents a hydrogen atom, a linear or branched alkyl group having a carbon number of 1 to 4 or a cycloalkyl group, provided that at least one of $R_{17}$ to $R_{21}$ represents a cycloalkyl group and that either one of $R_{19}$ and $R_{21}$ represents a linear or branched alkyl group having a carbon number of 1 to 4 or a cycloalkyl group.

$R_{22}$ to $R_{25}$ each independently represents a hydrogen atom, a linear or branched alkyl group having a carbon number of 1 to 4 or a cycloalkyl group, provided that at least one of $R_{22}$ to $R_{25}$ represents a cycloalkyl group. $R_{23}$ and $R_{24}$ may combine with each other to form a ring.

(II-AB)

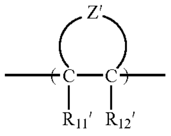

In formula (II-AB), $R_{11}'$ and $R_{12}'$ each independently represents a hydrogen atom, a cyano group, a halogen atom or an alkyl group.

Z' represents an atomic group for forming an alicyclic structure containing two bonded carbon atoms (C—C).

Formula (II-AB) is preferably the following formula (II-AB1) or (II-AB2):

(II-AB1)

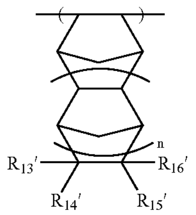

(II-AB2)

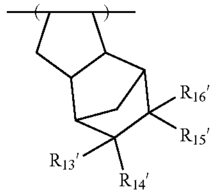

In formulae (II-AB1) and (II-AB2), $R_{13}'$ to $R_{16}'$ each independently represents a hydrogen atom, a halogen atom, a cyano group, —COOH, —COORS, a group capable of decomposing under the action of an acid, —C(=O)—X-A'-$R_{17}'$, an alkyl group or a cycloalkyl group, and at least two members out of $R_{13}'$ to $R_{16}'$ may combine to form a ring.

$R_5$ represents an alkyl group, a cycloalkyl group or a group having a lactone structure.

X represents an oxygen atom, a sulfur atom, —NH—, —$NHSO_2$— or —$NHSO_2NH$—.

A' represents a single bond or a divalent linking group.

$R_{17}'$ represents —COOH, —$COOR_5$, —CN, a hydroxyl group, an alkoxy group, —CO—NH—$R_6$, —CO—NH—$SO_2$—$R_6$ or a group having a lactone structure.

$R_6$ represents an alkyl group or a cycloalkyl group.

n represents 0 or 1.

In formulae (pI) to (pV), the linear or branched alkyl group having a carbon number of 1 to 4 of $R_{12}$ to $R_{25}$ includes a methyl group and an ethyl group.

The cycloalkyl group of $R_{12}$ to $R_{25}$ and the cycloalkyl group formed by Z together with the carbon atom may be monocyclic or polycyclic. Specific examples thereof include a group having a carbon number of 5 or more and having a monocyclo, bicyclo, tricyclo or tetracyclo structure or the like. The carbon number thereof is preferably from 6 to 30, more preferably from 7 to 25.

Preferred examples of the cycloalkyl group include an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. Among these, more preferred are an adamantyl group, a norbornyl group, a cyclohexyl group, a cyclopentyl group, a tetracyclododecanyl group and a tricyclodecanyl group.

Examples of the substituent which the alkyl group and cycloalkyl group each may further have include an alkyl group (having a carbon number of 1 to 4), a halogen atom, a hydroxyl group, an alkoxy group (having a carbon number of 1 to 4), a carboxyl group and an alkoxycarbonyl group (having a carbon number of 2 to 6). Examples of the substituent which these alkyl group, alkoxy group, alkoxycarbonyl group and the like each may further have include a hydroxyl group, a halogen atom and an alkoxy group.

The structures represented by formulae (pI) to (pV) each can be used for the protection of an alkali-soluble group in the resin. Examples of the alkali-soluble group include various groups known in this technical field.

Specific examples thereof include a structure where the hydrogen atom of a carboxylic acid group, a sulfonic acid group, a phenol group or a thiol group is replaced by the structure represented by any one of formulae (pI) to (pV). Among these, preferred is a structure where the hydrogen atom of a carboxylic acid group or a sulfonic acid group is replaced by the structure represented by any one of formulae (pI) to (pV).

The repeating unit having an alkali-soluble group protected by the structure represented by any one of formulae (pI) to (pV) is preferably a repeating unit represented by the following formula (PA):

(PA)

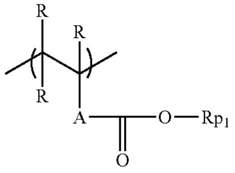

In the formula, R represents a hydrogen atom, a halogen atom or a linear or branched alkyl group having a carbon number of 1 to 4, and the plurality of R's may be the same or different.

A represents a single bond, or a sole group or a combination of two or more groups selected from the group consisting of an alkylene group, an ether group, a thioether group, a carbonyl group, an ester group, an amido group, a sulfonamido group, a urethane group and a urea group. A is preferably a single bond or —COO—$CH_2$—.

$Rp_1$ represents any one group of formulae (pI) to (pV).

The repeating unit represented by formula (PA) is most preferably a repeating unit comprising a 2-alkyl-2-adamantyl (meth)acrylate or a dialkyl(1-adamantyl)methyl (meth)acrylate.

Specific examples of the repeating unit represented by formula (PA) are set forth below, but the present invention is not limited thereto.

In the formulae, Rx represents H, $CH_3$, $CF_3$ or $CH_2OH$, and Rxa and Rxb each independently represents an alkyl group having a carbon number of 1 to 4.

1

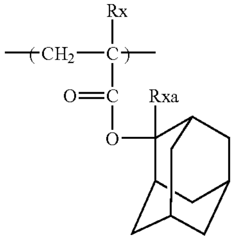

-continued

2

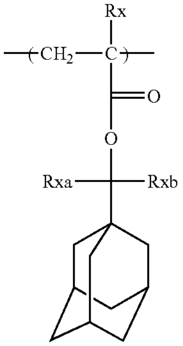

3

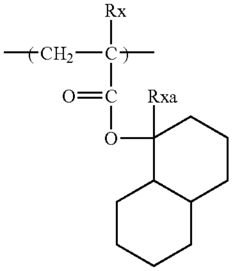

4

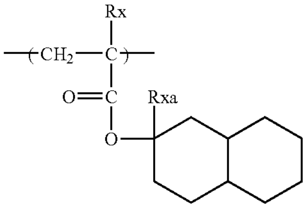

5

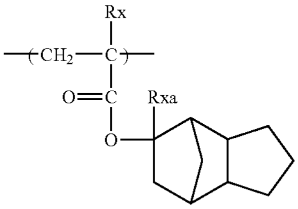

6

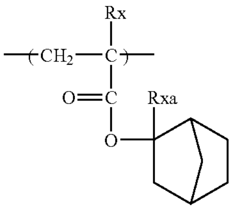

7

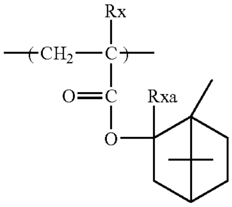

-continued
8
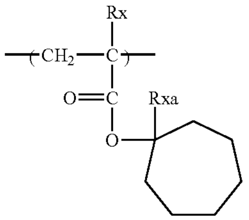
9
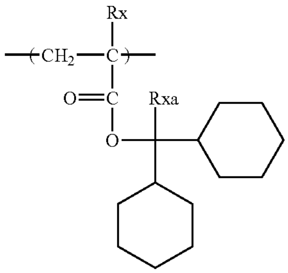
10
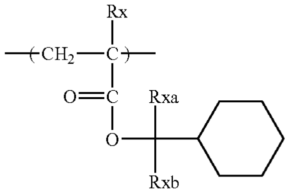
11
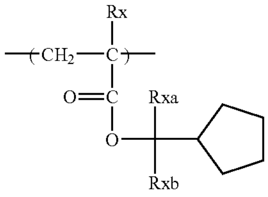
12
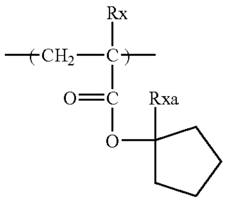
13
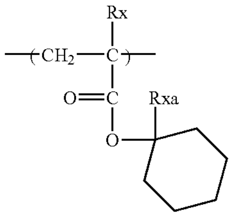
14
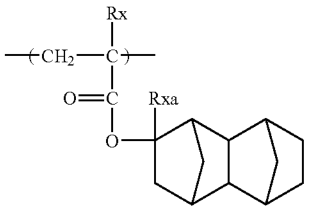
-continued
15
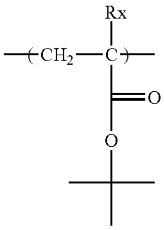
16
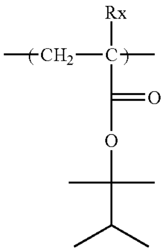
17
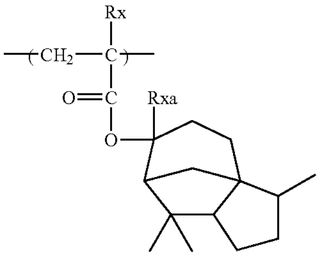
18
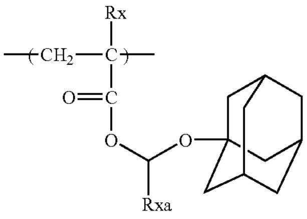
19
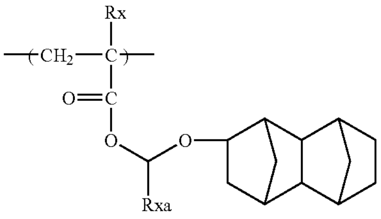
20
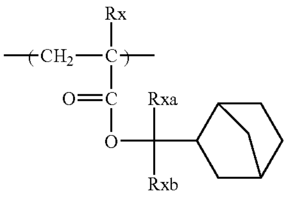

-continued

21

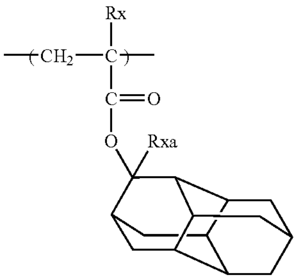

22

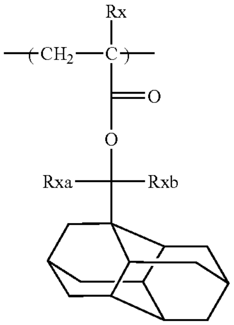

23

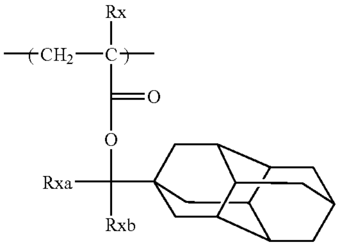

24

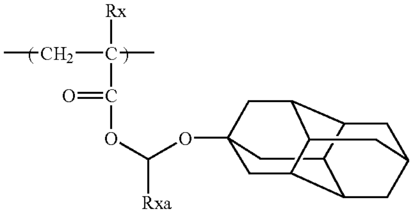

25

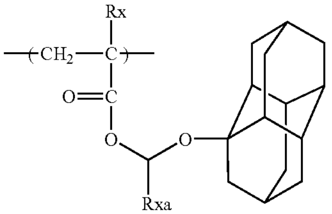

26

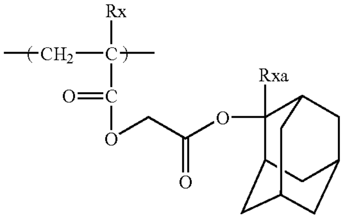

-continued

27

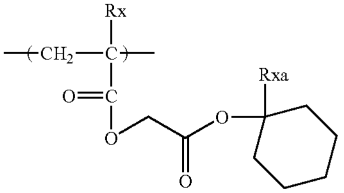

28

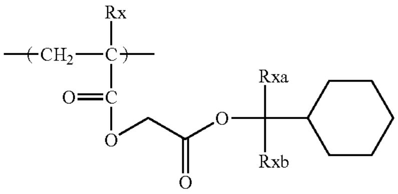

29

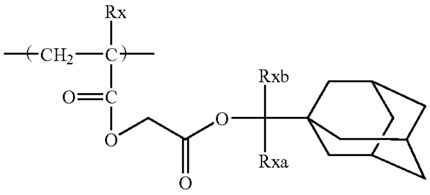

Examples of the halogen atom of $R_{11}$' and $R_{12}$' in formula (II-AB) include a chlorine atom, a bromine atom, a fluorine atom and an iodine atom.

The alkyl group of $R_{11}$' and $R_{12}$' includes a linear or branched alkyl group having a carbon number of 1 to 10.

The atomic group of Z' for forming an alicyclic structure is an atomic group for forming a repeating unit comprising an alicyclic hydrocarbon which may have a substituent. In particular, an atomic group for forming a crosslinked alicyclic structure to form a crosslinked alicyclic hydrocarbon repeating unit is preferred.

Examples of the skeleton of the alicyclic hydrocarbon formed are the same as those of the alicyclic hydrocarbon group of $R_{12}$ to $R_{25}$ in formulae (pI) to (pV).

The skeleton of the alicyclic hydrocarbon may have a substituent, and examples of the substituent include $R_{13}$' to $R_{16}$' in formulae (II-AB1) and (II-AB2).

In the alicyclic hydrocarbon-based acid-decomposable resin for use in the present invention, the group capable of decomposing under the action of an acid may be contained in at least one repeating unit out of the repeating unit having an alicyclic hydrocarbon-containing partial structure represented by any one of formulae (pI) to (pV), the repeating unit represented by formula (II-AB), and the repeating unit comprising a copolymerization component described later.

As for the acid-decomposable repeating unit, one species may be used but two or more kinds of acid-decomposable repeating units differing in the carbon number of the group which splits off by the effect of an acid are preferably used in combination. By virtue of this, the resolving power and the exposure latitude can be well-balanced.

Various substituents $R_{13}$' to $R_{16}$' in formulae (II-AB1) and (II-AB2) may become the substituents of an atomic group for forming an alicyclic hydrocarbon structure in formula (II-AB) or an atomic group Z for forming a crosslinked alicyclic hydrocarbon structure.

Specific examples of the repeating units represented by formulae (II-AB1) and (II-AB2) are set forth below, but the present invention is not limited to these specific examples.

[II-1]
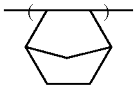
[II-2]
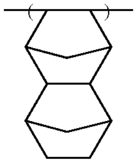
[II-3]
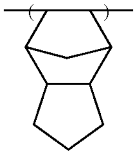
[II-4]
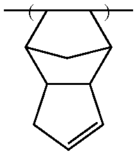
[II-5]
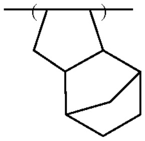
[II-6]
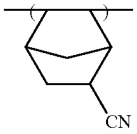
[II-7]
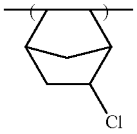
[II-8]
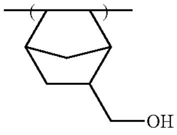
[II-9]
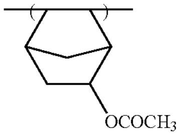
[II-10]
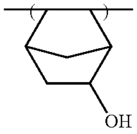
-continued
[II-11]
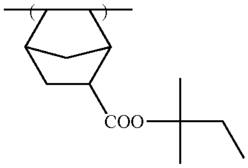
[II-12]
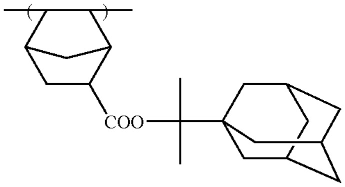
[II-13]
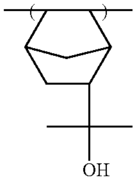
[II-14]
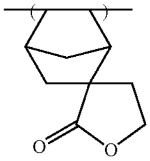
[II-15]
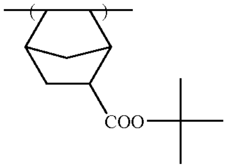
[II-16]
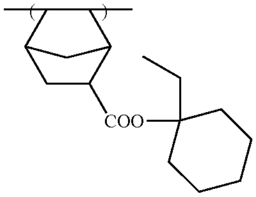
[II-17]
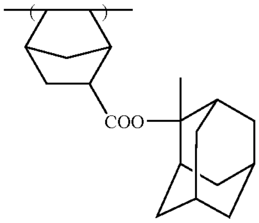
[II-18]
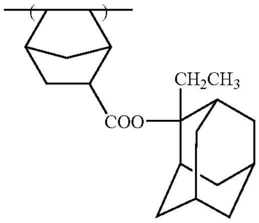

-continued
[II-19]
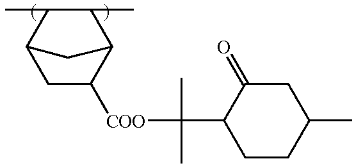
[II-20]
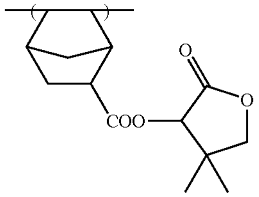
[II-21]
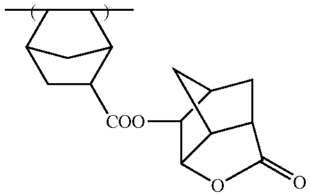
[II-22]
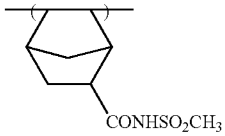
[II-23]
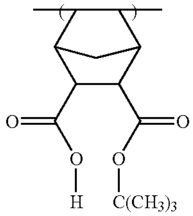
[II-24]
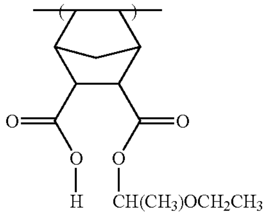
[II-25]
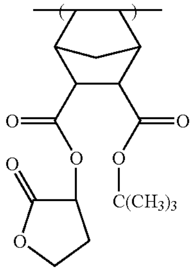
-continued
[II-26]
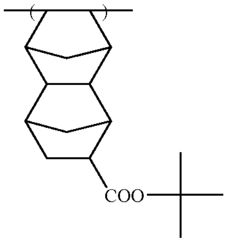
[II-27]
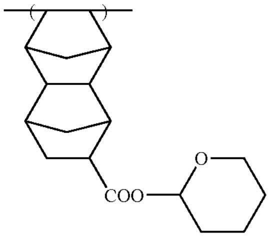
[II-28]
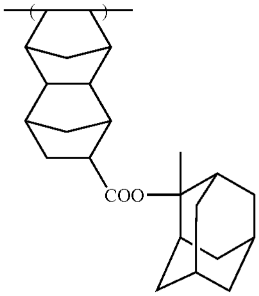
[II-29]
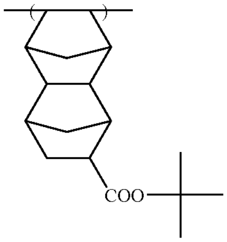
[II-30]
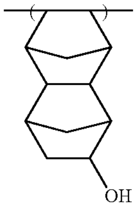
[II-31]
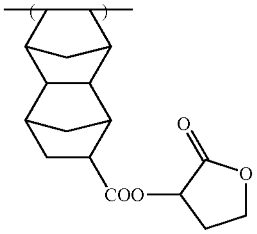

-continued

[II-32]

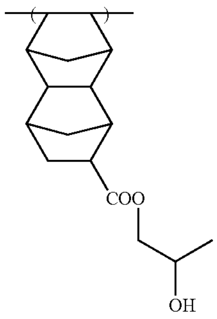

The alicyclic hydrocarbon-based acid-decomposable resin for use in the present invention preferably has a lactone group. As for the lactone group, any group may be used as long as it has a lactone structure, but a group having a 5- to 7-membered ring lactone structure is preferred. The 5- to 7-membered ring lactone structure is preferably condensed with another ring structure in the form of forming a polycyclic or spiro structure. A repeating unit containing a group having a lactone structure represented by any one of the following formulae (LCI-1) to (LCI-16) is preferably contained. The group having a lactone structure may be bonded directly to the main chain. Among these lactone structures, preferred are (LC1-1), (LC1-4), (LC1-5), (LC1-6), (LC1-13) and (LC1-14). By virtue of using a specific lactone structure, the line edge roughness and development defect are improved.

LC1-1

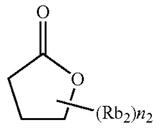

LC1-2

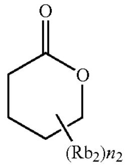

LC1-3

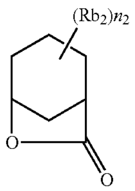

LC1-4

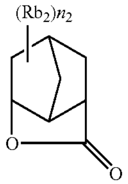

-continued

LC1-5

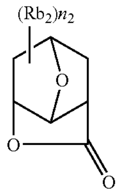

LC1-6

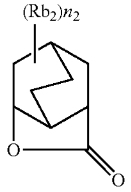

LC1-7

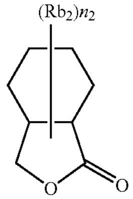

LC1-8

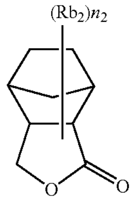

LC1-9

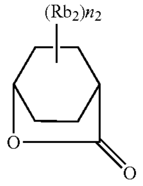

LC-10

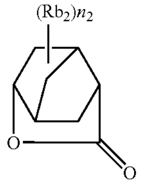

LC1-11

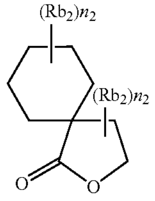

LC1-12

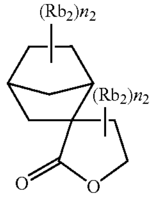

-continued

LC1-13

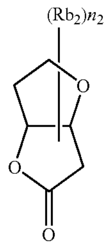

LC1-14

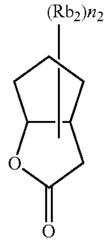

LC1-15

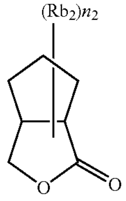

LC1-16

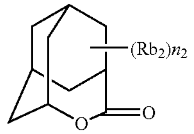

The lactone structure moiety may or may not have a substituent ($Rb_2$). Preferred examples of the substituent ($Rb_2$) include an alkyl group having a carbon number of 1 to 8, a cycloalkyl group having a carbon number of 4 to 7, an alkoxy group having a carbon number of 1 to 8, an alkoxycarbonyl group having a carbon number of 1 to 8, a carboxyl group, a halogen atom, a hydroxyl group, a cyano group and an acid-decomposable group. $n_2$ represents an integer of 0 to 4. When $n_2$ is an integer of 2 or more, the plurality of substituents ($Rb_2$) may be the same or different and also, the plurality of substituents ($Rb_2$) may combine with each other to form a ring.

Examples of the repeating unit containing a group having a lactone structure represented by any one of formulae (LC1-1) to (LC1-16) include a repeating unit where at least one of $R_{13}'$ to $R_{16}'$ in formula (II-AB1) or (II-AB2) has a group represented by any one of formulae (LC1-1) to (LC1-16) (for example, $R_5$ of —$COOR_5$ is a group represented by any one of formulae (LC1-1) to (LC1-16)), and a repeating unit represented by the following formula (AI):

(AI)

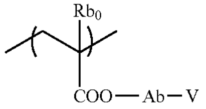

In formula (AI), $Rb_0$ represents a hydrogen atom, a halogen atom or an alkyl group having a carbon number of 1 to 4.

Preferred examples of the substituent which the alkyl group of $Rb_0$ may have include a hydroxyl group and a halogen atom.

The halogen atom of $Rb_0$ includes a fluorine atom, a chlorine atom, a bromine atom and an iodine atom.

$Rb_0$ is preferably a hydrogen atom or a methyl group.

Ab represents a single bond, an alkylene group, a divalent linking group having a monocyclic or polycyclic alicyclic hydrocarbon structure, an ether group, an ester group, a carbonyl group, a carboxyl group, or a divalent group comprising a combination thereof.

Ab is preferably a single bond or a linking group represented by $-Ab_1-CO_2-$. $Ab_1$ is a linear or branched alkylene group or a monocyclic or polycyclic cycloalkylene group, preferably a methylene group, an ethylene group, a cyclohexylene group, an adamantyl group or a norbornyl group.

V represents a group represented by any one of formulae (LC1-1) to (LC1-16).

The repeating unit having a lactone structure usually has an optical isomer, but any optical isomer may be used. One optical isomer may be used alone or a mixture of a plurality of optical isomers may be used. In the case of mainly using one optical isomer, the optical purity (ee) thereof is preferably 90 or more, more preferably 95 or more.

The content of the repeating unit having a lactone structure is preferably from 15 to 60 mol %, more preferably from 20 to 50 mol %, still more preferably from 30 to 50 mol %, based on all repeating units in the polymer.

Preferred examples of the repeating unit having a lactone structure include the following repeating units. By selecting an optimal lactone structure, good performance is obtained in terms of pattern profile and defocus latitude depended on line pitch.

(In the formulae, Rx is H, $CH_3$, $CH_2OH$ or $CF_3$.)

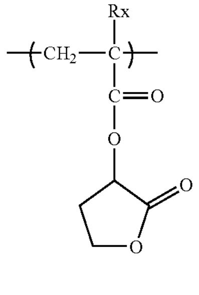

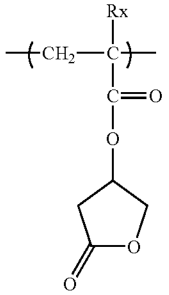

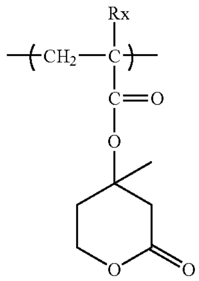

-continued

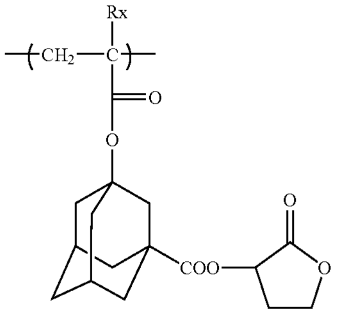

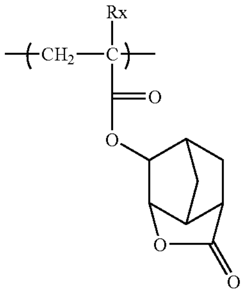

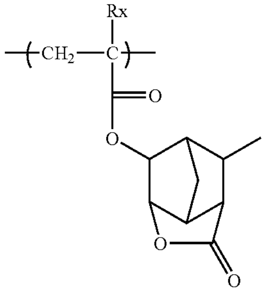

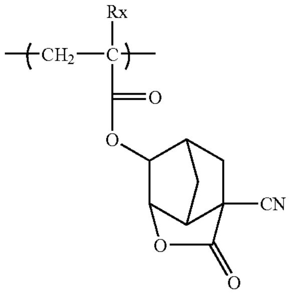

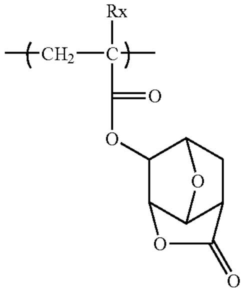

-continued

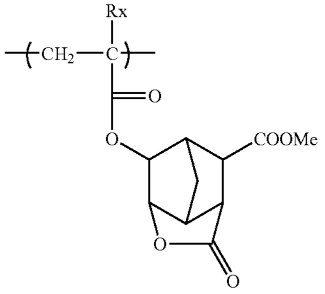

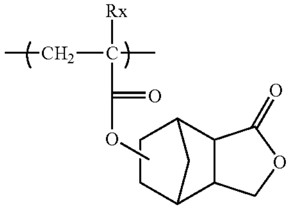

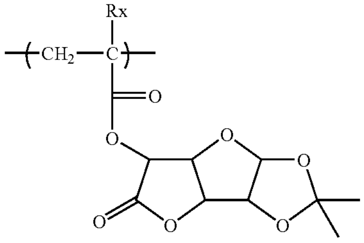

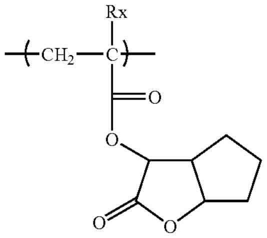

The alicyclic hydrocarbon-based acid-decomposable resin for use in the present invention preferably contains a repeating unit having an alicyclic hydrocarbon structure substituted by a polar group. By virtue of this repeating unit, the adhesion to substrate and the affinity for developer are enhanced. The alicyclic hydrocarbon structure of the alicyclic hydrocarbon structure substituted by a polar group is preferably an adamantyl group, a diamantyl group or a norbornane group. The polar group is preferably a hydroxyl group or a cyano group. The alicyclic hydrocarbon structure substituted by a polar group is preferably a partial structure represented by any one of the following formulae (VIIa) to (VIId):

(VIIa)

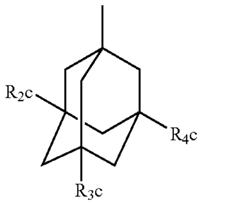

-continued (VIIb)

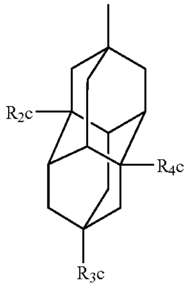

(VIIc)

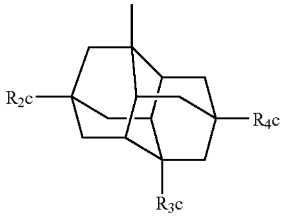

(VIId)

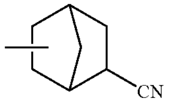

In formulae (VIIa) to (VIIc), $R_{2c}$ to $R_{4c}$ each independently represents a hydrogen atom, a hydroxyl group or a cyano group, provided that at least one of $R_{2c}$ to $R_{4c}$ represents a hydroxyl group or a cyano group. A structure where one or two members out of $R_{2c}$ to $R_{4c}$ are a hydroxyl group with the remaining being a hydrogen atom is preferred. In formula (VIIa), it is more preferred that two members out of $R_{2c}$ to $R_{4c}$ are a hydroxyl group and the remaining is a hydrogen atom.

The repeating unit having a group represented by any one of formulae (VIIa) to (VIId) includes a repeating unit where at least one of $R_{13}'$ to $R_{16}'$ in formula (II-AB1) or (II-AB2) has a group represented by any one of formulae (VIIa) to (VIId) (for example, $R_5$ of —$COOR_5$ is a group represented by any one of formulae (VIIa) to (VIId)), and repeating units represented by the following formulae (AIIa) to (AIId):

(AIIa)

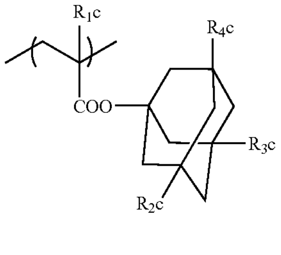

-continued (AIIb)

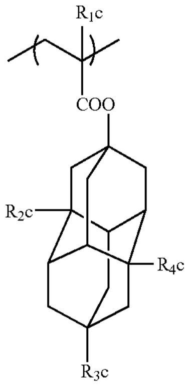

(AIIc)

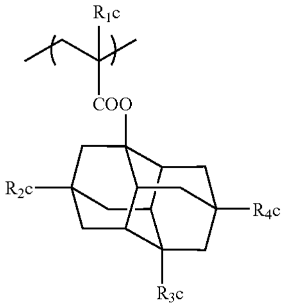

(AIId)

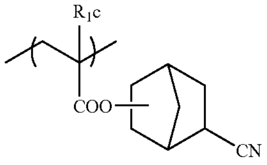

In formulae (AIIa) to (AIId), $R_{1c}$ represents a hydrogen atom, a methyl group, a trifluoromethyl group or a hydroxymethyl group.

$R_{2c}$ to $R_{4c}$ have the same meanings as $R_{2c}$ to $R_{4c}$ in formulae (VIIa) to (VIIc).

The content of the repeating unit having an alicyclic hydrocarbon structure substituted by a polar group is preferably from 5 to 40 mol %, more preferably from 5 to 30 mol %, still more preferably from 10 to 25 mol %, based on all repeating units in the polymer.

Specific examples of the repeating units represented by formulae (AIIa) to (AIId) are set forth below, but the present invention is not limited thereto

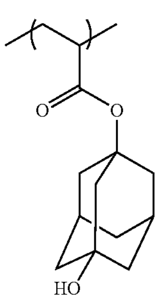 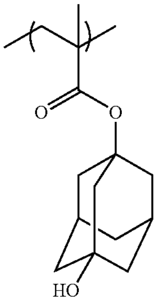

-continued

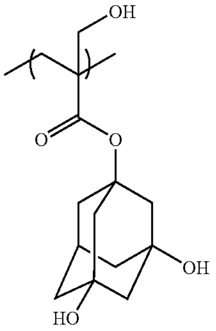

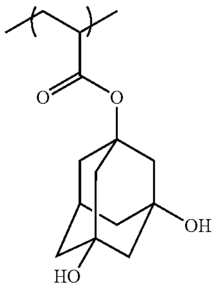

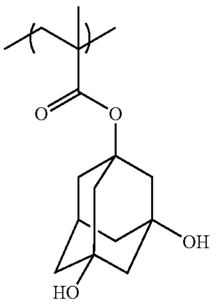

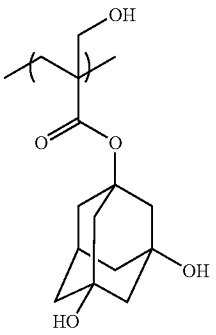

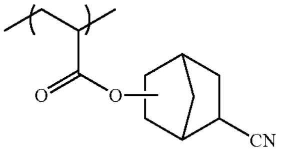

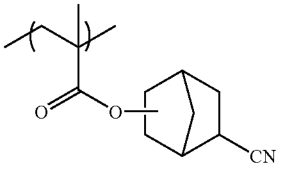

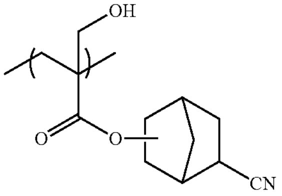

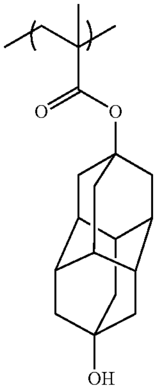

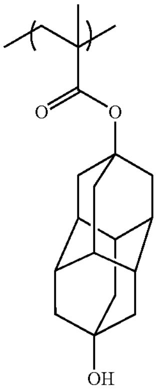

-continued

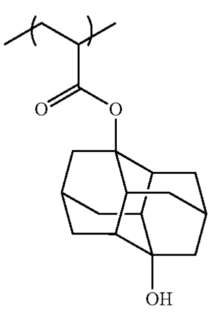

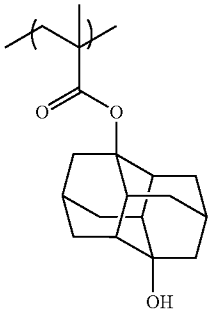

The alicyclic hydrocarbon-based acid-decomposable resin for use in the present invention may contain a repeating unit represented by the following formula (VIII):

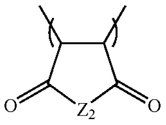

(VIII)

In formula (VIII), $Z_2$ represents —O— or —N($R_{41}$)—. $R_{41}$ represents a hydrogen atom, a hydroxyl group, an alkyl group or —$OSO_2$—$R_{42}$. $R_{42}$ represents an alkyl group, a cycloalkyl group or a camphor residue. The alkyl group of $R_{41}$ and $R_{42}$ may be substituted by a halogen atom (preferably fluorine atom) or the like.

Specific examples of the repeating unit represented by formula (VIII) are set forth below, but the present invention is not limited thereto.

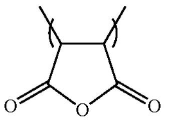

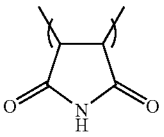

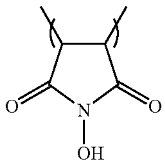

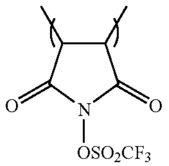

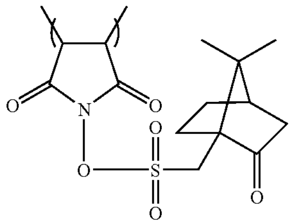

The alicyclic hydrocarbon-based acid-decomposable resin for use in the present invention preferably contains a repeating unit having an alkali-soluble group. The alkali-soluble group includes a carboxyl group, a sulfonamide group, a sulfonylimide group, a bis-sulfonylimide group and an aliphatic alcohol substituted with an electron-withdrawing group at the α-position (preferably a structure represented by the following formula (F1)). It is more preferred to contain a carboxyl group-containing repeating unit.

(F1)

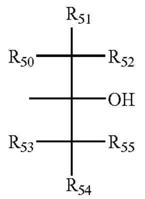

In formula (F1), $R_{50}$ to $R_{55}$ each independently represents a hydrogen atom, a fluorine atom or an alkyl group, provided that at least one of $R_{50}$ to $R_{55}$ is a fluorine atom or an alkyl group with at least one hydrogen atom being substituted by a fluorine atom. It is preferred that $R_{50}$ to $R_{55}$ all are a fluorine atom.

By virtue of containing a repeating unit having an alkali-soluble group, the resolution increases in the usage of forming contact holes. As for the repeating unit having an alkali-soluble group, a repeating unit where an alkali-soluble group is directly bonded to the resin main chain, such as repeating unit by an acrylic acid or a methacrylic acid, a repeating unit where an alkali-soluble group is bonded to the resin main chain through a linking group, and a repeating unit where an alkali-soluble group is introduced into the terminal of the polymer chain by using a polymerization initiator or chain transfer agent having an alkali-soluble group at the polymerization, all are preferred. The linking group may have a monocyclic or polycyclic hydrocarbon structure. A repeating unit by an acrylic acid or a methacrylic acid is most preferred.

The content of the repeating unit having an alkali-soluble group is preferably from 1 to 20 mol %, more preferably from 3 to 15 mol %, still more preferably from 5 to 10 mol %, based on all repeating units in the polymer.

Specific examples of the repeating unit having an alkali-soluble group are set forth below, but the present invention is not limited thereto.

(In the formulae, Rx represents H, $CH_3$, $CF_3$ or $CH_2OH$).

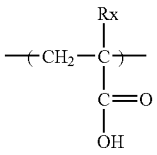

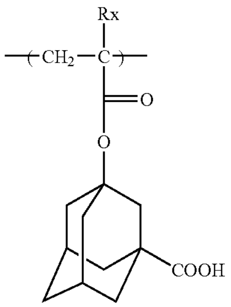

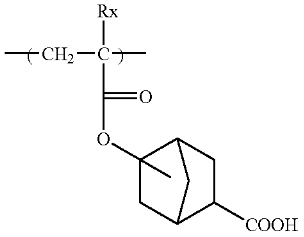

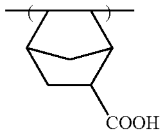

-continued

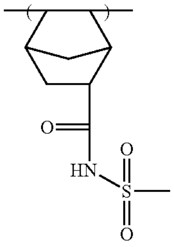

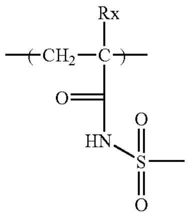

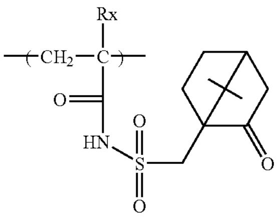

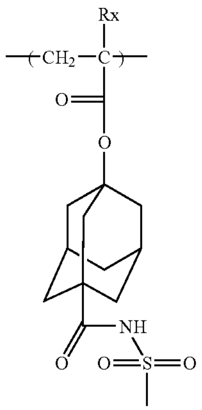

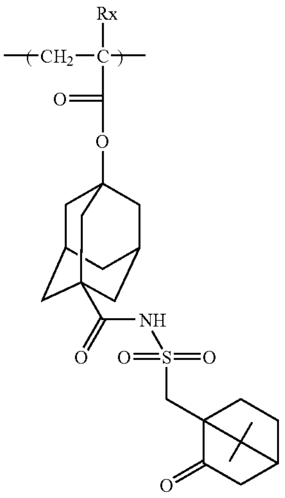

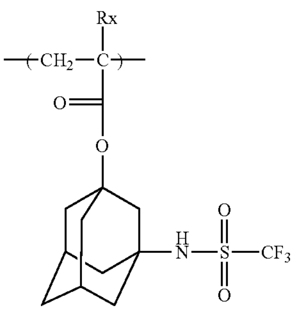

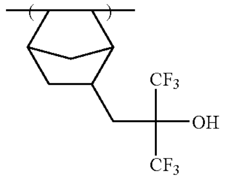

-continued

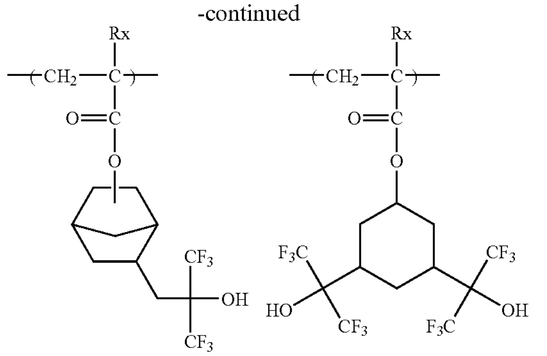

The alicyclic hydrocarbon-based acid-decomposable resin for use in the present invention may further contain a repeating unit having an alicyclic hydrocarbon structure and not exhibiting acid decomposability. By containing such a repeating unit, the dissolving out of low molecular components from the resist film to the immersion liquid at the immersion exposure can be reduced. Examples of this repeating unit include 1-adamantyl (meth)acrylate, tricyclodecanyl (meth) acrylate and cyclohexyl (meth)acrylate.

The alicyclic hydrocarbon-based acid-decomposable resin for use in the present invention may contain, in addition to the above-described repeating units, various repeating structural units for the purpose of controlling dry etching resistance, suitability for standard developer, adhesion to substrate, resist profile and properties generally required of the resist, such as resolving power, heat resistance and sensitivity.

Other than these, an addition-polymerizable unsaturated compound copolymerizable with the monomers corresponding to the above-described various repeating structural units may be copolymerized.

In the alicyclic hydrocarbon-based acid-decomposable resin, the molar ratio of respective repeating structural units contained is appropriately determined to control the dry etching resistance of resist, suitability for standard developer, adhesion to substrate, resist profile and performances generally required of the resist, such as resolving power, heat resistance and sensitivity.

In the alicyclic hydrocarbon-based acid-decomposable resin, the content of the repeating unit having an acid-decomposable group is preferably from 10 to 60 mol %, more preferably from 20 to 50 mol %, still more preferably from 25 to 40 mol %, based on all repeating structural units.

In the alicyclic hydrocarbon-based acid-decomposable resin, the content of the repeating unit having an alicyclic hydrocarbon-containing partial structure represented by any one of formulae (pI) to (pV) is preferably from 20 to 70 mol %, more preferably from 20 to 50 mol %, still more preferably from 25 to 40 mol %, based on all repeating structural units.

In the alicyclic hydrocarbon-based acid-decomposable resin, the content of the repeating unit represented by formula (II-AB) is preferably from 10 to 60 mol %, more preferably from 15 to 55 mol %, still more preferably from 20 to 50 mol %, based on all repeating structural units.

In the case of using the photosensitive composition of the present invention for exposure with ArF, the resin preferably has no aromatic group in view of transparency to ArF light.

The alicyclic hydrocarbon-based acid-decomposable resin for use in the present invention is preferably a resin where all repeating units are composed of a (meth)acrylate-based repeating unit. In this case, the repeating units may be all a methacrylate-based repeating unit, all an acrylate-based repeating unit, or a mixture of methacrylate-based repeating unit/acrylate-based repeating unit, but the content of the acrylate-based repeating unit is preferably 50 mol % or less based on all repeating units. The alicyclic hydrocarbon-based acid-decomposable resin is more preferably a copolymerization polymer comprising from 20 to 50% of the repeating unit having an alicyclic hydrocarbon-containing partial structure represented by any one of formulae (pI) to (pV), from 20 to 50% of the repeating unit having a lactone structure and from 5 to 30% of the repeating unit having an alicyclic hydrocarbon structure substituted by a polar group, or a copolymerization polymer additionally comprising from 0 to 20% of other repeating units.

In particular, the resin is preferably a resin comprising from 20 to 50 mol % of the repeating unit having an acid-decomposable group represented by any one of the following formulae (ARA-1) to (ARA-5), from 20 to 50 mol % of the repeating unit having a lactone group represented by any one of the following formulae (ARL-1) to (ARL-7), and from 5 to 30 mol % of the repeating unit having an alicyclic hydrocarbon structure substituted by a polar group, represented by any one of the following formulae (ARH-1) to (ARH-3), or a resin further comprising from 5 to 20 mol % of the repeating unit containing a carboxyl group or a structure represented by formula (F1) and the repeating unit having an alicyclic hydrocarbon structure and not exhibiting acid decomposability.

(In the formulae, $Rxy_1$ represents a hydrogen atom or a methyl group, and $Rxa_1$ and $Rxb_1$ each independently represents a methyl group or an ethyl group.)

ARA-1

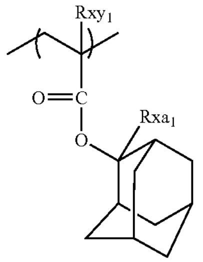

ARA-2

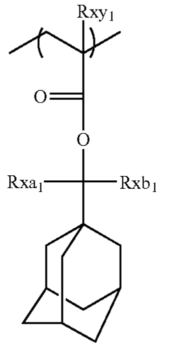

ARA-3

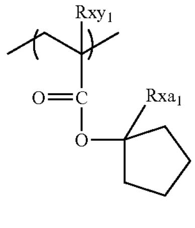

-continued
ARA-4
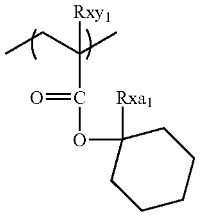
ARA-5
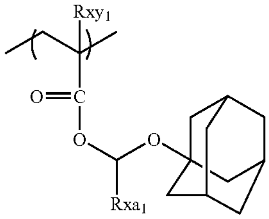
ARL-1
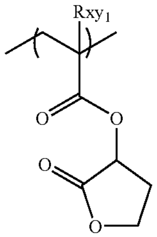
ARL-2
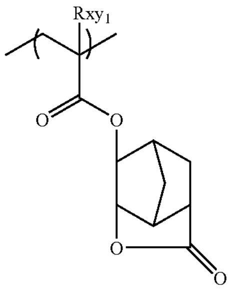
ARL-3
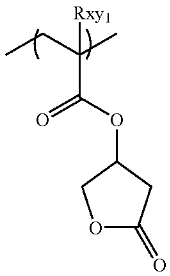
ARL-4
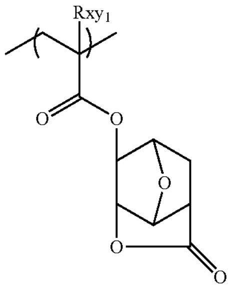
-continued
ARL-5
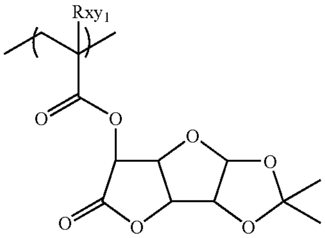
ARL-6
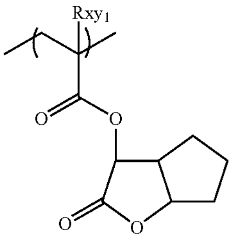
ARL-7
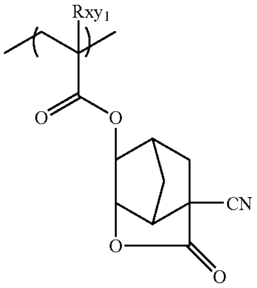
ARH-1
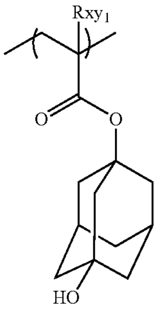
ARH-2
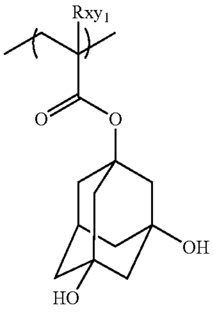
ARH-3
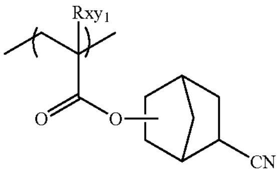

In the case of using the photosensitive composition of the present invention for the upper resist layer of a multilayer resist, the resin as the component (B) preferably has a silicon atom.

As for the resin having a silicon atom and capable of decomposing under the action of an acid to increase the solubility in an alkali developer, a resin having a silicon atom at least in either the main chain or the side chain can be used. Examples of the resin having a siloxane structure in the side chain of the resin include a copolymer of an olefin-based monomer having a silicon atom in the side chain and a (meth) acrylic acid-based monomer having a maleic anhydride and an acid-decomposable group in the side chain.

The resin having a silicon atom is preferably a resin having a trialkylsilyl structure or a monocyclic or polycyclic siloxane structure, more preferably a resin containing a repeating unit having a structure represented by any one of the following formulae (SS-1) to (SS-4), still more preferably a resin containing a (meth)acrylic acid ester-based, vinyl-based or allyl-based repeating unit having a structure represented by any one of formulae (SS-1) to (SS-4).

SS-1

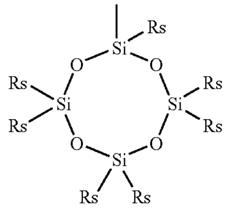

SS-2

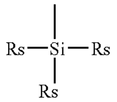

SS-3

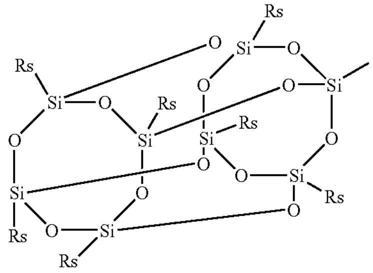

SS-4

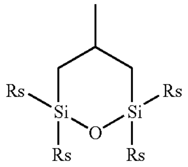

In formulae (SS-1) to (SS-4), Rs represents an alkyl group having a carbon number of 1 to 5 and is preferably a methyl group or an ethyl group.

The resin having a silicon atom is preferably a resin containing two or more different silicon atom-containing repeating units, more preferably a resin containing both (Sa) a repeating unit having from 1 to 4 silicon atoms and (Sb) a repeating unit having from 5 to 10 silicon atoms, still more preferably a resin containing at least one repeating unit having a structure represented by any one of formulae (SS-1) to (SS-3) and a repeating unit having a structure represented by formula (SS-4).

Specific preferred examples of the silicon atom-containing resin include the following (SI-1) to (SI-5), but the present invention is not limited thereto.

(SI-1)

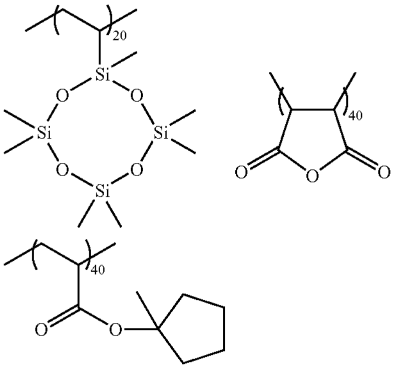

(SI-2)

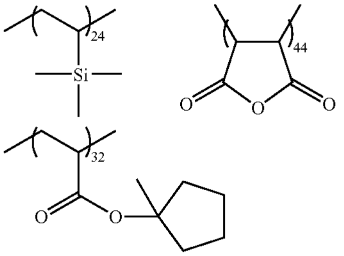

(SI-3)

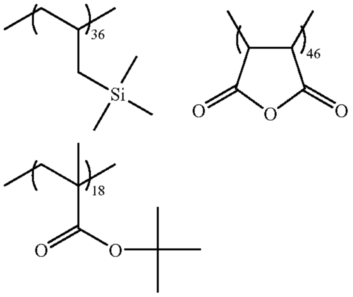

(SI-4)

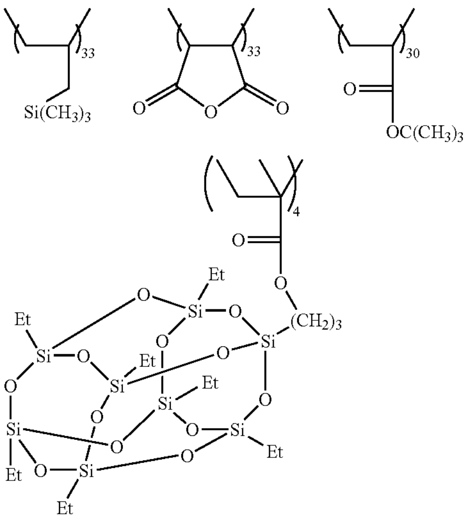

-continued (SI-5)

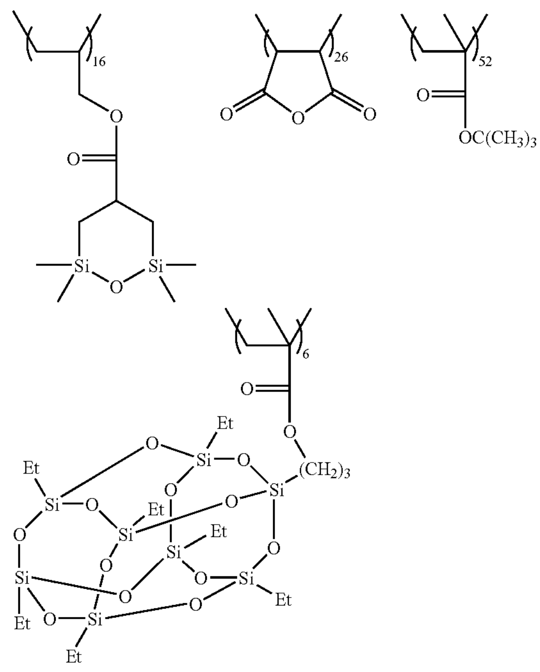

The resin as the component (B) can be synthesized by an ordinary method (for example, radical polymerization). Examples of the synthesis method in general include a batch polymerization method of dissolving the monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include tetrahydrofuran, 1,4-dioxane, ethers such as diisopropyl ether, ketones such as methyl ethyl ketone and methyl isobutyl ketone, an ester solvent such as ethyl acetate, an amide solvent such as dimethylformamide and dimethylacetamide, and a solvent capable of dissolving the composition of the present invention, which is described later, such as propylene glycol monomethyl ether acetate, propylene glycol monomethyl ether and cyclohexanone. The polymerization is more preferably performed using the same solvent as the solvent used in the resist composition of the present invention. By the use of this solvent, production of particles during storage can be suppressed.

The polymerization reaction is preferably performed in an inert gas atmosphere such as nitrogen and argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2-azobis(2-methylpropionate). Together with the polymerization initiator, a chain transfer agent such as thiol compound may be used in combination. The initiator is added additionally or in parts, if desired. After the completion of reaction, the reactant is charged into a solvent, and the desired polymer is recovered by a method such as powder or solid recovery. The reaction concentration is from 5 to 50 mass %, preferably from 10 to 30 mass %, and the reaction temperature is usually from 10 to 150° C., preferably from 30 to 120° C., more preferably from 60 to 100° C.

The weight average molecular weight of the resin as the component (B) is preferably from 1,000 to 200,000, more preferably from 3,000 to 20,000, and most preferably from 5,000 to 15,000, in terms of polystyrene as measured by the GPC method. When the weight average molecular weight is from 1,000 to 200,000, deterioration of heat resistance, dry etching resistance and developability can be prevented and at the same time, the film-forming property can be prevented from deteriorating due to increase in the viscosity.

The molecular weight distribution (dispersivity) of the resin as the component (B) is usually from 1 to 5, preferably from 1 to 2, more preferably from 1.3 to 2. As the molecular weight distribution is smaller, the resolution and resist profile are more excellent, the side wall of the resist pattern is smoother, and the performance in terms of roughness is higher.

In the photosensitive composition of the present invention, as regards all resins for use in the present invention, the blending amount in the composition as a whole is preferably from 60 to 99 mass %, more preferably from 80 to 98 mass %, based on the entire solid content.

Also, in the present invention, as for the resin, one kind may be used or a plurality of kinds may be used in combination.

Dissolution controlling compound containing at least one member selected from an alkali-soluble group, a hydrophilic group and an acid-decomposable group and having a molecular weight of 3,000 or less:

In the photosensitive composition of the present invention, a dissolution controlling compound containing at least one member selected from an alkali-soluble group, a hydrophilic group and an acid-decomposable group and having a molecular weight of 3,000 or less (hereinafter sometimes referred to as a "dissolution controlling compound") may be added.

The dissolution controlling compound is preferably a compound containing an alkali-soluble group such as carboxyl group, sulfonylimide group and hydroxyl group substituted with a fluoroalkyl group at the α-position, a compound containing a hydrophilic group such as hydroxyl group, lactone group, cyano group, amide group, pyrrolidone group and sulfonamide group, or a compound containing a group capable of decomposing under the action of an acid to release an alkali-soluble group or a hydrophilic group. The group capable of decomposing under the action of an acid to release an alkali-soluble group or a hydrophilic group is preferably a group in which a carboxyl group or a hydroxyl group is protected by an acid decomposable protective group. As regards the dissolution controlling compound, for the purpose of not decreasing the transparency to light at 220 nm or less, it is preferred to use an aromatic ring-free compound or use an aromatic ring-containing compound in an added amount of 20 wt % or less based on the solid content of the composition.

Preferred examples of the dissolution controlling compound include a carboxylic acid compound having an alicyclic hydrocarbon structure, such as adamantane (di)-carboxylic acid, norbornane carboxylic acid and cholic acid, or a compound obtained by protecting the carboxylic acid with an acid-decomposable protective group; and a polyol such as sugars or a compound obtained by protecting the hydroxyl group thereof with an acid-decomposable group.

The molecular weight of the dissolution controlling compound for use in the present invention is 3,000 or less, preferably from 300 to 3,000, more preferably from 500 to 2,500.

The amount of the dissolution controlling compound added is preferably from 3 to 40 mass %, more preferably from 5 to 20 mass %, based on the solid content of the photosensitive composition.

Specific examples of the dissolution controlling compound are set forth below, but the present invention is not limited thereto.

TE-1

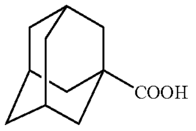

TE-2

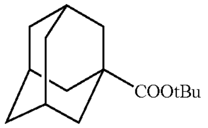

TE-3

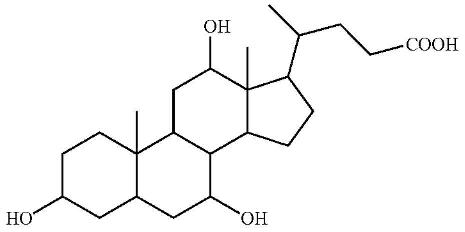

TE-4

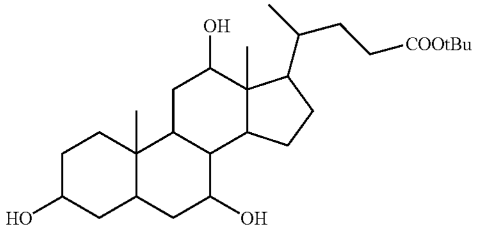

TE-5

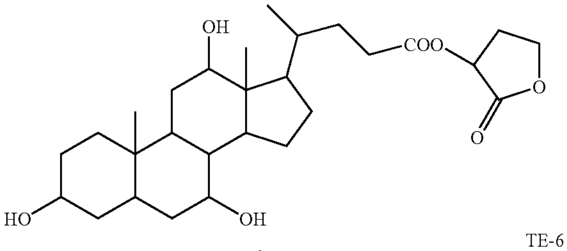

TE-6

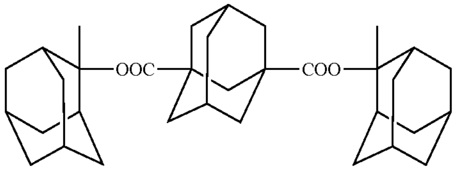

TE-7

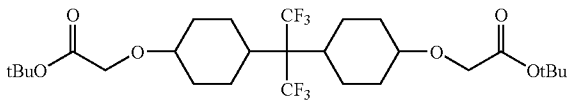

TE-8

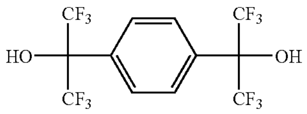

-continued

TE-9

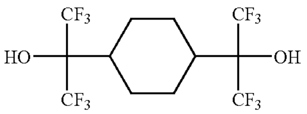

TE-10

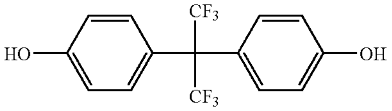

TE-11

$HO—(CH_2)_{12}—OH$

TE-12

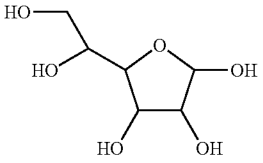

TE-13

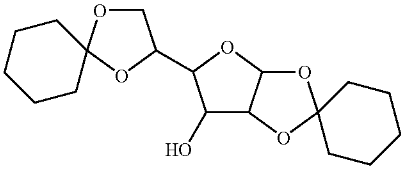

TE-14

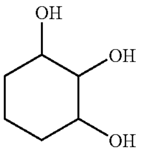

TE-15

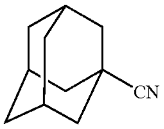

TE-16

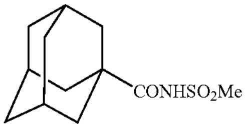

Resin Soluble in an Alkali Developer:

The alkali dissolution rate of the resin soluble in an alkali developer (hereinafter sometimes referred to as an "alkali-soluble resin") for use in the negative photosensitive composition is preferably 20 Å/sec or more, more preferably 200 Å/sec or more, as measured (at 23° C.) in 0.261N tetramethylammonium hydroxide (TMAH).

Examples of the alkali-soluble resin for use in the present invention include, but are not limited to, a novolak resin, a hydrogenated novolak resin, an acetone-pyrogallol resin, an o-polyhydroxystyrene, an m-polyhydroxystyrene, a p-polyhydroxystyrene, a hydrogenated polyhydroxystyrene, a halogen- or alkyl-substituted polyhydroxystyrene, a hydroxystyrene-N-substituted maleimide copolymer, an o/p- or m/p-hydroxystyrene copolymer, a polyhydroxystyrene with the hydroxyl group being partially O-alkylated (for example, 5 to 30 mol % being O-methylated, O-(1-methoxy)ethylated, O-(1-ethoxy)ethylated, O-2-tetrahydropyranylated or O-(tert-butoxycarbonyl)methylated) or O-acylated (for example, 5 to 30 mol % being o-acylated or O-(tert-butoxy) carbonylated), a styrene-maleic anhydride copolymer, a styrene-hydroxystyrene copolymer, an α-methylstyrene-hydroxystyrene copolymer, a carboxyl group-containing methacrylic resin and a derivative thereof, and a polyvinyl alcohol derivative.

Among these alkali-soluble resins, preferred are a novolak resin, an o-polyhydroxystyrene, an m-polyhydroxystyrene, a p-polyhydroxystyrene, a copolymer thereof, an alkyl-substituted polyhydroxystyrene, a partially O-alkylated or O-acylated polyhydroxystyrene, a styrene-hydroxystyrene copolymer, and an α-methylstyrene-hydroxystyrene copolymer.

The novolak resin can be obtained by subjecting a predetermined monomer as the main component to addition condensation with aldehydes in the presence of an acidic catalyst.

The weight average molecular weight of the alkali-soluble resin is 2,000 or more, preferably from 5,000 to 200,000, more preferably from 5,000 to 100,000.

Here, the weight average molecular weight is defined as a polystyrene-reduced value measured by gel permeation chromatography.

In the present invention, two or more kinds of these alkali-soluble resins may be used in combination.

The amount of the alkali-soluble resin used is usually from 40 to 97 mass %, preferably from 60 to 90 mass %, based on the entire solid content of the photosensitive composition.

Acid Crosslinking Agent Capable of Crosslinking with the Alkali-Soluble Resin Under the Action of an Acid:

In the negative photosensitive composition of the present invention, a crosslinking agent capable of cross-linking with the alkali-soluble resin under the action of an acid (hereinafter sometimes referred to as a "crosslinking agent") is used.

The crosslinking agent may be any compound as long as it crosslinks with the alkali-soluble resin under the action of an acid, but the following compounds (1) to (3) are preferred:

(1) a hydroxymethyl, alkoxymethyl or acyloxymethyl form of a phenol derivative, (2) a compound having an N-hydroxymethyl group, an N-alkoxymethyl group or an N-acyloxymethyl group, and (3) a compound having an epoxy group.

The alkoxymethyl group is preferably an alkoxymethyl group having a carbon number of 6 or less, and the acyloxymethyl group is preferably an acyloxymethyl group having a carbon number of 6 or less.

Among these crosslinking agents, particularly preferred compounds are set forth below, but the present invention is not limited thereto.

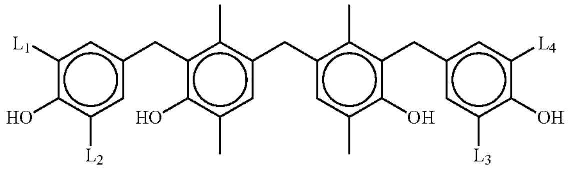

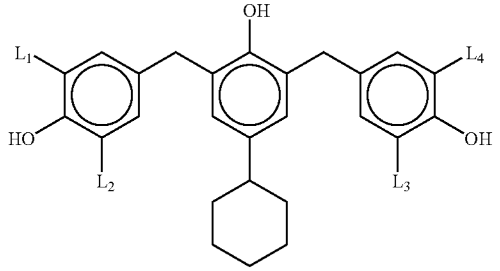

-continued

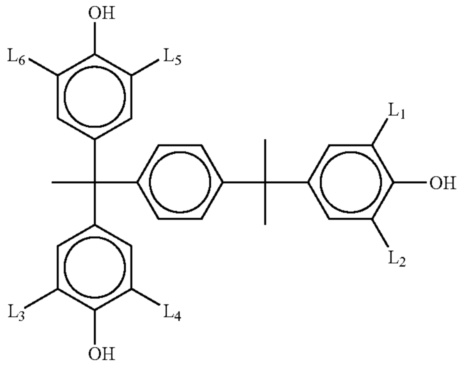

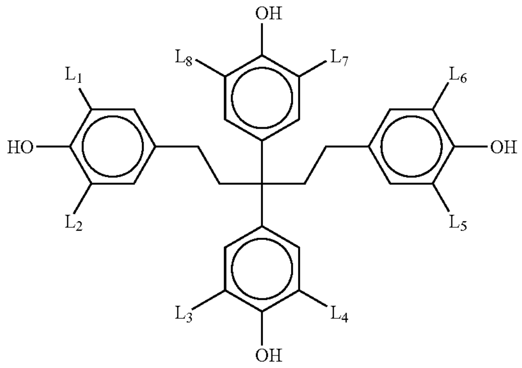

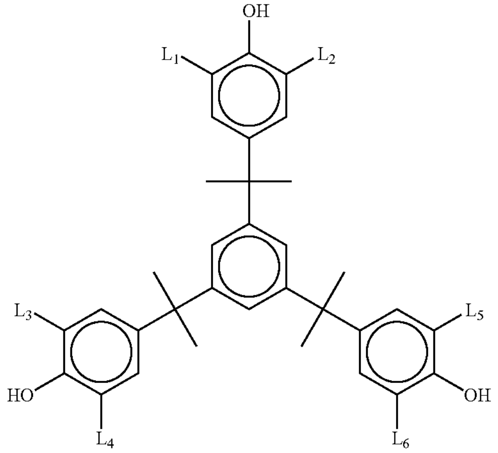

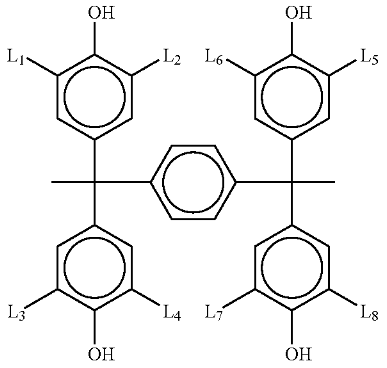

-continued

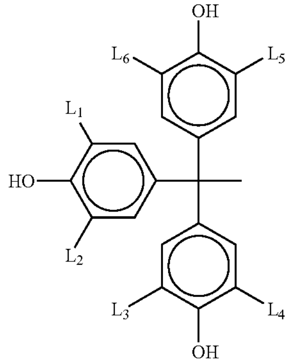

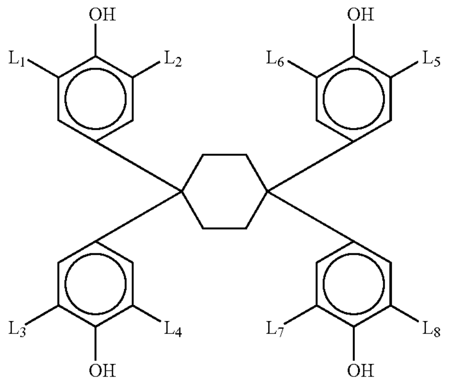

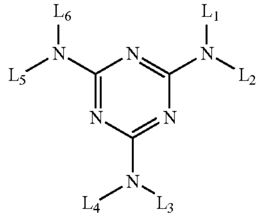

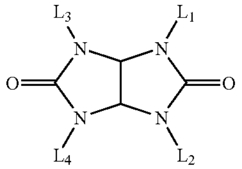

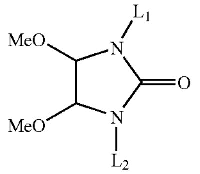

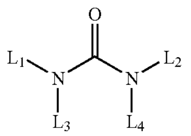

In the formulae, $L_1$ to $L_8$, which may be the same or different, each represents a hydrogen atom, a hydroxymethyl group, a methoxymethyl group, an ethoxymethyl group or an alkyl group having a carbon number of 1 to 6.

The crosslinking agent is usually used in an amount of 3 to 70 mass %, preferably from 5 to 50 mass %, based on the solid content of the negative photosensitive composition.

Basic Compound:

For the purpose of reducing changes in performance with the lapse of time from exposure to heating or controlling the diffusion of an acid generated by exposure into a layer, the photosensitive composition of the present invention preferably contains a basic compound.

The basic compound includes a nitrogen-containing basic compound and an onium salt compound.

As for the structure of the nitrogen-containing basic compound, a compound having a partial structure represented by any one of the following formulae (A) to (E) is preferred.

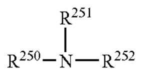
(A)

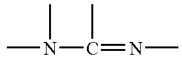
(B)

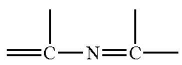
(C)

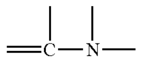
(D)

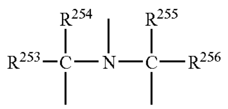
(E)

In formula (A), $R^{250}$, $R^{251}$ and $R^{252}$ each independently represents a hydrogen atom, an alkyl group having a carbon number of 1 to 20, a cycloalkyl group having a carbon number of 3 to 20, or an aryl group having a carbon number of 6 to 20, and $R^{250}$ and $R^{251}$ may combine with each other to form a ring. These groups each may have a substituent, and the alkyl group or cycloalkyl group having substituent is preferably an aminoalkyl group having a carbon number of 1 to 20, an aminocycloalkyl group having a carbon number of 3 to 20, a hydroxyalkyl group having a carbon number of 1 to 20, or a hydroxycycloalkyl group having a carbon number of 3 to 20.

Furthermore, these groups may contain an oxygen atom, a sulfur atom or a nitrogen atom in the alkyl chain.

In formula (E), $R^{253}$, $R^{254}$, $R^{255}$ and $R^{256}$ each independently represents an alkyl group having a carbon number of 1 to 6, or a cycloalkyl group having a carbon number of 3 to 6.

Preferred examples of the compound include guanidine, aminopyrrolidine, pyrazole, pyrazoline, piperazine, aminomorpholine, aminoalkylmorpholine and piperidine, and these each may have a substituent. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Examples of the compound having an imidazole structure include imidazole, 2,4,5-triphenylimidazole and benzimidazole. Examples of the compound having a diazabicyclo structure include 1,4-diazabicyclo[2,2,2]octane, 1,5-diazabicyclo[4,3,0]non-5-ene and 1,8-diazabicyclo[5,4,0]undec-7-ene. Examples of the compound having an onium hydroxide structure include triarylsulfonium hydroxide, phenacylsulfonium hydroxide and 2-oxoalkyl group-containing sulfonium hydroxide, and specific examples thereof include triphenylsulfonium hydroxide, tris(tert-butylphenyl)sulfonium hydroxide, bis(tert-butylphenyl)iodonium hydroxide, phenacylthiophenium hydroxide and 2-oxopropylthiophenium hydroxide. Examples of the compound having an onium carboxylate structure include a compound where the anion moiety of the compound having an onium hydroxide structure becomes a carboxylate, such as acetate, adamantane-1-carboxylate and perfluoroalkyl carboxylate. Examples of the compound having a trialkylamine structure include tri(n-butyl)amine and tri(n-octyl)amine. Examples of the aniline compound include 2,6-diisopropylaniline and N,N-dimethylaniline. Examples of the alkylamine derivative having a hydroxyl group and/or an ether bond include ethanolamine, diethanolamine, triethanolamine and tris(methoxyethoxyethyl)amine. Examples of the aniline derivative having a hydroxyl group and/or an ether bond include N,N-bis(hydroxyethyl)aniline.

One species or two or more species of these basic compounds are used. The amount of the basic compound used is usually from 0.001 to 10 mass %, preferably from 0.01 to 5 mass %, based on the solid content of the photosensitive composition. In view of obtaining a sufficiently high addition effect, the amount of the basic compound used is preferably 0.001 mass % or more, and in view of sensitivity and developability of the unexposed area, the amount used is preferably 10 mass % or less.

Fluorine-Containing and/or Silicon-Containing Surfactant:

The photosensitive composition of the present invention preferably further contains any one fluorine-containing and/or silicon-containing surfactant (a fluorine-containing surfactant, a silicon-containing surfactant, or a surfactant containing both a fluorine atom and a silicon atom), or two or more species thereof.

When the photosensitive composition contains a fluorine-containing and/or silicon-containing surfactant, in use of an exposure light source of emitting light at 250 nm or less, particularly 220 nm or less, a resist pattern assured of good adhesion and less development defect can be obtained with good sensitivity and resolution Examples of such a fluorine-containing and/or silicon-containing surfactant include the surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862 and U.S. Pat. Nos. 5,405,720, 5,360,692, 5,529,881, 5,296,330, 5,436,098, 5,576,143, 5,294,511 and 5,824,451. The following commercially available surfactants may also be directly used.

Examples of the commercially available surfactant which can be used include a fluorine-containing or silicon-containing surfactant such as EFtop EF301 and EF303 (produced by Shin-Akita Chemical Co., Ltd.), Florad FC430 and 431 (produced by Sumitomo 3M Inc.), Megafac F171, F173, F176, F189 and R09 (produced by Dainippon Ink & Chemicals, Inc.), Surflon S-382, SC101, 102, 103, 104, 105 and 106 (produced by Asahi Glass Co., Ltd.), and Troysol S-366 (produced by Troy Chemical Industries, Inc.). In addition, polysiloxane polymer KP-341 (produced by Shin-Etsu Chemical Co, Ltd.) may also be used as the silicon-containing surfactant.

Other than those known surfactants, a surfactant using a polymer having a fluoro-aliphatic group derived from a fluoro-aliphatic compound produced by a telomerization process (also called a telomer process) or an oligomerization process (also called an oligomer process) may be used. The fluoro-aliphatic compound can be synthesized by the method described in JP-A-2002-90991.

The polymer having a fluoro-aliphatic group is preferably a copolymer of a fluoro-aliphatic group-containing monomer with a (poly(oxyalkylene)) acrylate and/or a (poly(oxyalkylene)) methacrylate, and the polymer may have an irregular distribution or may be a block copolymer Examples of the poly(oxyalkylene) group include a poly(oxyethylene) group, a poly(oxypropylene) group and a poly(oxybutylene) group. This group may also be a unit having alkylenes differing in the chain length within the same chain, such as block-linked poly(oxyethylene, oxypropylene and oxyethylene) and block-linked poly(oxyethylene and oxypropylene). Furthermore, the copolymer of a fluoro-aliphatic group-containing monomer with a (poly(oxyalkylene)) acrylate (or methacrylate) may be not only a binary copolymer but also a ternary or higher copolymer obtained by simultaneously copolymerizing two or more different fluoro-aliphatic group-containing monomers or two or more different (poly(oxyalkylene)) acrylates (or methacrylates).

Examples thereof include commercially available surfactants such as Megafac F178, F-470, F-473, F-475, F-476 and F-472 (produced by Dainippon Ink & Chemicals, Inc.), and further include a copolymer of a $C_6F_{13}$ group-containing acrylate (or methacrylate) with a (poly(oxyalkylene)) acrylate (or methacrylate), a copolymer of a $C_6F_{13}$ group-containing acrylate (or methacrylate) with (poly(oxyethylene)) acrylate (or methacrylate) and (poly(oxypropylene)) acrylate (or methacrylate), a copolymer of a $C_8F_{17}$ group-containing acrylate (or methacrylate) with a (poly(oxyalkylene)) acrylate (or methacrylate), and a copolymer of a $C_8F_{17}$ group-containing acrylate (or methacrylate) with (poly(oxyethylene)) acrylate (or methacrylate) and (poly(oxypropylene)) acrylate (or methacrylate).

The amount of the fluorine-containing and/or silicon-containing surfactant used is preferably from 0.0001 to 2 mass %, more preferably from 0.001 to 1 mass %, based on the entire amount of the photosensitive composition (excluding the solvent).

Surface Hydrophobing Resin:

In the case where a photosensitive film comprising the photosensitive composition of the present invention is exposed through immersion liquid, a surface hydrophobing resin may be further added, if desired, to the photosensitive composition part t. By this addition, the receding contact angle on the resist film surface and in turn, the followability to immersion liquid can be enhanced.

The surface hydrophobing resin may be any resin as long as the receding contact angle on the surface is enhanced by its addition, but a resin having at least either one of a fluorine atom and a silicon atom is preferred. The amount of the surface hydrophobing resin added may be appropriately adjusted to give a resist film having a receding contact angle of 60 to 80° but is preferably from 0.1 to 5 mass %.

Organic Solvent:

The photosensitive composition of the present invention is used by dissolving the components described above in a predetermined organic solvent.

Examples of the solvent which can be used include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethylsulfoxide, N-methylpyrrolidone and tetrahydrofuran.

In the present invention, the solvent may be a sole solvent or a mixture of solvents, but it is preferred to use a mixed solvent containing two or more kinds of solvents having different functional groups. By the use of a mixed solvent, the solubility of raw materials is increased and not only the generation of particles with aging can be suppressed but also a good pattern profile can be obtained. The mixed solvent containing two or more kinds of solvent having different functional groups is preferably a mixed solvent containing at least two members selected from a solvent containing a hydroxyl group, a solvent having an ester structure, a solvent having a ketone structure, a solvent having a lactone structure, and a solvent having a carbonate structure.

As for the mixed solvent containing two or more kinds of solvent having different functional groups, the following mixed solvents (S1) to (S6) are preferred:

(S1) a mixed solvent containing at least a hydroxyl group-containing solvent and a hydroxyl group-free solvent;

(S2) a mixed solvent containing at least a solvent having an ester structure and a solvent having a ketone structure;

(S3) a mixed solvent containing at least a solvent having an ester structure and a solvent having a lactone structure;

(S4) a mixed solvent containing a solvent having an ester structure, a solvent having a lactone structure, and a hydroxyl group-containing solvent;

(S5) a mixed solvent containing at least a solvent having an ester structure, a solvent having a carbonate structure, and a hydroxyl group-containing solvent; and (S6) a mixed solvent containing at least a solvent having an ester structure, a solvent having a ketone structure, and a solvent having a lactone structure.

By the use of such a mixed solvent, generation of particles during storage of the resist solution can be reduced, and generation of a defect at the coating can be suppressed.

Examples of the hydroxyl group-containing solvent include ethylene glycol, ethylene glycol monomethyl ether, ethylene glycol monoethyl ether, propylene glycol, propylene glycol monomethyl ether, propylene glycol monoethyl ether and ethyl lactate. Along these, propylene glycol monomethyl ether and ethyl lactate are preferred.

Examples of the hydroxyl group-free solvent include propylene glycol monomethyl ether acetate, ethyl ethoxy propionate, 2-heptanone, γ-butyrolactone, cyclohexanone, butyl acetate, N-methylpyrrolidone, N,N-dimethylacetamide and dimethyl sulfoxide. Among these, propylene glycol mono ethyl ether acetate, ethyl ethoxy propionate, 2-heptanone, 7-butyrolactone, cyclohexanone and butyl acetate are preferred, and propylene glycol monomethyl ether acetate, ethyl ethoxy propionate, 2-heptanone and cyclohexanone are more preferred.

Examples of the solvent having a ketone structure include cyclohexanone and 2-heptanone, with 2-heptanone being preferred.

Examples of the solvent having an ester structure include propylene glycol monomethyl ether acetate, ethyl ethoxy propionate and butyl acetate, with propylene glycol monomethyl ether acetate being preferred.

Examples of the solvent having a lactone structure include γ-butyrolactone.

Examples of the solvent having a carbonate structure include propylene carbonate and ethylene carbonate, with propylene carbonate being preferred.

In (S1), the mixing ratio (by mass) of the hydroxyl group-containing solvent to the hydroxyl group-free solvent is from 1/99 to 99/1, preferably from 10/90 to 90/10, more preferably from 20/80 to 60/40. A mixed solvent containing 50 mass % or more of the hydroxyl group-free solvent is particularly preferred in view of coating uniformity.

In (S2), the mixing ratio (by mass) of the solvent having an ester structure to the solvent having a ketone structure is from 1/99 to 99/1, preferably from 10/90 to 90/10, more preferably from 40/60 to 80/20. A mixed solvent containing 50 mass % or more of the solvent having an ester structure is particularly preferred in view of coating uniformity.

In (S3), the mixing ratio (by mass) of the solvent having an ester structure to the solvent having a lactone structure is from 70/30 to 99/1, preferably from 80/20 to 99/1, more preferably from 90/10 to 99/1. A mixed solvent containing 70 mass % or more of the solvent having an ester structure is particularly preferable in view of coating uniformity.

In (S4) where the solvent having an ester structure, the solvent having a lactone structure and the hydroxyl group-containing solvent are mixed, the mixed solvent preferably contains from 30 to 80 wt % of the solvent having an ester structure, from 1 to 20 wt % of the solvent having a lactone structure, and from 10 to 60 wt % of the hydroxyl group-containing solvent.

In (S5) where the solvent having an ester structure, the solvent having a carbonate structure and the hydroxyl group-containing solvent are mixed, the mixed solvent preferably contains from 30 to 80 wt % of the solvent having an ester structure, from 1 to 20 wt % of the solvent having a carbonate structure, and from 10 to 60 wt % of the hydroxyl group-containing solvent.

In (S6) where the solvent having an ester structure, the solvent having a ketone structure and the solvent having a lactone structure are mixed, the mixed solvent preferably contains from 30 to 80 wt % of the solvent having an ester structure, from 10 to 60 wt % of the solvent having a ketone structure, and from 1 to 20 wt % of the solvent having a lactone structure.

<Other Additives>

If desired, the photosensitive composition of the present invention may further contain, for example, a dye, a plasticizer, a surfactant other than the fluorine-containing and/or silicon-containing surfactant above, a photosensitizer, and a compound capable of accelerating the dissolution in a developer.

The compound capable of accelerating the dissolution in a developer, which can be used in the present invention, is a low molecular compound containing two or more phenolic OH groups or one or more carboxy groups and having a molecular weight of 1,000 or less. In the case of containing a carboxyl group, an alicyclic or aliphatic compound is preferred.

The amount of the dissolution accelerating compound added is preferably from 2 to 50 mass %, more preferably from 5 to 30 mass %, based on the resin as the component (B). The amount added is preferably 50 mass % or less in the light of suppressing the development residue or preventing the pattern deformation at the development.

The phenol compound having a molecular weight of 1,000 or less can be easily synthesized by one skilled in the art with reference to the method described, for example, in JP-A-4-122938, JP-A-2-28531, U.S. Pat. No. 4,916,210 and European Patent 219294.

Specific examples of the alicyclic or aliphatic compound having a carboxy group include, but are not limited to, a carboxylic acid derivative having a steroid structure, such as cholic acid, deoxycholic acid and lithocholic acid, an adamantane carboxylic acid derivative, an adamantane dicarboxylic acid, a cyclohexanecarboxylic acid and a cyclohexanedicarboxylic acid.

In the present invention, a surfactant other than the fluorine-containing and/or silicon-containing surfactant above may also be added. Specific examples thereof include a nonionic surfactant such as polyoxyethylene alkyl ethers, polyoxyethylene alkylallyl ethers, polyoxyethylene.polyoxypropylene block copolymers, sorbitan fatty acid esters and polyoxyethylene sorbitan fatty acid esters.

One of these surfactants may be added alone, or some species thereof may be added in combination.

(Pattern Forming Method)

The photosensitive composition of the present invention is used by dissolving the components described above in a predetermined organic solvent, preferably in the mixed solvent above, filtering the solution, and coating it on a predetermined support as follows. The filter used for filtration is preferably a filter made of polytetrafluoro-ethylene, polyethylene or nylon and having a pore size of 0.1 micron or less, more preferably 0.05 microns or less, still more preferably 0.03 microns or less.

For example, the photosensitive composition is coated on a substrate (e.g., silicon/silicon dioxide-coated substrate) as those used in the production of precision integrated circuit devices, to an arbitrary thickness (usually from 50 to 500 nm) by an appropriate coating method such as spinner or coater. After the coating, the composition is dried by spinning or baking to form a resist film. The baking temperature may be appropriately set but is usually from 60 to 150° C., preferably from 90 to 130° C.

Subsequently, the resist film is exposed through a mask or the like to form a pattern.

The exposure amount may be appropriately set but is usually from 1 to 100 $mJ/cm^2$. After the exposure, spinning and/or baking is preferably performed, and the resist film is then developed and rinsed to obtain a pattern.

The exposure may be performed by filling a liquid (immersion medium) having a refractive index higher than that of air between the photosensitive film and a lens at the irradiation with actinic rays or radiation (immersion exposure). By this exposure, the resolution can be enhanced. The immersion medium used is preferably pure water, but any liquid may be used as long as it has a refractive index higher than that of air. Also, in order to prevent the immersion medium and the photosensitive film from coming into direct contact at the immersion exposure, an overcoat layer may be further provided on the photosensitive film. In this case, the composition can be restrained from dissolving out into the immersion medium from the photosensitive film, and the development defects can be reduced.

Examples of the actinic rays or radiation include infrared light, visible light, ultraviolet light, far ultraviolet light, X-ray and electron beam, but the radiation is preferably far ultraviolet light at a wavelength of 250 nm or less, more preferably 220 nm or less. Specific examples thereof include KrF excimer laser light (248 nm), ArF excimer laser light (193 nm), $F_2$ excimer laser light (157 nm), EUV (13 nm), X-ray and electron beam. Among these, ArF excimer laser light, $F_2$ excimer laser light, EUV (13 nm) and electron beam are preferred.

Before forming the resist film, an antireflection film may be previously provided by coating on the substrate.

The antireflection film used may be either an inorganic film type such as titanium, titanium dioxide, titanium nitride, chromium oxide, carbon and amorphous silicon, or an organic film type comprising a light absorbent and a polymer material. Also, the organic antireflection film may be a commercially available organic antireflection film such as DUV30 Series and DUV-40 Series produced by Brewer Science, Inc., and AR-2, AR-3 and AR-5 produced by Shipley Co., Ltd.

In the development step, an alkali developer is used as follows. The alkali developer for the resist composition is an alkaline aqueous solution of inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, and cyclic amines such as pyrrole and piperidine.

Furthermore, this alkali developer may be used after adding thereto alcohols and a surfactant each in an appropriate amount.

The alkali concentration of the alkali developer is usually from 0.1 to 20 mass %.

The pH of the alkali developer is usually from 10.0 to 14.0.

The positive resist composition of the present invention may be applied to a multilayer resist process (particularly, a three-layer resist process). The multilayer resist process comprises the following steps:

(a) forming a lower resist layer comprising an organic material on a substrate to be processed, (b) sequentially stacking on the lower resist layer an interlayer and an upper resist layer comprising an organic material capable of crosslinking or decomposing upon irradiation with radiation, and (c) forming a predetermined pattern on the upper resist layer and then sequentially etching the intermediate layer, the lower layer and the substrate.

In general, an organopolysiloxane (silicone resin) or $SiO_2$ coating solution (SOG) is used for the intermediate layer. As for the lower layer resist, an appropriate organic polymer film is used, but various known photoresists may be used. Examples thereof include various Series such as FH Series and FHi Series produced by Fujifilm Arch Co., Ltd. and PFI Series produced by Sumitomo Chemical Co., Ltd.

The film thickness of the lower resist layer is preferably from 0.1 to 4.0 μl, more preferably from 0.2 to 2.0 μm, still more preferably from 0.25 to 1.5 μm. The film thickness is preferably 0.1 μm or more in view of antireflection or dry etching resistance and preferably 4.0 μm or less in the light of aspect ratio or pattern collapse of the fine pattern formed.

EXAMPLES

The present invention is described in greater detail below by referring to Examples, but the present invention should not be construed as being limited thereto.

Synthesis Example 1

Synthesis of Compound (I-1)

Silver trifluoromethanesulfonate (5 g) and 50 ml of benzene were mixed, 4.2 g of 1-bromoadamantane dissolved in 50 ml of benzene was added thereto over 30 minutes, and the resulting mixture was stirred for 12 hours in a dark place. The obtained reaction solution was poured in 300 ml of water and extracted with hexane, and the organic phase was washed with water and saturated saline, dried and concentrated to obtain a crude product. This crude product was purified by column chromatography, as a result, 1.7 g of 1-phenyladamantane was obtained.

Subsequently, 1.6 g of 1-phenyladamantane and 1.5 g of diphenyl sulfoxide were mixed with 10 ml of dichloromethane, 10 g of trifluoroacetic anhydride was added thereto, 2.4 g of nonafluorobutanesulfonic acid was further added at −30° C., and the reaction was allowed to proceed for 2 hours. The temperature was elevated to room temperature and after stirring for 1 hour, the reaction solution was pored in ice and extracted with chloroform. The organic phase was washed with an aqueous saturated $NaHCO_3$ solution and water, concentrated and then purified by column chromatography to obtain 2.9 g of Compound (I-1).

$^1$H-NMR ($CDCl_3$) δ 1.6-2.2 (m, 15H), δ 7.6-7.8 (m, 14H).

Synthesis Example 2

Synthesis of Compound (I-2)

4-(1-Adamantylmethoxymethyl)phenyldiphenyl sulfonium bromide (2 g) was dissolved in 30 ml of methanol, and 1.36 g of potassium nonafluorobutanesulfonate dissolved in a water/methanol mixed solution was added thereto. The obtained reaction solution was extracted with chloroform, and the organic phase was washed with water and then concentrated to obtain a crude product. Diisopropyl ether was added thereto and the resulting mixture was stirred, as a result, a powder material was precipitated. This powder material was collected by filtration and dried to obtain 1.2 g of Compound (I-2).

$^1$H-NMR ($CDCl_3$)

δ 1.6-1.8 (m, 12H), δ 2.0 (bs, 3H), δ 3.1 (s, 2H), δ 4.6 (s, 2H), δ 7.6-7.8 (m, 14H).

Other compounds as the component (A) were synthesized in the same manner.

Synthesis Example 3

Synthesis of Resin (RA-1)

Under a nitrogen stream, 8.4 g of cyclohexanone was charged into a three-neck flask and heated at 80° C. Thereto, a solution prepared by dissolving 6.8 g of γ-butyrolactone methacrylate, 4.7 g of 3-hydroxyadamantyl-1-methacrylate, 9.4 g of 2-methyl-2-adamantyl methacrylate, and polymerization initiator V-60 (produced by Wako Pure Chemical Industries, Ltd.) in an amount of 13 mol % based on the monomer, in 75 g of cyclohexanone was added dropwise over 6 hours. After the completion of dropwise addition, the reaction was further allowed to proceed at 80° C. for 2 hours. The reaction solution was left standing to cool and then added dropwise to a mixed solution of 900-ml methanol/100-ml water over 20 minutes, and the precipitated powder material was collected by filtration and dried to obtain 178 g of Resin (RA-1). The weight average molecular weight of the resin obtained was 6,300 in terms of standard polystyrene, and the dispersity (Mw/Mn) was 1.60.

Resins (RA-2) to (RA-12) were synthesized in the same manner. The weight average molecular weight was adjusted by changing the amount of the initiator.

Structures of Resins (RA-1) to (RA-12) are shown below.

RA-1

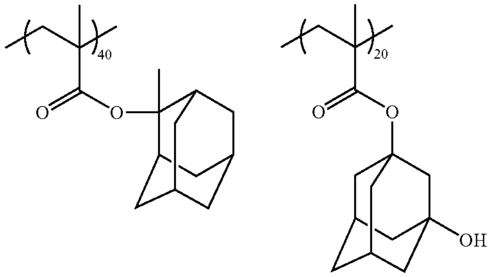

-continued

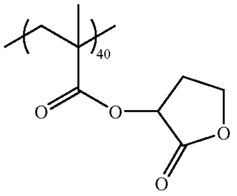

Mw = 6300
Mw/Mn = 1.60

RA-2

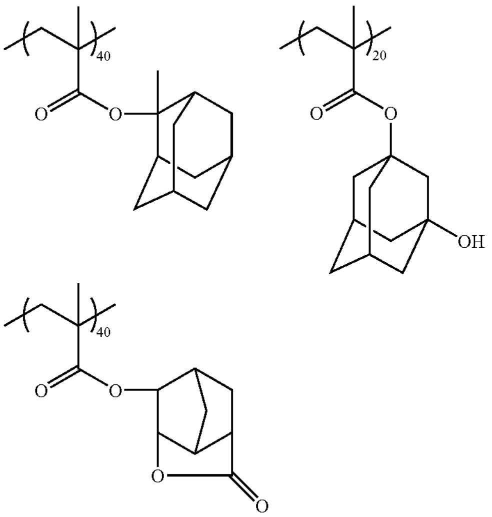

Mw = 11200
Mw/Mn = 1.65

RA-3

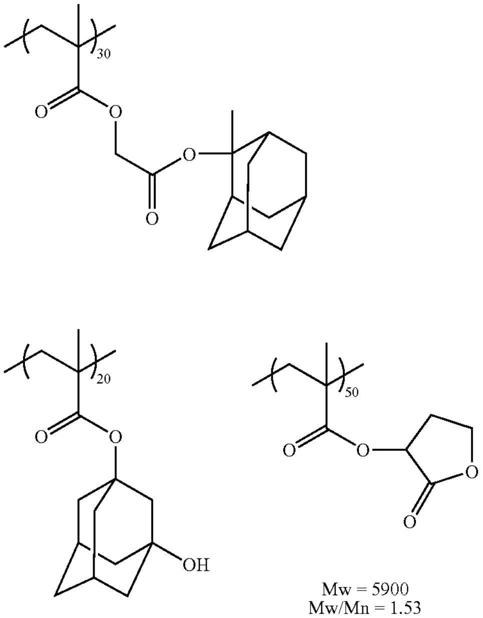

Mw = 5900
Mw/Mn = 1.53

-continued
RA-4
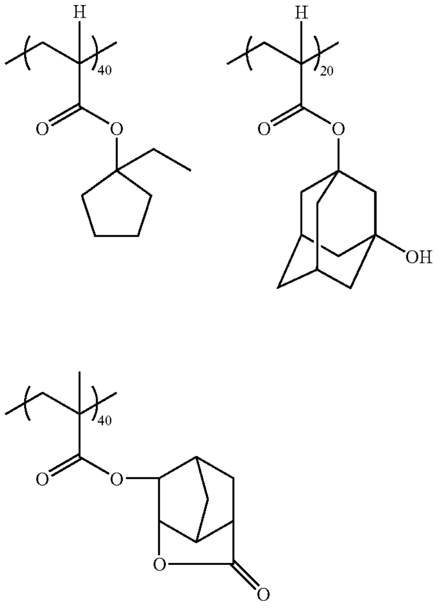
Mw = 12600
Mw/Mn = 1.80
RA-5
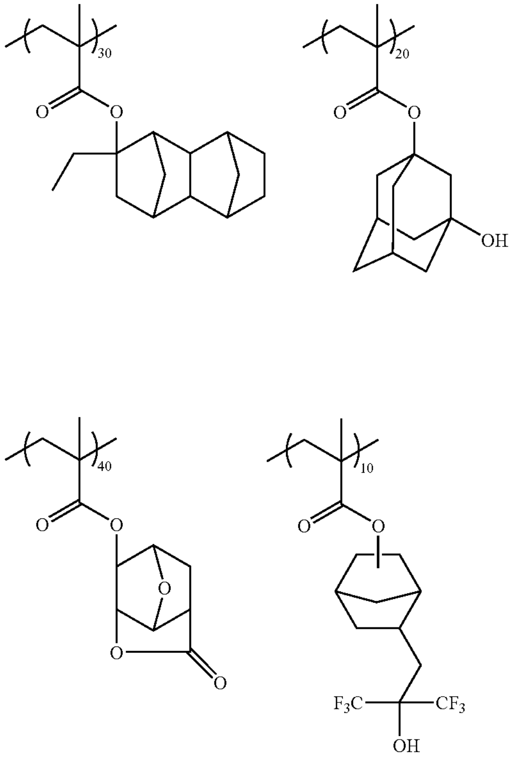
Mw = 8400
Mw/Mn = 1.74
-continued
RA-6
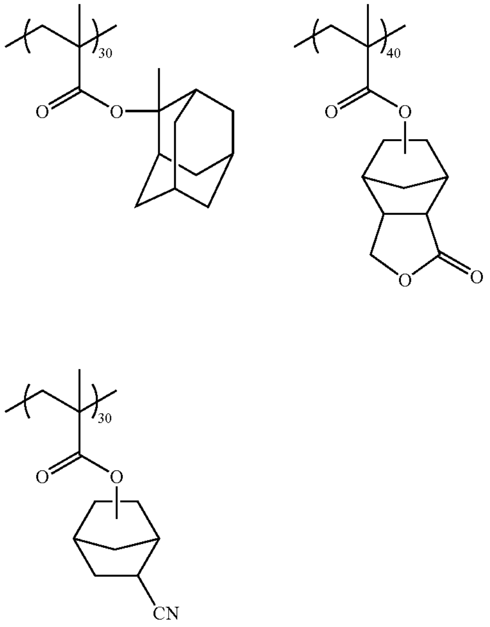
Mw = 19600
Mw/Mn = 1.90
RA-7
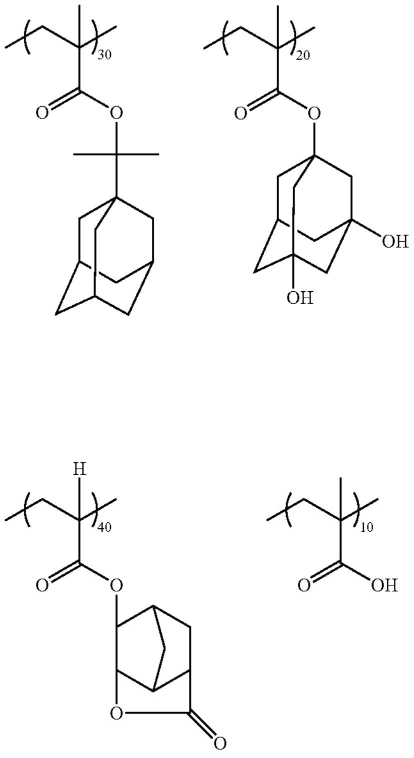
Mw = 8900
Mw/Mn = 1.80

-continued
RA-8
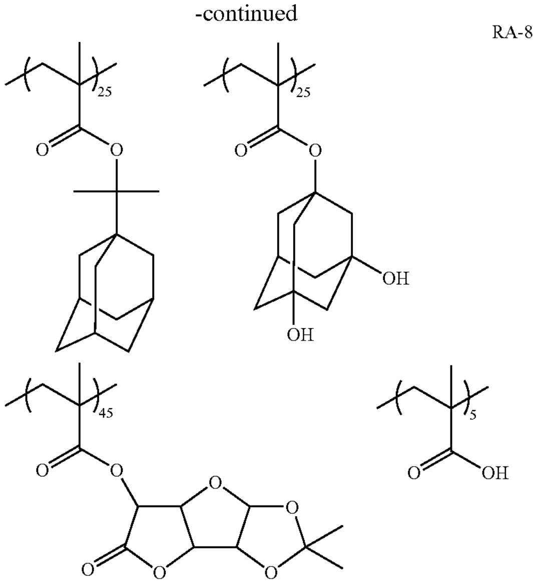
Mw = 9300
Mw/Mn = 1.79
RA-9
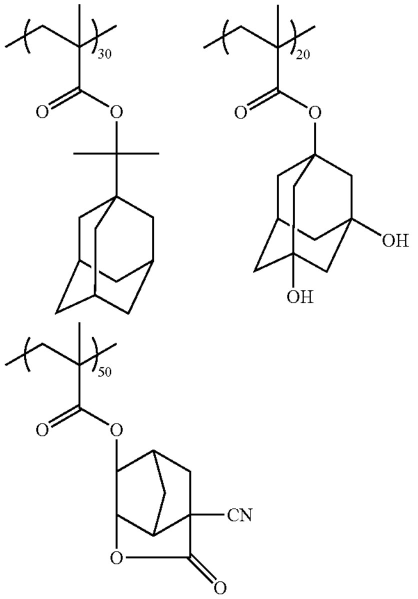
Mw = 6100
Mw/Mn = 1.73
RA-10
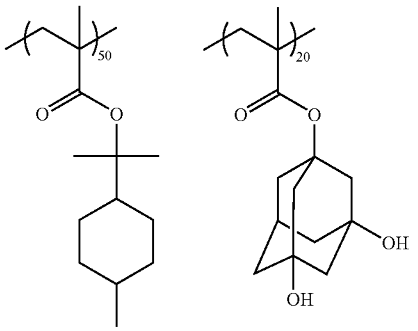
-continued
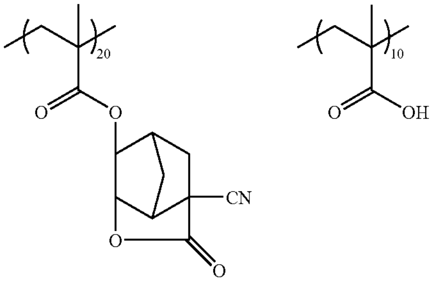
Mw = 11000
Mw/Mn = 1.80
RA-11
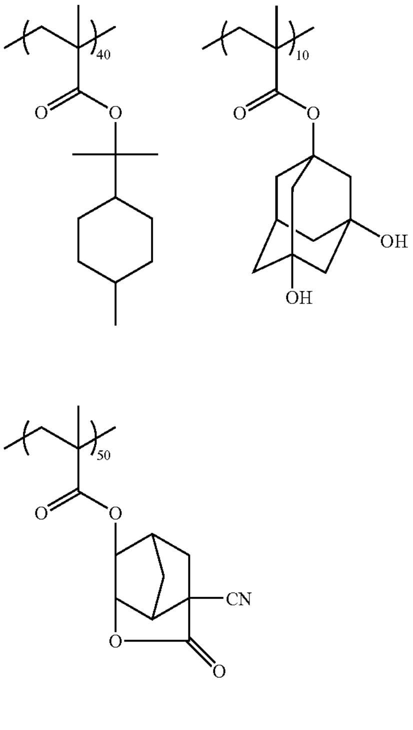
Mw = 8000
Mw/Mn = 1.74
RA-12
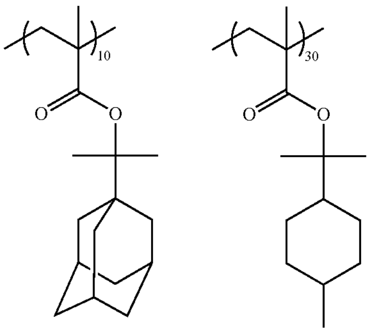

-continued

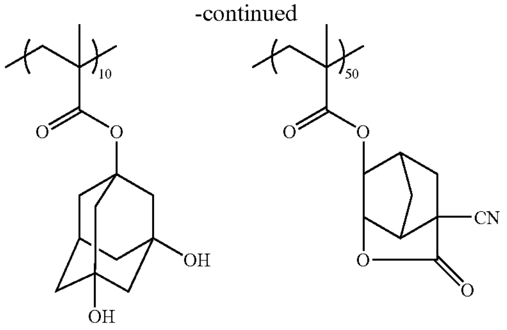

Mw = 7900
Mw/Mn = 1.76

Examples 1 to 13 and Comparative Examples 1 and 2

Preparation of Resist

The components shown in Table 1 below were dissolved in a solvent to prepare a solution having a solid content concentration of 7 mass %, and the obtained solution was filtered through a 0.03-micron polyethylene filter to prepare a positive resist solution. The positive resist solutions prepared were evaluated by the following methods, and the results are also shown in Table 1.

<Evaluation of Resist>

On a silicon substrate treated with hexamethyldisilazane, an antireflection film, DUV-42, produced by Brewer Science, Inca was uniformly coated by a spin coater to a thickness of 600 Å, dried at 100° C. for 90 seconds on a hot plate and further dried under heating at 190° C. for 240 seconds. Thereafter, the positive resist solutions each was coated thereon by a spin coater and dried at 120° C. for 60 seconds to form a 160-nm resist film.

This resist film was exposed using an ArF excimer laser stepper (manufactured by ASML, NA=0.75, dipole) through a mask and immediately after the exposure, heated at 120° C. for 60 seconds on a hot plate. Thereafter, the resist film was developed with an aqueous 2.38 mass % tetramethylammonium hydroxide solution at 23° C. for 60 seconds, rinsed with pure water for 30 seconds and then dried to obtain a line pattern.

Evaluation Method of Pattern Collapse:

The exposure amount for reproducing a mask pattern of 75-nm line/75-nm space was taken as an optimal exposure amount and when the exposure amount was further increased from the optimal exposure amount and the line width of the line pattern formed was decreased, the line width resolved without causing collapse of the pattern was used for the definition. A smaller value indicates that a finer pattern is resolved without collapsing, and reveals less occurrence of pattern collapse and higher resolving power.

Evaluation Method of Film Loss:

The pattern profile of 90-nm line/900-nm space (isolated pattern) at an exposure amount for reproducing a mask pattern of 75-nm line/75-nm space was evaluated. Rating was ○ when the profile was rectangular, Δ when slight film loss occurred, and X when serious film loss was generated

TABLE 1

| Example | (A) Acid Generator (g) | (B) Resin (10 g) | Basic Compound (g) | Surfactant (g) | Solvent (ratio by mass) | Pattern Collapse (nm) | Film Loss |
|---|---|---|---|---|---|---|---|
| 1 | I-1 (0.5) | RA-1 | DIA (0.05) | W-4 (0.01) | S1/S5 = 60/40 | 55 | ○ |
| 2 | I-2 (0.5) | RA-2 | PEA (0.05) | W-2 (0.02) | S1/S4/S2 = 80/5/15 | 55 | ○ |
| 3 | I-3 (0.4) | RA-3 | TEA (0.03) | W-1 (0.01) | S1/S6 = 95/5 | 55 | ○ |
| 4 | I-4 (0.4) | RA-4 | DIA (0.03) | W-4 (0.01) | S1/S5/S7 = 60/38/2 | 55 | ○ |
| 5 | I-5 (0.3) | RA-5 | PEA (0.02) | W-4 (0.01) | S1/S5 = 80/20 | 55 | ○ |
| 6 | I-7 (0.8) | RA-6 | DIA (0.02)<br>PEA (0.02) | W-4 (0.01) | S1/S4/S6 = 80/5/15 | 55 | ○ |
| 7 | I-10 (0.4) | RA-7 | TMEA (0.03) | W-3 (0.03) | S1/S3 = 60/40 | 50 | ○ |
| 8 | I-11 (0.5) | RA-8 | PBI (0.04) | W-1 (0.005) | S1/S6 = 80/20 | 50 | ○ |
| 9 | I-16 (0.6) | RA-9 | PBA (0.03) | W-3 (0.02) | S1/S5 = 60/40 | 45 | ○ |
| 10 | I-1 (0.5) | RA-10 | TPSA (0.05) | W-3 (0.01) | S1/S5 = 60/40 | 45 | ○ |
| 11 | I-2 (0.5) | RA-11 | DIA (0.05) | W-4 (0.01) | S1/S5 = 60/40 | 45 | ○ |
| 12 | I-1 (0.5) | RA-12 | PEA (0.05) | W-4 (0.01) | S1/S5 = 60/40 | 45 | ○ |
| 13 | I-1 (0.4)<br>PAG-A (0.1) | RA-9 (5 g)<br>RA-11 (5 g) | DIA (0.02)<br>PEA (0.02) | W-4 (0.01) | S1/S4/S6 = 80/5/15 | 45 | ○ |

| Comparative Example | (A) Acid Generator (g) | (B) Resin (10 g) | Basic Compound (g) | Surfactant (g) | Solvent | Pattern Collapse (nm) | Film Loss |
|---|---|---|---|---|---|---|---|
| 1 | PAG-A (0.5) | RA-1 | DIA (0.05) | W-4 (0.01) | S1/S5 = 60/40 | 60 | Δ |
| 2 | PAG-B (0.5) | RA-1 | DIA (0.05) | W-4 (0.01) | S1/S5 = 60/40 | 65 | X |

The abbreviations in Table 1 indicate the followings.

[Acid Generator]

I-1

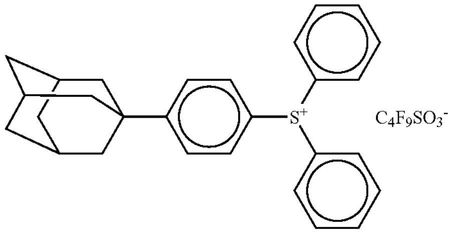

I-2

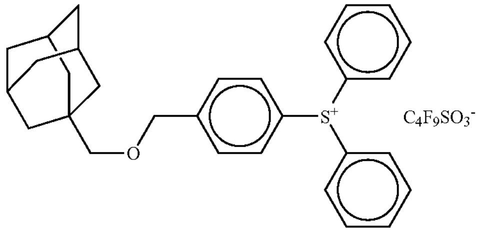

I-3

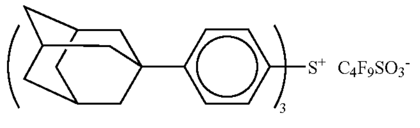

I-4

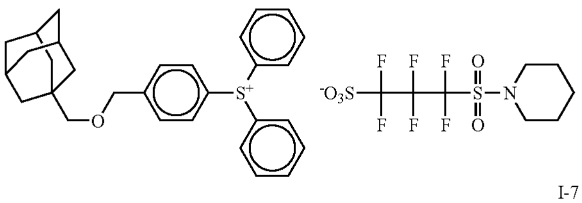

I-7

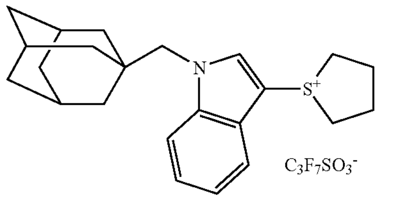

I-10

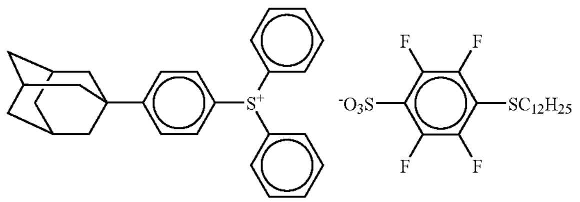

I-11

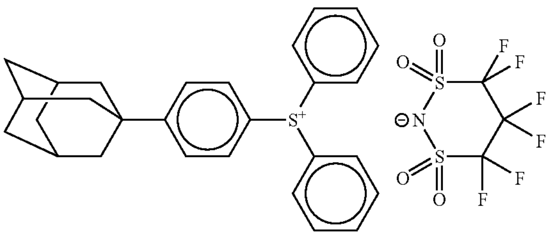

-continued

I-16

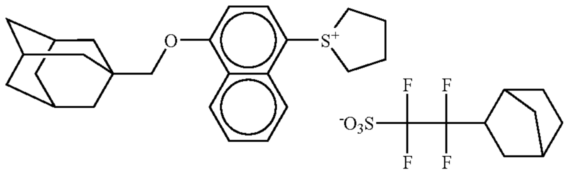

PAG-A

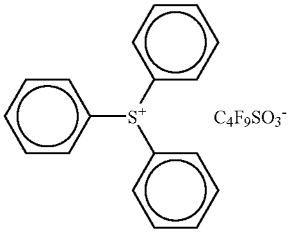

PAG-B

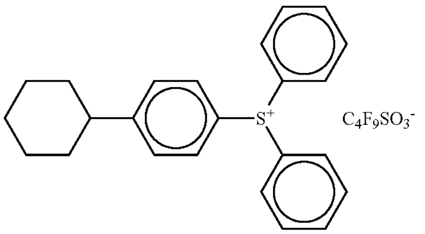

[Basic Compound]
TPSA: triphenylsulfonium acetate
DIA: 2,6-diisopropylaniline
TEA: triethanolamine
PBI: 2-phenylbenzimidazole
TMEA: tris(methoxyethoxyethyl)amine
PEA: N-phenyldiethanolamine

[Surfactant]
W-1: Megafac F176 (produced by Dainippon Ink & Chemicals, Inc.) (fluorine-containing)
W-2: Megafac R08 (produced by Dainippon Ink & Chemicals, Inc.) (fluorine- and silicon-containing)
W-3: Polysiloxane Polymer KP-341 (produced by Shin-Etsu Chemical Co., Ltd.) (silicon-containing)
W-4: Troysol S-366 (produced by Troy Chemical) (silicon-containing)

[Solvent]
S1: propylene glycol methyl ether acetate
S2: 2-heptanone
S3: cyclohexanone
S4: γ-butyrolactone
S5: propylene glycol methyl ether
S6: ethyl lactate
S7: propylene carbonate As apparent from Table 1, the photosensitive composition of the present invention can improve the performance in terms of pattern collapse and gives a good profile.

(Immersion Exposure)

<Preparation of Resist>

The components of each of Examples 1 to 13 and Comparative Examples 1 and 2 shown in Table 1 were dissolved in a solvent to prepare a solution having a solid content concentration of 5 mass %, and this solution was filtered through a 0.03-μm polyethylene filter to prepare a positive resist solution. The prepared positive resist solutions were evaluated by the following methods.

<Evaluation of Resolution>

An organic antireflection film ARC29A (produced by Nissan Chemical Industries, Ltd.) was coated on a silicon wafer and baked at 205° C. for 60 seconds to form a 78-nm antireflection film. On this films the resist composition prepared was coated and baked at 115° C. for 60 seconds to form a 140-nm resist film. The thus-obtained wafer was subjected to two-beam interference exposure (wet exposure) using pure water as the immersion liquid. In the two-beam interference exposure (wet exposure), as shown in FIG. 1, the wafer 10 with an antireflection film and a resist film provided on the wafer stage 11 was exposed through a prism 8 and an immersion liquid (pure water) 9 by using a laser 1, a diaphragm 2, a shutter 3, three reflecting mirrors 4, 5 and 6, and a condenser lens 7. The wavelength of the laser 1 used was 193 nm, and a prism 8 of forming a 65-nm line-and-space pattern was used. Immediately after the exposure, the resist film was heated at 115° C. for 90 seconds. Furthermore, the resist film was developed with an aqueous tetramethylammonium hydroxide solution (2.38%) for 60 seconds, rinsed with pure water and spin-dried. The obtained resist pattern was observed by a scanning electron microscope (S-9260, manufactured by Hitachi Ltd.). In the case of using the positive resist solutions of Examples 1 to 13, a 65-nm line-and-space pattern was resolved without causing pattern collapse. In the case of using the positive resist solutions of Comparative Examples 1 and 2, a 65-nm line-and-space pattern was resolved, but pattern collapse was observed in a part of the pattern.

It is apparent that the photosensitive composition of the present invention exhibits a good image-forming performance also in the exposure through an immersion liquid.

Example 14 and Comparative Example 3

(1) Formation of Lower Resist Layer

FHi-028DD Resist (resist for i-line, produced by Fujifilm Olin Co., Ltd.) was coated on a silicon wafer by using a spin coater and baked at 90° C. for 90 seconds to obtain a uniform film having a thickness of 0.55 μm.

This film was further heated at 200° C. for 3 minutes to form a lower resist layer having a thickness of 0.40 μm.

(2) Formation of Upper Resist Layer

The components shown in Table 2 below were dissolved in a solvent to prepare a solution having a solid content concentration of 8 mass %, and this solution was microfiltered through a membrane filter having a pore size of 0.03 μm to prepare an upper resist composition.

This upper resist composition was coated on the lower resist layer in the same manner as the lower layer and heated at 130° C. for 90 seconds to form an upper resist layer having a thickness of 0.20 μm.

(3) Evaluation of Resist

The thus-obtained wafer was exposed through a mask by using an ArF excimer laser scanner (manufactured by ASML, NA: 0.75). Immediately after the exposure, the wafer with upper and lower resist layers was heated at 120° C. for 90 seconds on a hot plate, developed with an aqueous 2.38 mass % tetramethylammonium hydroxide solution at 23° C. for 60 seconds, rinsed with pure water for 30 seconds and dried to form a line pattern.

Evaluation Method of Pattern Collapse:

The exposure amount for reproducing a line-and-space mask pattern with a line width of 90 nm was taken as an optimal exposure amount and when the exposure amount was increased from the optimal exposure amount and the line pattern was thinned, the line width at which the pattern collapsed was observed. As the value is smaller, a finer pattern can be formed without causing pattern collapse and the performance in terms of pattern collapse is higher.

Evaluation Method of Film Loss:

The pattern profile of 100-nm line/1000-nm space (isolated pattern) at an exposure amount for reproducing a mask pattern of 90-nm line/90-nm space was evaluated. Rating was ○ when the profile was rectangular, Δ when slight film loss occurred, and X when serious film loss was generated.

The evaluation results are shown in Table 2.

TABLE 2

| | (A) Acid Generator (g) | (B) Resin (10 g) | Basic Compound (g) | Surfactant (g) | Solvent | Pattern Collapse (nm) | Film Loss |
|---|---|---|---|---|---|---|---|
| Example | | | | | | | |
| 14 | I-1 (0.6) | SI-3 | DIA (0.03) | W-4 (0.01) | S1 | 75 | ○ |
| Comparative Example | | | | | | | |
| 3 | PAG-A (0.6) | SI-3 | DIA (0.03) | W-4 (0.01) | S1 | 85 | Δ |

The structure of Resin (SI-3) in Table 2 is shown below

SI-3

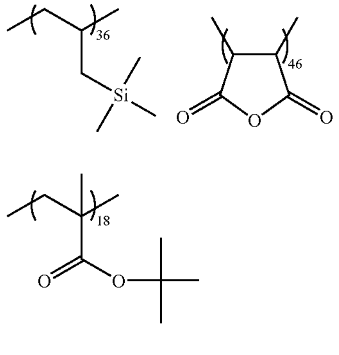

Molecular Weight: 9,600

As apparent from Table 2, the photosensitive composition of the present invention can improve the performance in terms of pattern collapse and gives a good profile.

Examples 15 and 16 and Comparative Example 4

Preparation of Resist

The components shown in Table 3 below were dissolved in a solvent, and this solution was filtered through a 0.05-μm polytetrafluoroethylene filter to prepare a positive resist solution having a solid content concentration of 14 mass %.

<Evaluation of Resist>

The positive resist solution prepared was uniformly coated by a spin coater on a silicon substrate treated with hexamethyldisilazane, and dried under heating at 120° C. for 90 seconds on a hot plate to form a 0.4-μm resist film.

This resist film was pattern-exposed using a KrF excimer laser stepper (NA=0.63) through a mask for line-and-space pattern and immediately after the exposure, heated at 110° C. for 90 seconds on a hot plate. Thereafter, the resist film was developed with an aqueous 2.38 mass % tetramethylammonium hydroxide solution at 23° C. for 60 seconds, rinsed with pure water for 30 seconds and then dried to form a line pattern.

Evaluation Method of Line Width at Which Film Loss Occurs:

The exposure amount for reproducing an isolated pattern with a line width of 130 nm was taken as an optimal exposure amount and when the exposure amount was increased from the optimal exposure amount and the line pattern was thinned, the line width at which the film loss occurred was observed. As the value is smaller, a finer pattern can be formed without causing film loss and the performance is higher.

TABLE 3

| | (A) Acid Generator (g) | (B) Resin (10 g) | Basic Compound (g) | Surfactant (g) | Solvent (ratio by mass) | Line Width at Which Film Loss Occurs (nm) |
|---|---|---|---|---|---|---|
| Example | | | | | | |
| 15 | I-1 (0.5) | R-8 | PBI (0.03) | W-4 (0.01) | S1/S2 = 70/30 | 95 |
| 16 | I-1 (0.4) | R-13 | TPSA (0.03) | W-2 (0.02) | S1/S5 = 40/60 | 95 |
| Comparative Example | | | | | | |
| 4 | PAG-A (0.5) | R-8 | PBI (0.03) | W-4 (0.01) | S1/S2 = 70/30 | 105 |

The structures of Resins (R-8) and (R-13) in Table 3 are shown below.

(R-8)

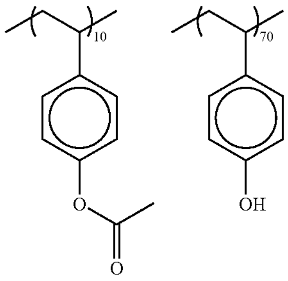

-continued

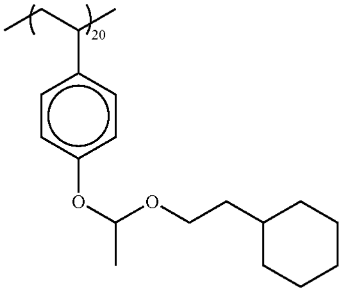

Mw = 12000
Mw/Mn = 1.2

(R-13)

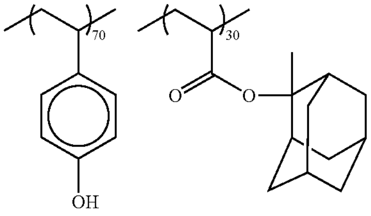

Mw = 7200
Mw/Mn = 1.56

As apparent from Table 3, the photosensitive composition of the present invention has good performance in terms of the line width at which film loss occurs.

Examples 17 and 18 and Comparative Example 5

Preparation of Resist

The components shown in Table 3 were dissolved in a solvent, and this solution was filtered through a 0.05-μm polytetrafluoroethylene filter to prepare a positive resist solution having a solid content concentration of 11 mass %.

<Evaluation of Resist>

The positive resist solution prepared was uniformly coated by a spin coater on a silicon substrate treated with hexamethyldisilazane, and dried under heating at 120° C. for 60 seconds on a hot plate to form a 250-nm resist film.

This resist film was pattern-irradiated using an electron beam direct drawing device (accelerating voltage: 50 keV) and immediately after the irradiation, heated at 120° C. for 90 seconds on a hot plate. Thereafter, the resist film was developed with an aqueous 2.38 mass % tetramethylammonium hydroxide solution at 23° C. for 60 seconds, rinsed with pure water for 30 seconds and then dried to form a line-and-space pattern.

Pattern Collapse:

The irradiation dose for reproducing a line-and-space mask pattern with a line width of 120 nm was taken as an optimal irradiation dose and when the irradiation dose was increased from the optimal irradiation dose and the line pattern was thinned, the line width at which the pattern collapsed was observed. As the value is smaller, a finer pattern can be formed without causing pattern collapse and the performance in terms of pattern collapse is higher.

The evaluation results are shown in Table 4.

TABLE 4

| | Pattern Collapse (nm) |
|---|---|
| Example | |
| 17 | 80 |
| 18 | 80 |
| Comparative Example | |
| 5 | 95 |

As apparent from Table 4, the photosensitive composition of the present invention can improve the performance in terms of pattern collapse.

This application is based on Japanese Patent application JP 2006-287220, filed Oct. 23, 2006, the entire content of which is hereby incorporated by reference, the same as if fully set forth herein.

Although the invention has been described above in relation to preferred embodiments and modifications thereof, it will be understood by those skilled in the art that other variations and modifications can be effected in these preferred embodiments without departing from the scope and spirit of the invention.

What is claimed is:

1. A photosensitive composition comprising: a non-polymeric arylsulfonium salt compound having a polycyclic hydrocarbon structure in a cation moiety, represented by the following formula (I):

(I)

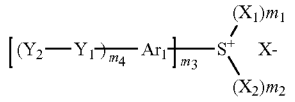

wherein $X_1$ and $X_2$ each independently represents an alkyl group, a cycloalkyl group, an aryl group or an aralkyl group, and $X_1$ and $X_2$ may combine to form a ring structure, $Ar_1$ represents an aryl group, $Y_1$ represents a single bond or a divalent linking group which is selected from the group consisting of an alkylene group, an arylene group, —O—, —S—, —$SO_2$—, —$SO_3$—, —C(=O)NRd-, —$SO_2$NRd-, and a divalent linking group comprising a plurality of these in combination, wherein Rd represents a hydrogen atom or an alkyl group, $Y_2$ represents a polycyclic hydrocarbon group, $m_1$ represents a number of from 0 to 2, $m_2$ represents a number of from 0 to 2, $m_3$ represents a number of from 1 to 3, provided that $m_1+m_2+m_3=3$, $m_4$ represents a number of from 1 to 3, and $X^-$ represents a counter anion.

2. The photosensitive composition as claimed in claim 1, wherein the arylsulfonium salt compound is a compound represented by the following formula (I-a) or (I-b):

(I-a)

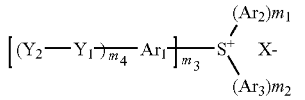

(I-b)

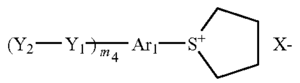

wherein $Ar_1$ represents an aryl group, $Y_1$ represents a single bond or a divalent linking group which is selected from the group consisting of an alkylene group, an arylene group, —O—, —S—, —$SO_2$—, —$SO_3$—, —C(=O)NRd-, —$SO_2$NRd-, and a divalent linking group comprising a plurality of these in combination, wherein Rd represents a hydrogen atom or an alkyl group, $Y_2$ represents a polycyclic hydrocarbon group, $m_1$ represents a number of from 0 to 2, $m_2$ represents a number of from 0 to 2, $m_3$ represents a number of from 1 to 3, provided that $m_1+m_2+m_3=3$, $m_4$ represents a number of from 1 to 3, $X^-$ represents a counter anion, and $Ar_2$ and $Ar_3$ each represent an aryl group.

3. A positive photosensitive composition comprising:

a non-polymeric arylsulfonium salt compound having a polycyclic hydrocarbon structure in a cation moiety represented by the following formula (I):

(I)

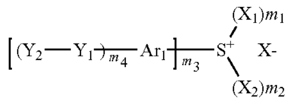

wherein $X_1$ and $X_2$ each independently represents an alkyl group, a cycloalkyl group, an aryl group or an aralkyl group, and $X_1$ and $X_2$ may combine to form a ring structure, $Ar_1$ represents an aryl group, $Y_1$ represents a single bond or a divalent linking group which is selected from the group consisting of an alkylene group, an arylene group, —O—, —S—, —$SO_2$—, —$SO_3$—, —C(=O)NRd-, —$SO_2$NRd-, and a divalent linking group comprising a plurality of these in combination, wherein Rd represents a hydrogen atom or an alkyl group, $Y_2$ represents a polycyclic hydrocarbon group, $m_1$ represents a number of from 0 to 2, $m_2$ represents a number of from 0 to 2, $m_3$ represents a number of from 1 to 3, provided that $m_1+m_2+m_3=3$, $m_4$ represents a number of from 1 to 3, and $X^-$ represents a counter anion; and a resin capable of decomposing under an action of an acid to increase a solubility in an alkali developer.

4. The positive photosensitive composition as claimed in claim 3, wherein the resin contains a hydroxystyrene repeating unit.

5. The positive photosensitive composition as claimed in claim 3, wherein the resin has a monocyclic or polycyclic alicyclic hydrocarbon structure.

6. The positive photosensitive composition as claimed in claim 3, wherein the resin has a silicon atom.

7. The positive photosensitive composition as claimed in claim 3, wherein the resin contains a repeating unit having a lactone structure.

8. A compound represented by the following formula (I):

(I)

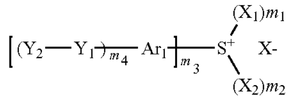

wherein $X_1$ and $X_2$ each independently represents an alkyl group, a cycloalkyl group, an aryl group or an aralkyl group, and $X_1$ and $X_2$ may combine to form a ring structure, $Ar_1$ represents an aryl group, $Y_1$ represents a single bond or a divalent linking group which is selected from the group consisting of an alkylene group, an arylene group, —O—, —S—, —$SO_2$—, —$SO_3$—, —C(═O)NRd-, —$SO_2$NRd-, and a divalent linking group comprising a plurality of these in combination, wherein Rd represents a hydrogen atom or an alkyl group, $Y_2$ represents a polycyclic hydrocarbon group, $m_1$ represents a number of from 0 to 2, $m_2$ represents a number of from 0 to 2, $m_3$ represents a number of from 1 to 3, provided that $m_1+m_2+m_3=3$, $m_4$ represents a number of from 1 to 3, and $X^-$ represents a counter anion.

9. The compound as claimed in claim 8, wherein the polycyclic hydrocarbon group represented by $Y_2$ is a bicyclic or greater polycyclic hydrocarbon group.

10. The compound as claimed in claim 8, wherein the polycyclic hydrocarbon group represented by $Y_2$ is an adamantyl group, a norbornane group, a bicyclo[2.2.2]octane group, a tetracyclododecanyl group, a tricyclodecanyl group or a diamantyl group.

11. A pattern forming method comprising: forming a photosensitive film from the photosensitive composition claimed in claim 1; and exposing and developing the photosensitive film.

12. The positive photosensitive composition as claimed in claim 7, wherein the resin has a repeating unit represented by the formula (AI):

(AI)

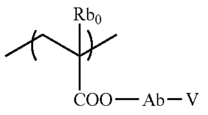

wherein, $Rb_0$ represents a hydrogen atom, a halogen atom or an alkyl group having a carbon number of 1 to 4;

Ab represents a single bond, an alkylene group, a divalent linking group having a monocyclic or polycyclic alicyclic hydrocarbon structure, an ether group, an ester group, a carbonyl group, a carboxyl group, or a divalent group comprising a combination thereof; and V represents a group represented by any one of formulae (LC1-1) to (LC1-16):

LC1-1

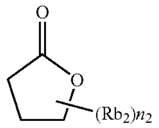

LC1-2

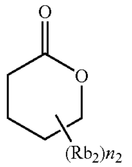

LC1-3

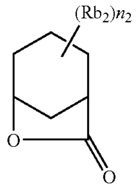

LC1-4

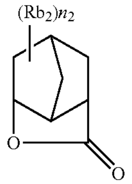

LC1-5

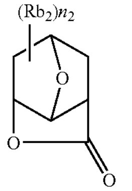

LC1-6

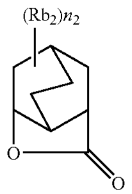

LC1-7

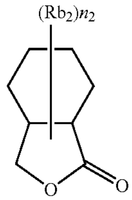

-continued

LC1-8

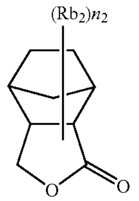

LC1-9

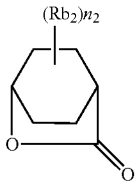

LC-10

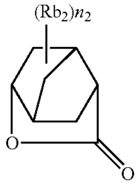

LC1-11

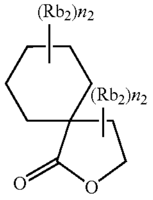

LC1-12

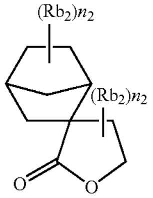

LC1-13

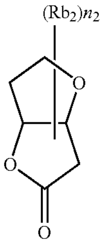

LC1-14

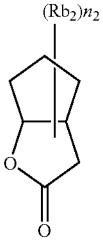

-continued

LC1-15

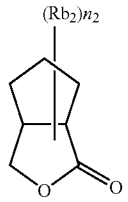

LC1-16

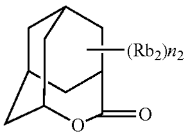

wherein $Rb_2$ represents an alkyl group having a carbon number of 1 to 8, a cycloalkyl group having a carbon number of 4 to 7, an alkoxy group having a carbon number of 1 to 8, an alkoxycarbonyl group having a carbon number of 1 to 8, a carboxyl group, a halogen atom, a hydroxyl group, a cyano group or an acid-decomposable group; and $n_2$ represents an integer of 0 to 4, and when $n_2$ is an integer of 2 or more, the plurality of substituents ($Rb_2$) may be the same or different and also, the plurality of substituents ($Rb_2$) may combine with each other to form a ring.

13. A photosensitive composition comprising: a non-polymeric arylsulfonium salt compound having a polycyclic hydrocarbon structure in a cation moiety, represented by the following formula (I):

(I)

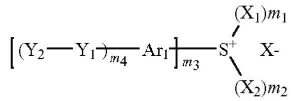

wherein $X_1$ and $X_2$ each independently represents an alkyl group, a cycloalkyl group, an aryl group or an aralkyl group, and $X_1$ and $X_2$ combine to form a ring structure, $Ar_1$ represents an aryl group, $Y_1$ represents a single bond or a divalent linking group, $Y_2$ represents a polycyclic hydrocarbon group, $m_1$ represents a number of from 0 to 2, $m_2$ represents a number of from 0 to 2, $m_3$ represents a number of from 1 to 3, provided that $m_1+m_2+m_3=3$, $m_4$ represents a number of from 1 to 3, and $X^-$ represents a counter anion.

14. A photosensitive composition comprising: a non-polymeric arylsulfonium salt compound having a polycyclic hydrocarbon structure in a cation moiety, represented by the following formula (I):

(I)

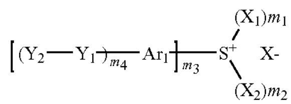

wherein $X_1$ and $X_2$ each independently represents an alkyl group, a cycloalkyl group, an aryl group or an aralkyl group, and $X_1$ and $X_2$ may combine to form a ring structure, $Ar_1$ represents an aryl group, $Y_1$ represents a single bond or a divalent linking group, $Y_2$ represents a 1-adamantyl group, $m_1$ represents a number of from 0 to 2, $m_2$ represents a number of from 0 to 2, $m_3$ represents a number of from 1 to 3, provided that $m_1+m_2+m_3=3$, $m_4$ represents a number of from 1 to 3, and $X^-$ represents a counter anion.

15. A photosensitive composition comprising: a non-polymeric arylsulfonium salt compound having a polycyclic hydrocarbon structure in a cation moiety, represented by the following formula (I):

(I)

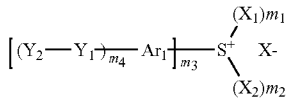

wherein $X_1$ and $X_2$ each independently represents an alkyl group, a cycloalkyl group, an aryl group or an aralkyl group, and $X_1$ and $X_2$ may combine to form a ring structure, $Ar_1$ represents an aryl group, $Y_1$ represents a single bond or a divalent linking group, $Y_2$ represents a norbornane group, a bicyclo[2.2.2]octane group, a tetracyclododecanyl group, a tricyclodecanyl group or a diamantyl group, $m_1$ represents a number of from 0 to 2, $m_2$ represents a number of from 0 to 2, $m_3$ represents a number of from 1 to 3, provided that $m_1+m_2+m_3=3$, $m_4$ represents a number of from 1 to 3, and $X^-$ represents a counter anion.

16. A photosensitive composition comprising: a non-polymeric arylsulfonium salt compound having a polycyclic hydrocarbon structure in a cation moiety, represented by the following formula (I):

(I)

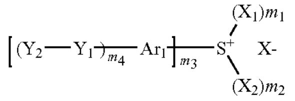

wherein $X_1$ and $X_2$ each independently represents an alkyl group, a cycloalkyl group, an aryl group or an aralkyl group, and $X_1$ and $X_2$ may combine to form a ring structure, $Ar_1$ represents an aryl group, $Y_1$ represents a single bond or a divalent linking group, $Y_2$ represents a polycyclic hydrocarbon group not capable of decomposing by the action of an acid, $m_1$ represents a number of from 0 to 2, $m_2$ represents a number of from 0 to 2, $m_3$ represents a number of from 1 to 3, provided that $m_1+m_2+m_3=3$, $m_4$ represents a number of from 1 to 3, and $X^-$ represents a counter anion.

* * * * *